(12) United States Patent
Mabood et al.

(10) Patent No.: US 12,070,037 B2
(45) Date of Patent: Aug. 27, 2024

(54) **METHODS AND COMPOSITIONS FOR BIOPROTECTION OF POTATOES FROM *STREPTOMYCES SCABIES***

(71) Applicant: THE ROYAL INSTITUTION FOR THE ADVANCEMENT OF LEARNING/MCGILL UNIVERSITY, Montréal (CA)

(72) Inventors: Fazli Mabood, Centennial, CO (US); Aaron L. Waltz, Centennial, CO (US); Margaret Ann Bywater-Ekegard, Centennial, CO (US); Donald Lawrence Smith, Montreal (CA)

(73) Assignee: The Royal Institution for the Advancement of Learning/McGill University, Montreal (CA)

(*) Notice: Subject to any disclaimer, the term of this patent is extended or adjusted under 35 U.S.C. 154(b) by 670 days.

(21) Appl. No.: 17/279,679

(22) PCT Filed: Sep. 27, 2019

(86) PCT No.: PCT/US2019/053646
§ 371 (c)(1),
(2) Date: Mar. 25, 2021

(87) PCT Pub. No.: WO2020/069436
PCT Pub. Date: Apr. 2, 2020

(65) Prior Publication Data
US 2021/0392902 A1      Dec. 23, 2021

Related U.S. Application Data

(60) Provisional application No. 62/737,747, filed on Sep. 27, 2018, provisional application No. 62/744,101, filed on Oct. 10, 2018.

(51) Int. Cl.
*A01N 63/22* (2020.01)
*C12N 1/20* (2006.01)

(52) U.S. Cl.
CPC .............. *A01N 63/22* (2020.01); *C12N 1/20* (2013.01); *C12N 2500/30* (2013.01)

(58) Field of Classification Search
None
See application file for complete search history.

(56) References Cited

U.S. PATENT DOCUMENTS

| | | |
|---|---|---|
| 5,733,777 A | 3/1998 | Dudney |
| 9,175,258 B2 | 11/2015 | Bywater-Ekegard et al. |
| 10,258,040 B2 * | 4/2019 | Muenks ................ A01N 43/80 |
| 2016/0100587 A1 | 1/2016 | Bywater-Ekegard et al. |
| 2016/0102251 A1 | 4/2016 | Bywater-Ekegard et al. |

FOREIGN PATENT DOCUMENTS

| | | |
|---|---|---|
| CN | 107427012 | 12/2017 |
| JP | 2007153873 | 6/2007 |
| WO | WO2013/165607 A1 | 11/2013 |
| WO | WO2016/178086 A1 | 11/2016 |

OTHER PUBLICATIONS

Karagozet et. al.( The Journal of Animal & Plant Sciences, 28(4): 2018, p. 1068-1073, Screening bacterial antagonists to common scab disease, vol. 28, No. 4, 1068-1073, 39 refs., 2018). (Year: 2018).*
Weinhold A. R. et al, Selective inhibition of the potato scab pathogen by antagonistic bacteria and substrate influence on antibiotic production, Plant and Soil, vol. 28, No. 1, Feb. 2, 1968, pp. 12-24, (Year: 1968).*
Fuller A. T. : "A New Antibiotic of Bacterial Origin", Nature, vol. 23, Apr. 23, 1955 (Apr. 23, 1955), p. 722, XP055910474.
Zimmer Tammy: "United States Environmental Protection Agency", Mar. 4, 2015 (Mar. 4, 2015), pp. 1-64, XP055910752, Retrieved from the Internet: URL:https://www3.epa.gov/pesticides/chem_search/ppls/000264-01153-201.
Sturz A.Vet al: "Stimulating disease 1 suppression in soils: sulphate fertilizers can increase biodiversity and antibiosis ability of root zone bacteria against Streptomyces scabies", Soil Biology and Biochemistry, vol. 36, No. 2, Feb. 1, 2004 (Feb. 1, 2004), pp. 343-352, XP055910749, GB ISSN: 0038-0717, DOI: 10.1016/j.soilbio.2003.10.009.
Lanna-Filho, Roberto, Souza, Ricardo M., Magalhães, Marcelo M., et al. Induced defense responses in tomato against bacterial spot by proteins synthesized by endophytic bacteria. Tropical Plant Pathology, 2013, vol. 38, p. 295-302.
Abraham, E. P., Heatley, N. G., Brookes, P., et al. Probable identity of an antibiotic produced by a spore-bearing bacillus of the *B. pumilus* group with micrococcin. Nature, 1956, vol. 178, No. 4523, p. 44-45.
Girish, N. et Umesha, S. Effect of plant growth promoting rhizobacteria on bacterial canker of tomato. Archives of Phytopathology and Plant protection, 2005, vol. 38, No. 3, p. 235-243.
Lefranc, David et Ciufolini, Marco A. Total synthesis and stereochemical assignment of micrococcin P1. Angewandte Chemie, 2009, vol. 48, No. 23, p. 4198-4201.

* cited by examiner

*Primary Examiner* — Alton N Pryor
(74) *Attorney, Agent, or Firm* — Fasken Martineau DuMoulin LLP; Serge Lapointe

(57) ABSTRACT

The present invention relates to compositions having antimicrobial activity against *Streptomyces scabies*. Further provided herein are methods of making and using the antimicrobial compositions to protect and treat potatoes from *Streptomyces scabies* infections.

Figures 1A, 1B:
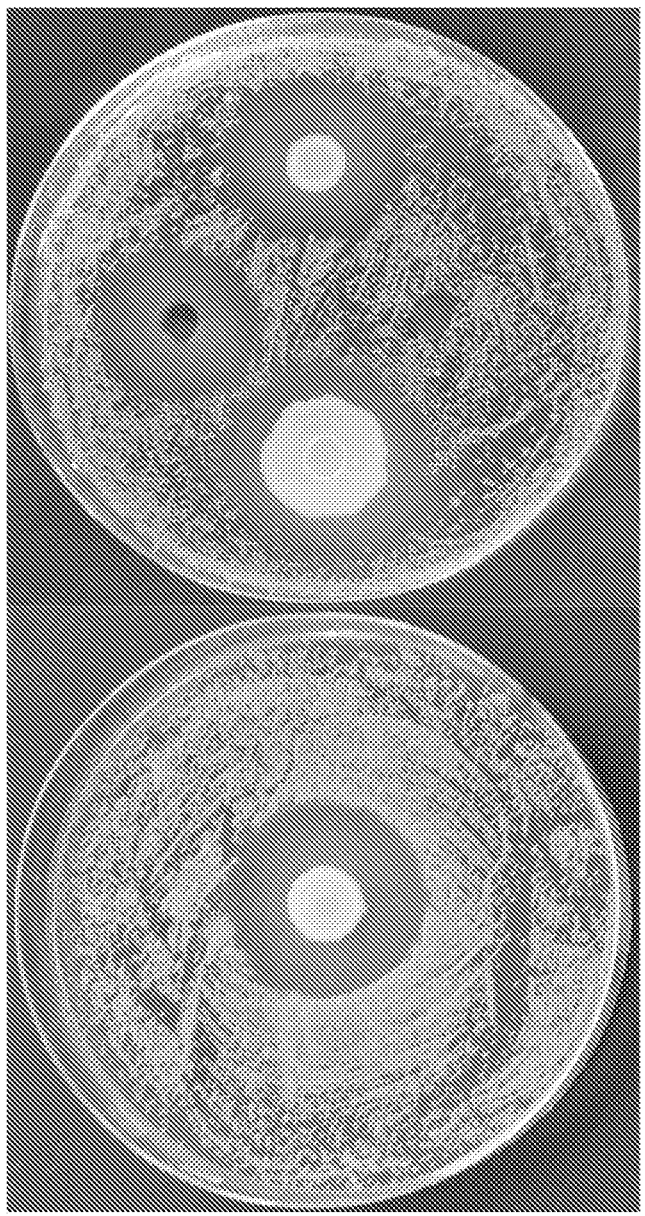

16 Claims, 25 Drawing Sheets
Specification includes a Sequence Listing.

Figure 6

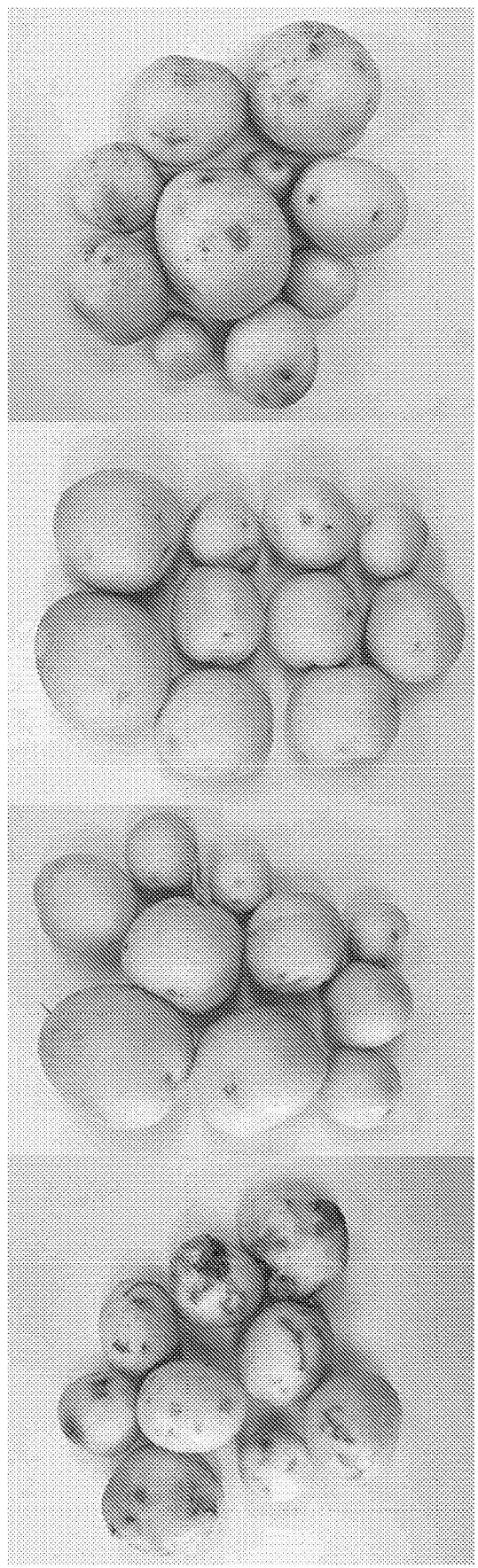

SEQUENCE LISTING

<160> NUMBER OF SEQ ID NOS: 8

<210> SEQ ID NO 1
<211> LENGTH: 1378
<212> TYPE: DNA
<213> ORGANISM: Bacillus pumilus

<400> SEQUENCE: 1
gagcttgctc ccggatgtta gcggcggacg ggtgagtaac acgtgggtaa cctgcctgta      60
agactgggat aactccggga aaccggagct aataccggat agttccttga accgcatggt     120
tcaaggatga agacggtttt cggctgtcac ttacagatgg acccgcggcg cattagctag     180

-continued

```
ttggtgaggt aacggctcac caaggcgacg atgcgtagcc gacctgagag ggtgatcggc        240
cacactggga ctgagacacg gcccagactc ctacgggagg cagcagtagg gaatcttccg        300
caatggacga aagtctgacg gagcaacgcc gcgtgagtga tgaaggtttt cggatcgtaa        360
agctctgttg ttagggaaga acaagtgcaa gagtaactgc ttgcaccttg acggtaccta        420
accagaaagc cacggctaac tacgtgccag cagccgcggt aatacgtagg tggcaagcgt        480
tgtccggaat tattgggcgt aaagggctcg caggcggttt cttaagtctg atgtgaaagc        540
ccccggctca accggggagg gtcattggaa actgggaaac ttgagtgcag aagaggagag        600
tggaattcca cgtgtagcgg tgaaatgcgt agagatgtgg aggaacacca gtggcgaagg        660
cgactctctg gtctgtaact gacgctgagg agcgaaagcg tggggagcga acaggattag        720
atacctggt agtccacgcc gtaaacgatg agtgctaagt gttaggggt ttccgcccct         780
tagtgctgca gctaacgcat taagcactcc gcctgggag tacggtcgca agactgaaac         840
tcaaaggaat tgacggggc ccgcacaagc ggtggagcat gtggtttaat tcgaagcaac         900
gcgaagaacc ttaccaggtc ttgacatcct ctgacaaccc tagagatagg ctttcccctt        960
cggggacaga gtgacaggtg gtgcatggtt gtcgtcagct cgtgtcgtga tgttgggt         1020
taagtcccgc aacgagcgca acccttgatc ttagttgcca gcattcagtt gggcactcta       1080
aggtgactgc cggtgacaaa ccggaggaag gtggggatga cgtcaaatca tcatgcccct       1140
tatgacctgg gctacacacg tgctacaatg gacagaacaa agggctgcga gaccgcaagg       1200
tttagccaat cccacaaatc tgttctcagt tcggatcgca gtctgcaact cgactgcgtg       1260
aagctggaat cgctagtaat cgcggatcag catgccgcgg tgaatacgtt cccgggcctt       1320
gtacacaccg cccgtcacac cacgagagtt tgcaacaccc gaagtcggtg aggtaacc        1378
```

<210> SEQ ID NO 2
<211> LENGTH: 1399
<212> TYPE: DNA
<213> ORGANISM: Bacillus subtilis
<220> FEATURE:
<221> NAME/KEY: modified_base
<222> LOCATION: (196)..(197)
<223> OTHER INFORMATION: a, c, t, g, unknown or other

<400> SEQUENCE: 2

```
gcagtcgagc ggacagatgg gagcttgctc cctgatgtta gcggcggacg ggtgagtaac         60
acgtgggtaa cctgcctgta agactgggat aactccggga aaccggggct aataccggat        120
gcttgtttga accgcatggt tcaaacataa aaggtggctt cggctaccac ttacagatgg        180
acccgcggcg cattanntag ttggtgaggt aacggctcac caaggcaacg atgcgtagcc        240
gacctgagag ggtgatcggc cacactggga ctgagacacg gcccagactc ctacgggagg        300
cagcagtagg gaatcttccg caatggacga aagtctgacg gagcaacgcc gcgtgagtga        360
tgaaggtttt cggatcgtaa agctctgttg ttagggaaga acaagtaccg ttcgaatagg        420
gcggtacctt gacggtacct aaccagaaag ccacggctaa ctacgtgcca gcagccgcgg        480
taatacgtag gtggcaagcg ttgtccggaa ttattgggcg taaagggctc gcaggcggtt        540
tcttaagtct gatgtgaaag ccccggctc aaccggggag gtcattgga actgggaa           600
cttgagtgca gaagaggaga gtggaattcc acgtgtagcg gtgaaatgcg tagagatgtg        660
gaggaacacc agtggcgaag gcgactctct ggtctgtaac tgacgctgag gagcgaaagc        720
gtggggagcg aacaggatta gatacctggt agtccacgcc gtaaacgatg agtgctaag         780
tgttagggg tttccgcccc ttagtgctgc agctaacgca ttaagcactc cgcctgggga        840
```

```
gtacggtcgc aagactgaaa ctcaaaggaa ttgacggggg cccgcacaag cggtggagca      900
tgtggtttaa ttcgaagcaa cgcgaagaac cttaccaggt cttgacatcc tctgacaatc      960
ctagagatag gacgtcccct cgggggcag agtgacaggt ggtgcatggt tgtcgtcagc      1020
tcgtgtcgtg agatgttggg ttaagtcccg caacgagcgc aacccttgat cttagttgcc     1080
agcattcagt tgggcactct aaggtgactg ccggtgacaa accggaggaa ggtggggatg     1140
acgtcaaatc atcatgcccc ttatgacctg gctacacac gtgctacaat ggacagaaca      1200
aagggcagcg aaaccgcgag gttaagccaa tcccacaaat ctgttctcag ttcggatcgc     1260
agtctgcaac tcgactgcgt gaagctgaa tcgctagtaa tcgcggatca gcatgccgcg      1320
gtgaatacgt tcccgggcct tgtacacacc gcccgtcaca ccacgagagt ttgtaacacc     1380
cgaagtcggt gaggtaacc                                                   1399

<210> SEQ ID NO 3
<211> LENGTH: 1202
<212> TYPE: DNA
<213> ORGANISM: Bacillus subtilis

<400> SEQUENCE: 3
tagttggtga ggtaacggct caccaaggca acgatgcgta gccgacctga gagggtgatc       60
ggccacactg ggactgagac acggcccaga ctcctacggg aggcagcagt agggaatctt      120
ccgcaatgga cgaaagtctg acggagcaac gccgcgtgag tgatgaaggt tttcggatcg      180
taaagctctg ttgttaggga gaacaagta ccgttcgaat agggcggtac cttgacggta      240
cctaaccaga aagccacggc taactacgtg ccagcagccg cggtaatacg taggtggcaa      300
gcgttgtccg gaattattgg gcgtaaaggg ctcgcaggcg gtttcttaag tctgatgtga     360
aagcccccgg ctcaaccggg gagggtcatt ggaaactggg gaacttgagt gcagaagagg      420
agagtggaat tccacgtgta gcggtgaaat gcgtagagat gtggaggaac accagtggcg      480
aaggcgactc tctggtctgt aactgacgct gaggagcgaa agcgtgggga gcaacagga      540 ttagatacc tggtagtcca cgccgtaaac gatgagtgct aagtgttagg gggtttccgc       600
cccttagtgc tgcagctaac gcattaagca ctccgcctgg ggagtacggt cgcaagactg      660
aaactcaaag gaattgacgg gggcccgcac aagcggtgga gcatgtggtt taattcgaag      720
caacgcgaag aaccttacca ggtcttgaca tcctctgaca atcctagaga taggacgtcc      780
ccttcggggg cagagtgaca ggtggtgcat ggttgtcgtc agctcgtgtc gtgagatgtt      840
gggttaagtc ccgcaacgag cgcaaccctt gatcttagtt gccagcattc agttgggcac     900
tctaaggtga ctgccggtga caaaccggag gaaggtgggg atgacgtcaa atcatcatgc      960
cccttatgac ctgggctaca cacgtgctac aatggacaga acaaagggca gcgaaaccgc     1020
gaggttaagc caatcccaca aatctgttct cagttcggat cgcagtctgc aactcgactg     1080
cgtgaagctg gaatcgctag taatcgcgga tcagcatgcc gcggtgaata cgttcccggg     1140
ccttgtacac accgcccgtc acaccacgag agtttgtaac acccgaagtc ggtgaggtaa     1200
cc                                                                    1202

<210> SEQ ID NO 4
<211> LENGTH: 1440
<212> TYPE: DNA
<213> ORGANISM: Bacillus pumilus
```

<400> SEQUENCE: 4

```
gtgcgggtgc tataatgcag tcgagcggac agaagggagc ttgctcccgg atgttagcgg      60
cggacgggtg agtaacacgt gggtaacctg cctgtaagac tgggataact ccgggaaacc     120
ggagctaata ccggatagtt ccttgaaccg catggttcaa ggatgaaaga cggtttcggc     180
tgtcacttac agatggaccc gcggcgcatt agctagttgg tgaggtaacg gctcaccaag     240
gcgacgatgc gtagccgacc tgagagggtg atcggccaca ctgggactga gacacggccc     300
agactcctac gggaggcagc agtagggaat cttccgcaat ggacgaaagt ctgacggagc     360
aacgccgcgt gagtgatgaa ggttttcgga tcgtaaagct ctgttgttag gaagaacaa     420
gtgcaagagt aactgcttgc accttgacgg tacctaacca gaaagccacg gctaactacg     480
tgccagcagc cgcggtaata cgtaggtggc aagcgttgtc cggaattatt gggcgtaaag     540
ggctcgcagg cggtttctta agtctgatgt gaaagccccc ggctcaaccg ggagggtca     600
ttggaaactg ggaacttga gtgcagaaga ggagagtgga attccacgtg tagcggtgaa     660
atgcgtagag atgtggagga acaccagtgg cgaaggcgac tctctggtct gtaactgacg     720
ctgaggagcg aaagcgtggg gagcgaacag gattagatac cctggtagtc cacgccgtaa     780
acgatgagtg ctaagtgtta gggggttcc gccccttagt gctgcagcta acgcattaag     840
cactccgcct ggggagtacg gtcgcaagac tgaaactcaa aggaattgac ggggcccgc     900
acaagcggtg gagcatgtgg tttaattcga agcaacgcga agaaccttac caggtcttga     960
catcctctga caaccctaga gatagggctt tccttcgggg acagagtga caggtggtgc    1020
atggttgtcg tcagctcgtg tcgtgagatg ttgggttaag tcccgcaacg agcgcaaccc    1080
ttgatcttag ttgccagcat tcagttgggc actctaaggt gactgccggt gacaaaccgg    1140
aggaaggtgg ggatgacgtc aaatcatcat gccccttatg acctgggcta cacacgtgct    1200
acaatggaca gaacaaaggg ctgcgagacc gcaaggttta gccaatccca caaatctgtt    1260
ctcagttcgg atcgcagtct gcaactcgac tgcgtgaagc tggaatcgct agtaatcgcg    1320
gatcagcatg ccgcggtgaa tacgttcccg ggccttgtac acaccgcccg tcacaccacg    1380
agagtttgca acacccgaag tcggtgaggt aacctttatg gagccagccg ccgaacgttc    1440
```

<210> SEQ ID NO 5
<211> LENGTH: 1448
<212> TYPE: DNA
<213> ORGANISM: Bacillus subtilis

<400> SEQUENCE: 5

```
tggcggcgtg ctataatgca gtcgagcgga cagatgggag cttgctccct gatgttagcg      60
gcggacgggt gagtaacacg tgggtaacct gcctgtaaga ctgggataac tccgggaaac     120
cggggctaat accggatgct tgtttgaacc gcatggttca acataaaag gtggcttcgg     180
ctaccactta cagatggacc gcggcgcat tagctagttg tgaggtaac ggctcaccaa     240
ggcaacgatg cgtagccgac ctgagagggt gatcggccac actgggactg agacacggcc     300
cagactccta cggaggcag cagtagggaa tcttccgcaa tggacgaaag tctgacggag     360
caacgccgcg tgagtgatga aggttttcgg atcgtaaagc tctgttgtta gggaagaaca     420
agtaccgttc gaatagggcg gtaccttgac ggtacctaac cagaaagcca cggctaacta     480
cgtgccagca gccgcggtaa tacgtaggtg caagcgttg tccggaatta ttgggcgtaa     540
agggctcgca ggcggtttct taagtctgat gtgaaagccc ccggctcaac cggggagggt     600
```

| | |
|---|---:|
| cattggaaac tggggaactt gagtgcagaa gaggagagtg gaattccacg tgtagcggtg | 660 |
| aaatgcgtag agatgtggag gaacaccagt ggcgaaggcg actctctggt ctgtaactga | 720 |
| cgctgaggag cgaaagcgtg gggagcgaac aggattagat accctggtag tccacgccgt | 780 |
| aaacgatgag tgctaagtgt tagggggttt ccgccccta gtgctgcagc taacgcatta | 840 |
| agcactccgc ctggggagta cggtcgcaag actgaaactc aaaggaattg acggggccc | 900 |
| gcacaagcgg tggagcatgt ggtttaattc gaagcaacgc gaagaacctt accaggtctt | 960 |
| gacatcctct gacaatccta gagataggac gtccccttcg ggggcagagt gacaggtggt | 1020 |
| gcatggttgt cgtcagctcg tgtcgtgaga tgttgggtta agtcccgcaa cgagcgcaac | 1080 |
| ccttgatctt agttgccagc attcagttgg gcactctaag gtgactgccg gtgacaaacc | 1140 |
| ggaggaaggt ggggatgacg tcaaatcatc atgccccta tgacctgggc tacacacgtg | 1200 |
| ctacaatgga cagaacaaag ggcagcgaaa ccgcgaggtt aagccaatcc cacaaatctg | 1260 |
| ttctcagttc ggatcgcagt ctgcaactcg actgcgtgaa gctggaatcg ctagtaatcg | 1320 |
| cggatcagca tgccgcggtg aatacgttcc cgggccttgt acacaccgcc cgtcacacca | 1380 |
| cgagagtttg taacacccga agtcggtgag gtaaccttt aggagccagc cgccgaaggg | 1440 |
| acagagag | 1448 |

<210> SEQ ID NO 6
<211> LENGTH: 1522
<212> TYPE: DNA
<213> ORGANISM: Bacillus subtilis

<400> SEQUENCE: 6

| | |
|---|---:|
| ctggctcagg acgaacgctg gcggcgtgcc taatacatgc aagtcgagcg gacagatggg | 60 |
| agcttgctcc ctgatgttag cggcggacgg gtgagtaaca cgtgggtaac ctgcctgtaa | 120 |
| gactgggata actccgggaa accggggcta ataccggatg gttgtttgaa ccgcatggtt | 180 |
| caaacataaa aggtggcttc ggctaccact tacagatgga cccgcggcgc attagctagt | 240 |
| tggtgaggta acggctcacc aaggcaacga tgcgtagccg acctgagagg gtgatcggcc | 300 |
| acactgggac tgagacacgg cccagactcc tacgggaggc agcagtaggg aatcttccgc | 360 |
| aatggacgaa agtctgacgg agcaacgccg cgtgagtgat gaaggtttc ggatcgtaaa | 420 |
| gctctgttgt tagggaagaa caagtaccgt tcgaataggg cggtaccttg acggtaccta | 480 |
| accagaaagc cacggctaac tacgtgccag cagccgcggt aatacgtagg tggcaagcgt | 540 |
| tgtccggaat tattgggcgt aaagggctcg caggcggttt cttaagtctg atgtgaaagc | 600 |
| ccccggctca accggggagg gtcattggaa actggggaac ttgagtgcag aagaggagag | 660 |
| tggaattcca cgtgtagcgg tgaaatgcgt agagatgtgg aggaacacca gtggcgaagg | 720 |
| cgactctctg gtctgtaact gacgctgagg agcgaaagcg tggggagcga acaggattag | 780 |
| ataccctggt agtccacgcc gtaaacgatg agtgctaagt gttagggggt ttccgcccct | 840 |
| tagtgctgca gctaacgcat taagcactcc gcctggggag tacggtcgca agactgaaac | 900 |
| tcaaaggaat tgacggggc cgcacaagc ggtggagcat gtggtttaat tcgaagcaac | 960 |
| gcgaagaacc ttaccaggtc ttgacatcct ctgacaatcc tagagatagg acgtcccctt | 1020 |
| cggggggcaga gtgacaggtg gtgcatggtt gtcgtcagct cgtgtcgtga gatgttgggt | 1080 |
| taagtcccgc aacgagcgca acccttgatc ttagttgcca gcattcagtt gggcactcta | 1140 |
| aggtgactgc cggtgacaaa ccggaggaag gtggggatga cgtcaaatca tcatgccct | 1200 |
| tatgacctgg gctacacacg tgctacaatg gacagaacaa agggcagcga accgcgagg | 1260 |

```
ttaagccaat cccacaaatc tgttctcagt tcggatcgca gtctgcaact cgactgcgtg    1320
aagctggaat cgctagtaat cgcggatcag catgccgcgg tgaatacgtt cccgggcctt    1380
gtacacaccg cccgtcacac cacgagagtt tgtaacaccc gaagtcggtg aggtaacctt    1440
ttaggagcca gccgccgaag gtgggacaga tgattggggt gaagtcgtaa caaggtagcc    1500
gtatcggaag gtgcggttgg at                                             1522

<210> SEQ ID NO 7
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
agagtttgat cmtggctcag                                                20

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tacggytacc ttgttacgac tt                                             22
```

METHODS AND COMPOSITIONS FOR BIOPROTECTION OF POTATOES FROM STREPTOMYCES SCABIES

1. BACKGROUND

*Streptomyces scabies*, the causal agent of common scab of potatoes, is a gram-positive bacterium with a filamentous growth form and causes common scab of potato in many potato-growing fields worldwide. Disease incidence and severity can vary from year to year, field to field and region to region depending upon the pathogen population in the soil, environmental conditions and potato susceptibility. Common scab disease of potato has negligible effect on tuber yield; however, it greatly affects tuber quality and as such results in substantial economic losses due to reduced marketability of the tubers.

Once established, *Streptomyces scabies* can survive in the soil for many years as saprophytes on plant debris and organic matter and this makes the disease difficult to control. In the past, efforts have been made to control potato scab disease using chemical fumigation and common cultural practices such as crop rotation, irrigation and soil amendments; however, the results were inconsistent. The use of fumigation to control scab disease may provide short-term control of the pathogen, but the economic and environmental costs of repeated fumigation are high. Once the pathogen is established in the field, it is difficult to eradicate as it can survive for extended periods on plant debris and consequently crop rotation offers limited control of this pathogen. There are no safe and effective pesticides available for the control of common scab of potato. Due to the combination of these factors, common scab of potato is one of the most serious diseases of potatoes worldwide.

There is, therefore, a need for a safe and effective method and composition for protecting potatoes from *Streptomyces scabies*.

2. SUMMARY

The present invention relates to a novel composition for protecting potatoes from *Streptomyces scabies*, and methods of making and using the compositions.

Specifically, in an aspect, the present invention provides a method of protecting potatoes from *Streptomyces scabies*, comprising the step of applying an effective amount of a bacterial culture comprising *Bacillus pumilus* to a soil, the soil exposed to *Streptomyces scabies*, wherein the effective amount is sufficient for bioprotection of the potatoes from *Streptomyces scabies*, wherein the bioprotection of the potatoes is assessed at the time of harvesting the potatoes from the soil.

In some embodiments, the bacterial culture comprises a culture medium inoculated with *Bacillus pumilus*.

In some embodiments, the bacterial culture is bottled before the step of applying. In some embodiments, the bacterial culture is incubated with *Bacillus pumilus* for 3-20 days, 5-15 days, 5-10 days, 6-8 days or 7 days before being bottled. In some embodiments, the bacterial culture is incubated with *Bacillus pumilus* at 25-37° C., 28-35° C., 28-32° C. or 30° C. before being bottled.

In some embodiments, the culture medium is an LB broth.

In some embodiments, the bacterial culture comprises Micrococcin P1. In some embodiments, the Micrococcin P1 is produced by the *Bacillus pumilus*.

In some embodiments, before the step of applying the bacterial culture to the soil, the bacterial culture is mixed with a cell free supernatant of a microorganism mixture comprising *Lactobacillus paracasei, Lactobacillus helveticus, Lactobacillus plantarum, Lactobacillus rhamnosus, Lactococcus lactis, Bacillus amyloliquefaciens, Aspergillus oryzae, Saccharomyces cerevisiae, Candida utilis*, and *Rhodopseudomonas palustris*. In some embodiments, the microorganism mixture is produced by incubating IN-M1, deposited under ATCC Accession No. PTA-12383, or IN-M2, deposited under ATCC Accession No. PTA-121556.

In some embodiments, the bacterial culture is mixed with a different bacterial culture comprising *Bacillus subtilis*, before the step of applying the bacterial culture to the soil.

In some embodiments, the soil is in a pot. In some embodiments, the bacterial culture is applied to the soil to provide a final concentration of *Bacillus pumilus* that ranges between $10^7$ and $10^9$ CFU/$cm^3$, between $2.5\times10^7$ and $7.5\times10^8$ CFU/$cm^3$, between $5\times10^7$ and $5\times10^8$ CFU/$cm^3$, or $10^8$ CFU/$cm^3$.

In some embodiments, the soil is in a field. In some embodiments, the bacterial culture is applied to a furrow in the field. In some embodiments, the effective amount of the bacterial culture is between 0.2 and 3 gal/A, between 0.5 and 2.5 gal/A, between 0.75 and 2 gal/A, 0.5 gal/A, 1 gal/A, 1.25 gal/A, 1.5 gal/A, or 2 gal/A.

In some embodiments, the harvesting is done 5-20 weeks, 10-15 weeks, 10-14 weeks, 11 weeks, 12 weeks, 13 weeks, or 14 weeks after the step of applying.

In some embodiments, the potatoes are Yukon Gold, Kennebec, Red Pontiac, Shepody, Russet Burbank, Atlantic, Red Lasota, Sifra, Prospect, or Goldrush.

In some embodiments, the bioprotection from *Streptomyces scabies* infection is determined based on average surface areas affected by *Streptomyces scabies*. In some embodiments, the bioprotection from *Streptomyces scabies* infection is determined based on potato yields. In some embodiments, the bioprotection from *Streptomyces scabies* infection is determined based on a cull rate.

In another aspect, the present invention provides a method of protecting potatoes from *Streptomyces scabies*, comprising the step of: applying an effective amount of a bacterial culture comprising *Bacillus subtilis* to a soil, the soil exposed to *Streptomyces scabies*, wherein the effective amount is sufficient for bioprotection of the potatoes from *Streptomyces scabies*, wherein the bioprotection of the potatoes is assessed at the time of harvesting the potatoes from the soil.

In some embodiments, the bacterial culture comprises a culture medium inoculated with *Bacillus subtilis*.

In some embodiments, the bacterial culture is bottled before the step of applying. In some embodiments, the bacterial culture is incubated with *Bacillus subtilis* for 3-20 days, 5-15 days, 5-10 days, 6-8 days or 7 days before being bottled. In some embodiments, the bacterial culture is incubated with *Bacillus subtilis* at 25-37° C., 28-35° C., 28-32° C. or 30° C. before being bottled.

In some embodiments, the culture medium is an LB broth.

In some embodiments, before the step of applying the bacterial culture to the soil, the bacterial culture is mixed with a cell free supernatant of a microorganism mixture comprising *Lactobacillus paracasei, Lactobacillus helveticus, Lactobacillus plantarum, Lactobacillus rhamnosus, Lactococcus lactis, Bacillus amyloliquefaciens, Aspergillus oryzae, Saccharomyces cerevisiae, Candida utilis*, and *Rhodopseudomonas palustris*. In some embodiments, the bacterial culture is produced by incubating IN-M1, deposited under ATCC Accession No. PTA-12383, or IN-M2, deposited under ATCC Accession No. PTA-121556.

In some embodiments, the bacterial culture is mixed with a different bacterial culture comprising *Bacillus pumilus*, before the step of applying the bacterial culture to the soil.

In some embodiments, the soil is in a pot. In some embodiments, the bacterial culture is applied to the soil to provide a final concentration of *Bacillus pumilus* that ranges between $10^7$ and $10^9$ CFU/cm$^3$, between $2.5\times10^7$ and $7.5\times10^8$ CFU/cm$^3$, between $5\times10^7$ and $5\times10^8$ CFU/cm$^3$, or $10^8$ CFU/cm$^3$.

In some embodiments, the soil is in a field. In some embodiments, the bacterial culture is applied to a furrow in the field. In some embodiments, the effective amount of the bacterial culture is between 0.2 and 3 gal/A, between 0.5 and 2.5 gal/A, between 0.75 and 2 gal/A, 0.5 gal/A, 1 gal/A, 1.25 gal/A, 1.5 gal/A, or 2 gal/A.

In some embodiments, the harvesting is done 5-20 weeks, 10-15 weeks, 10-14 weeks, 11 weeks, 12 weeks, 13 weeks, or 14 weeks after the step of applying.

In some embodiments, the potatoes are Yukon Gold, Kennebec, Red Pontiac, Shepody, Russet Burbank, Atlantic, Red Lasota, Sifra, Prospect, or Goldrush.

In some embodiments, the bioprotection from *Streptomyces scabies* infection is determined based on average surface areas affected by *Streptomyces scabies*. In some embodiments, the bioprotection from *Streptomyces scabies* infection is determined based on potato yields. In some embodiments, the bioprotection from *Streptomyces scabies* infection is determined based on a cull rate.

In a different aspect, the present invention provides a composition for treatment of *Streptomyces scabies*, comprising: an effective amount of Micrococcin P1; and an agriculturally acceptable carrier, wherein the effective amount is sufficient for bioprotection of potatoes from *Streptomyces scabies* infection, wherein the bioprotection of potatoes is assessed at the time of harvesting the potatoes from a soil treated with the composition.

In some embodiments, the agriculturally acceptable carrier is selected from the group consisting of a culture medium, a filtered fraction of a culture medium, or a filtered fraction of a microbial culture.

In some embodiments, the agriculturally acceptable carrier comprises a culture medium inoculated with *Bacillus pumilus*. In some embodiments, the culture medium is bottled. In some embodiments, the culture medium is incubated with *Bacillus pumilus* for 3-20 days, 5-15 days, 5-10 days, 6-8 days or 7 days before being bottled. In some embodiments, the culture medium is incubated with *Bacillus pumilus* at 25-37° C., 28-35° C., 28-32° C. or 30° C. before being bottled.

In some embodiments, the composition further comprises *Bacillus subtilis*.

In some embodiments, the composition further comprises a filtered fraction of a microbial culture. In some embodiments, the composition does not comprise a filtered fraction of a microbial culture.

In some embodiments, the microbial culture comprises *Lactobacillus paracasei, Lactobacillus helveticus, Lactobacillus plantarum, Lactobacillus rhamnosus, Lactococcus lactis, Bacillus amyololiquefaciens, Aspergillus oryzae, Saccharomyces cerevisiae, Candida utilis*, and *Rhodopseudomonas palustris*. In some embodiments, the microbial culture is produced by incubating IN-M1, deposited under ATCC Accession No. PTA-12383, or IN-M2, deposited under ATCC Accession No. PTA-121556.

In some embodiments, the effective amount of Micrococcin P1 is determined based on average surface area of potatoes affected by *Streptomyces scabies*. In some embodiments, the effective amount of Micrococcin P1 is determined based on potato yields. In some embodiments, the effective amount of Micrococcin P1 is determined based on a cull rate. In some embodiments, the effective amount of Micrococcin P1 is above 1 ng/L, 10 ng/L, 20 ng/L, 50 ng/L, 100 ng/L, 200 ng/L, 500 ng/L, 1 mg/L, 10 mg/L, 50 mg/L, 100 mg/L or 500 mg/L.

In some embodiments, the composition further comprises copper or a copper alloy.

In yet anther aspect, the present invention provides a method of protecting potatoes from *Streptomyces scabies*, comprising the step of: applying an effective amount of the composition of the present invention to a soil, the soil exposed to *Streptomyces scabies*, wherein the effective amount is sufficient for bioprotection of the potatoes from *Streptomyces scabies*, wherein the bioprotection of the potatoes is assessed at the time of harvesting the potatoes from the soil.

3. BRIEF DESCRIPTION OF THE DRAWINGS

FIG. 1A provides a picture of PDA lawn of *Streptomyces scabies* spotted with a drop of *Bacillus pumilus* culture. FIG. 1B provides a picture of PDA lawn of *Streptomyces scabies* spotted with a drop of crude extract from *Bacillus pumilus* (top), *Bacillus pumilus* (right), *Bacillus subtilis* (left) and control (bottom).

FIG. 2A provides HPLC chromatogram of purified extract from *Bacillus pumilus* culture with RT 8.140 min. FIG. 2B provides HPLC chromatogram of standard Micrococcin P1 with RT 8.115 min.

FIG. 3A provides LC-MS chromatogram of purified Micrococcin P1, with various adducts, from *Bacillus pumilus* culture. FIG. 3B provides LC-MS chromatogram of standard Micrococcin P1 with various adducts.

FIG. 4A provides ESI-MS spectrum of purified extract from *Bacillus pumilus* culture. FIG. 4B provides ESI-MS spectrum of standard Micrococcin P1.

FIG. 5 provides the chemical structure of Micrococcin P1.

FIG. 6 illustrates the experimental procedure for testing sporicidal activity of the purified extract from *Bacillus pumilus* against *Streptomyces scabies* spores.

FIG. 7 provides antibacterial activities of Micrococcin P1 against *Streptomyces scabies* at various concentrations.

FIG. 8 provides experimental results demonstrating suppressive effects of *Bacillus subtilis* ("*B. subtilis*"), *Bacillus pumilus* ("*B. pumilus*"), *Bacillus subtilis* and *Bacillus pumilus* together ("Mix") or control ("*S. scabies*") on common scab disease caused by *Streptomyces scabies* in Kennebec potato in a pot. Data are provided using a disease scale based on disease severity observed on potato tubers (0=0%, 1=10%, 2=20%, 3=30%, 4=40%, 5=>50%).

FIG. 9 provides experimental results demonstrating suppressive effects of *Bacillus subtilis* ("*B. subtilis*"), *Bacillus pumilus* ("*B. pumilus*"), *Bacillus subtilis* and *Bacillus pumilus* together ("Mix") or control ("*S. scabies*") on common scab disease caused by *Streptomyces scabies* in Yukon Gold potato in a pot. Data are provided using a disease scale based on disease severity observed on potato tubers (0=0%, 1=10%, 2=20%, 3=30%, 4=40%, 5=>50%).

FIGS. 10A-10D provide pictures of potato harvested from a soil treated with *Streptomyces scabies* alone (FIG. 10A), *Streptomyces scabies, Bacillus pumilus* and *Bacillus subtilis* (FIG. 10B), *Streptomyces scabies* and *Bacillus pumilus* (FIG. 10C), or *Streptomyces scabies* and *Bacillus subtilis* (FIG. 10D).

Figure 11A:
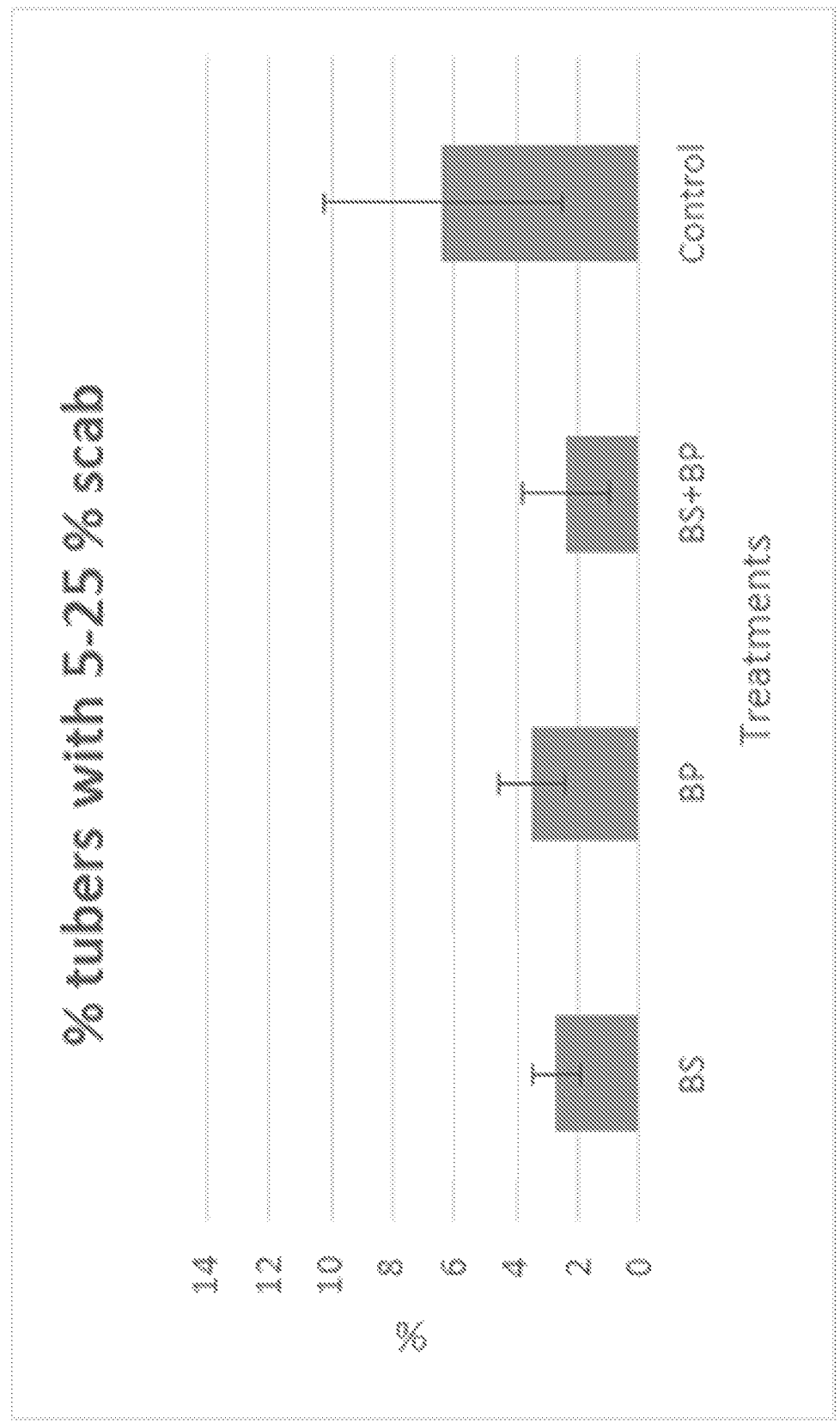
Figure 11B:
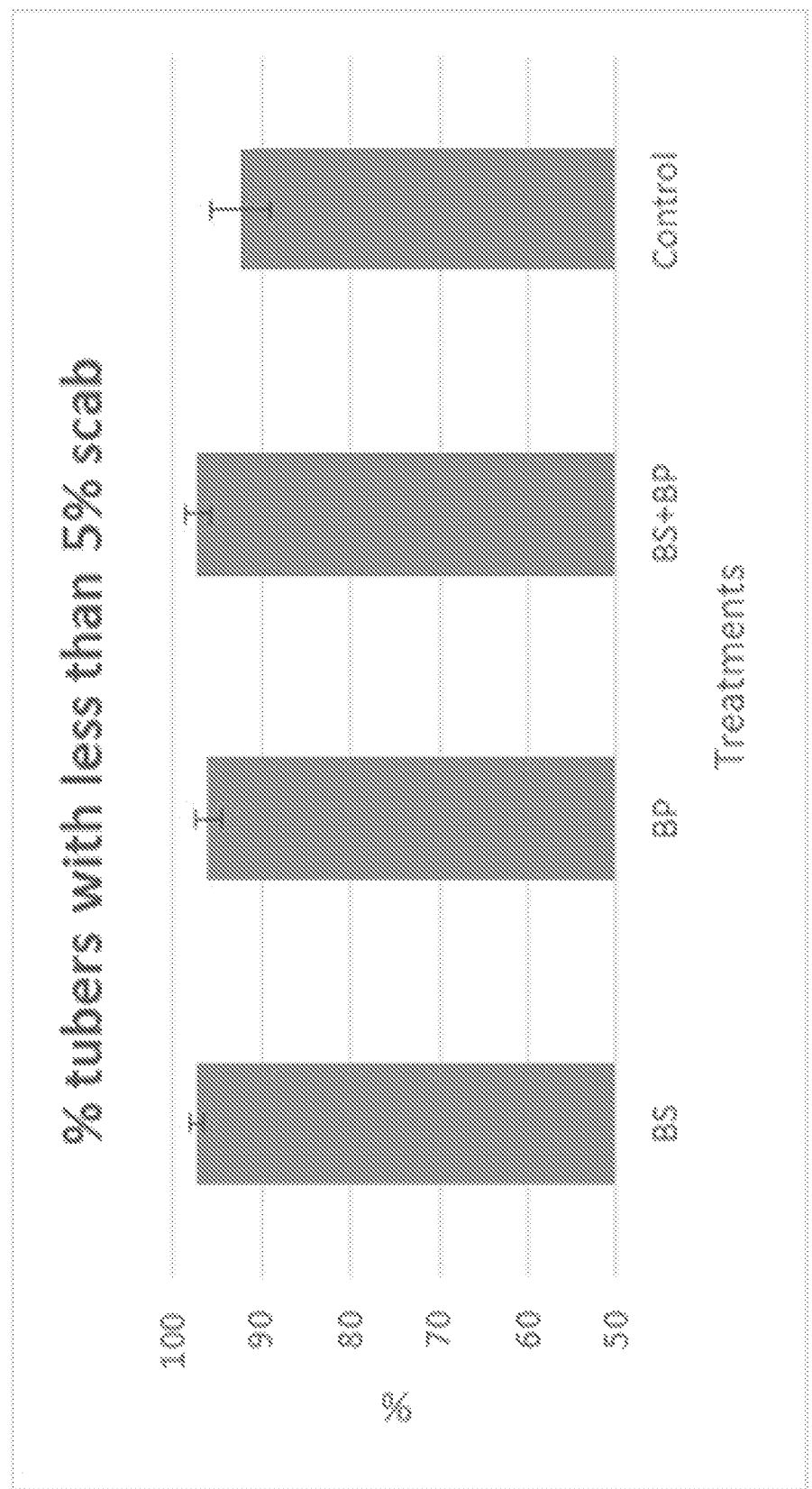

FIG. 11A provides percentages of potato tubers with 5-25% of scab lesions from soils treated with *Bacillus subtilis* alone ("BS"), *Bacillus pumilus* alone ("BP"), *Bacillus subtilis* together with *Bacillus pumilus* ("BS+BP") or control ("Control") in Site 1 of the field experiment. FIG. 11B provides percentages of potato tubers with less than 5% of the potato surface area having scab lesions, harvested from soils treated with *Bacillus subtilis* alone ("BS"), *Bacillus pumilus* alone ("BP"), *Bacillus subtilis* together with *Bacillus pumilus* ("BS+BP") or control ("Control") in Site 1 of the field experiment.

Figure 12A:
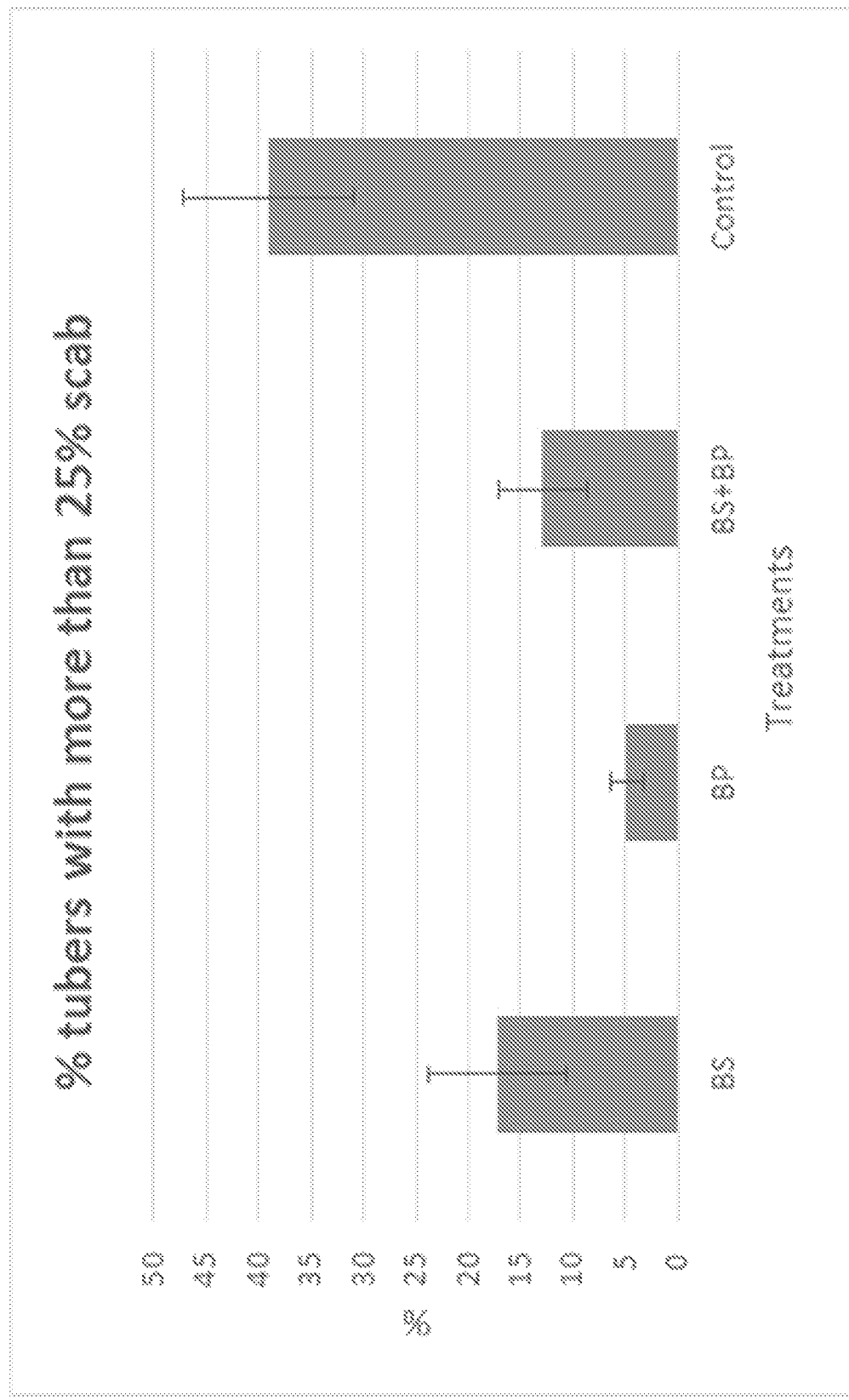
Figure 12B:
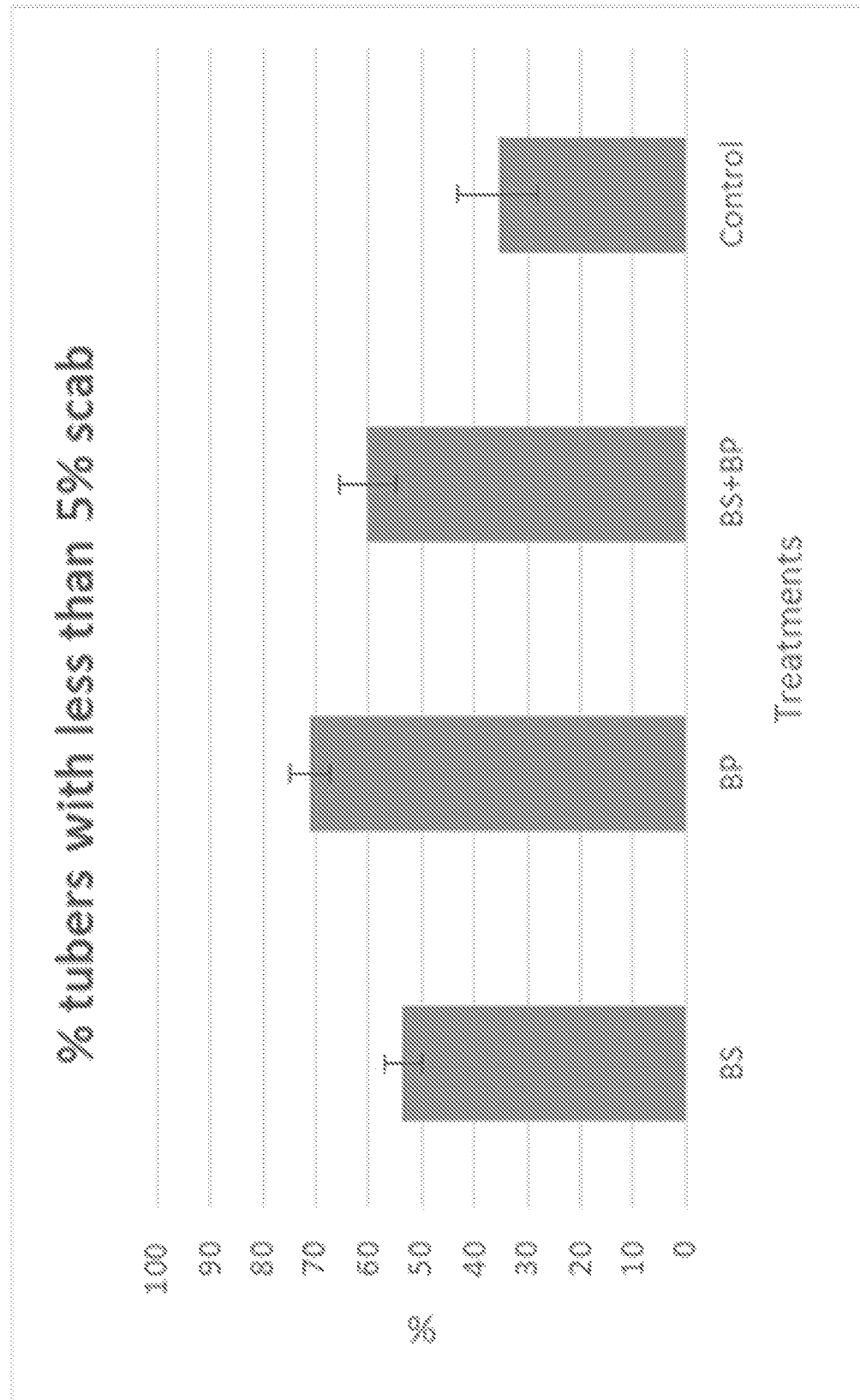

FIG. 12A provides percentages of potato tubers with more than 25% of the potato surface area having scab lesions, harvested from soils treated with *Bacillus subtilis* alone ("BS"), *Bacillus pumilus* alone ("BP"), *Bacillus subtilis* together with *Bacillus pumilus* ("BS+BP") or control ("Control") in Site 2 of the field experiment. FIG. 12B provides percentages of potato tubers with less than 5% of the potato surface area having scab lesions, harvested from soils treated with *Bacillus subtilis* alone ("BS"), *Bacillus pumilus* alone ("BP"), *Bacillus subtilis* together with *Bacillus pumilus* ("BS+BP") or control ("Control") in Site 2 of the field experiment.

Figure 13A:
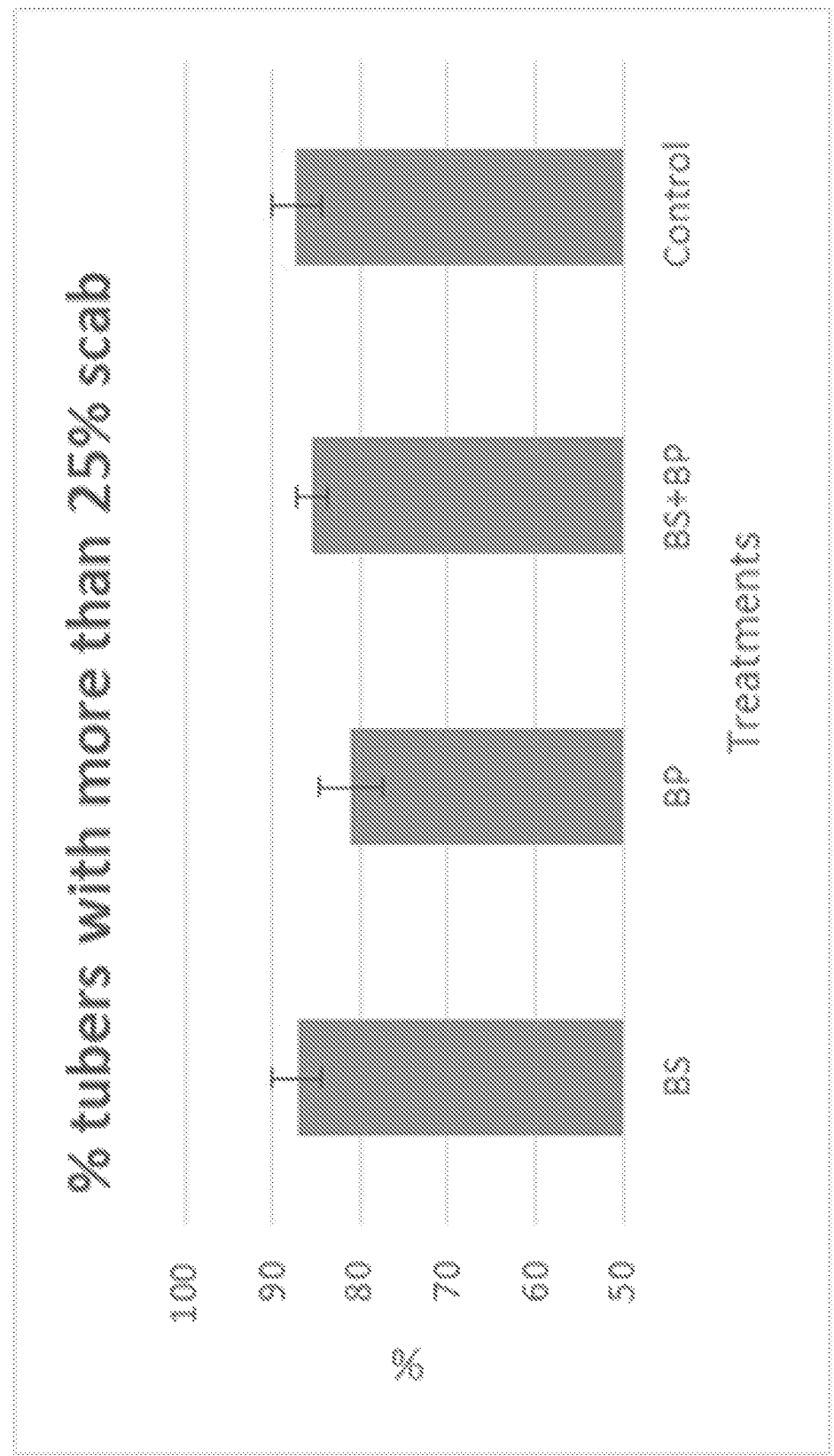
Figure 13B:
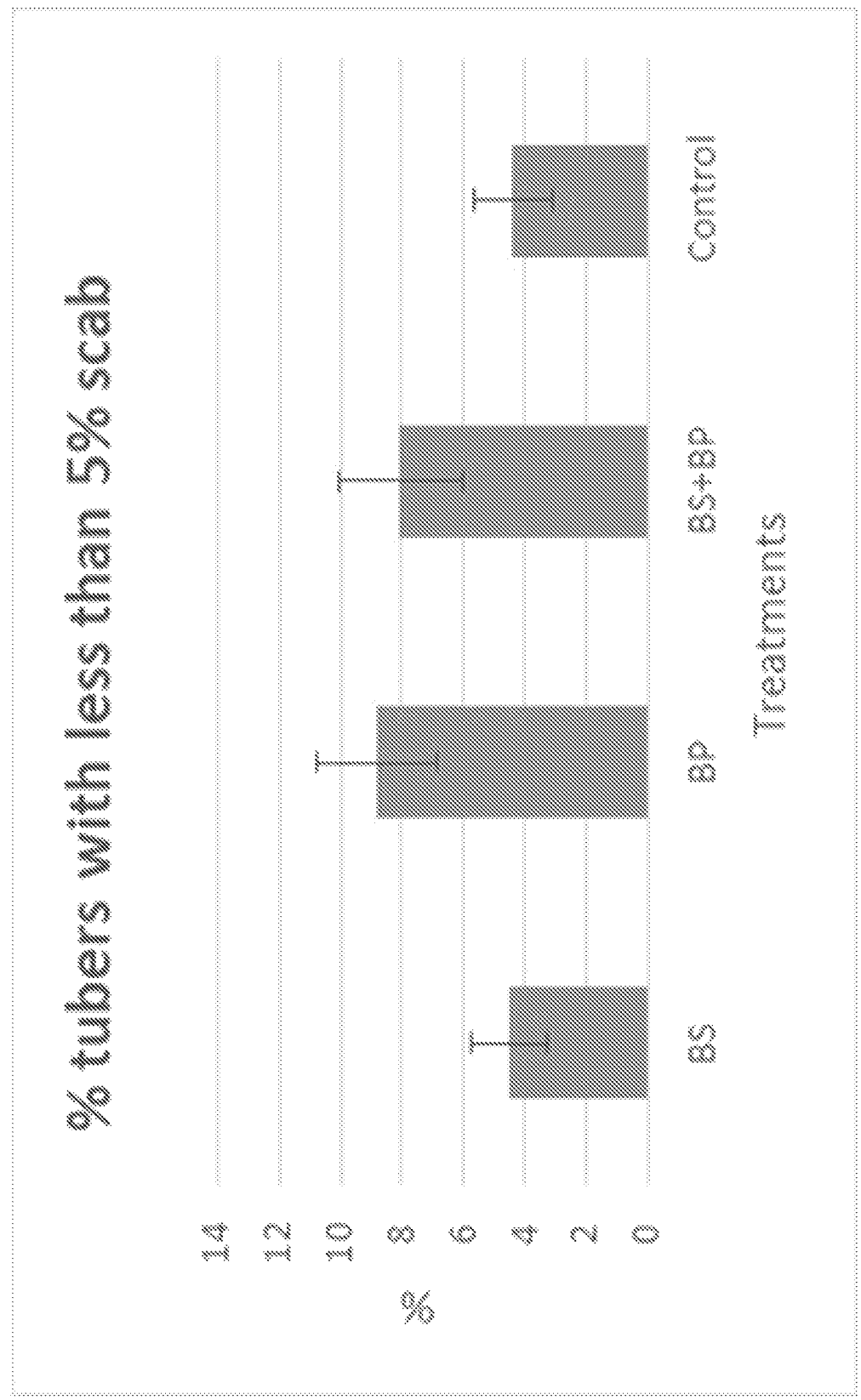

FIG. 13A provides percentages of potato tubers with more than 25% of the potato surface area having scab lesions, harvested from soils treated with *Bacillus subtilis* alone ("BS"), *Bacillus pumilus* alone ("BP"), *Bacillus subtilis* together with *Bacillus pumilus* ("BS+BP") or control ("Control") in Site 3 of the field experiment. FIG. 13B provides percentages of potato tubers with less than 5% of the potato surface area having scab lesions, harvested from soils treated with *Bacillus subtilis* alone ("BS"), *Bacillus pumilus* alone ("BP"), *Bacillus subtilis* together with *Bacillus pumilus* ("BS+BP") or control ("Control") in Site 3 of the field experiment.

Figure 14A:
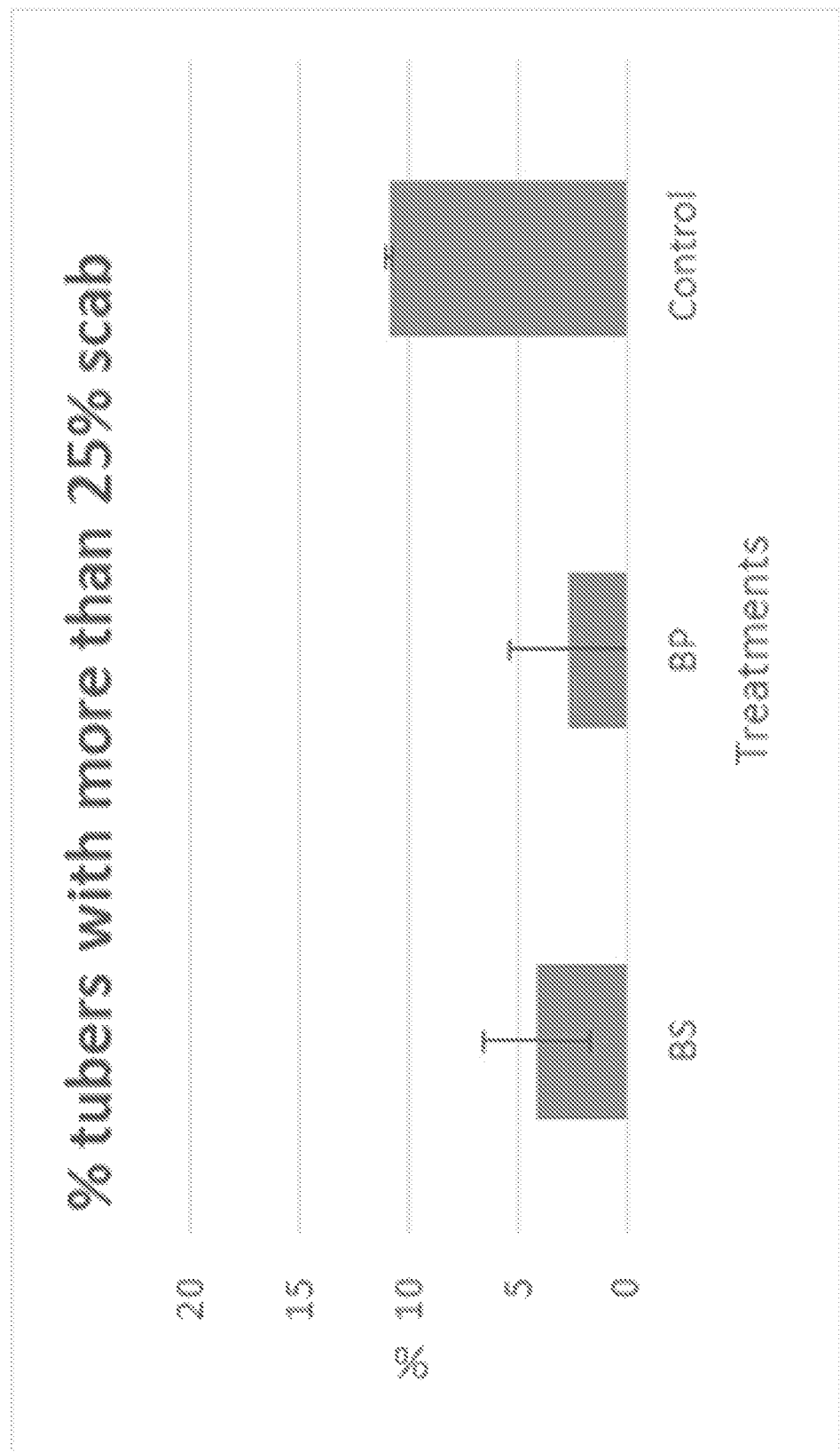
Figure 14B:
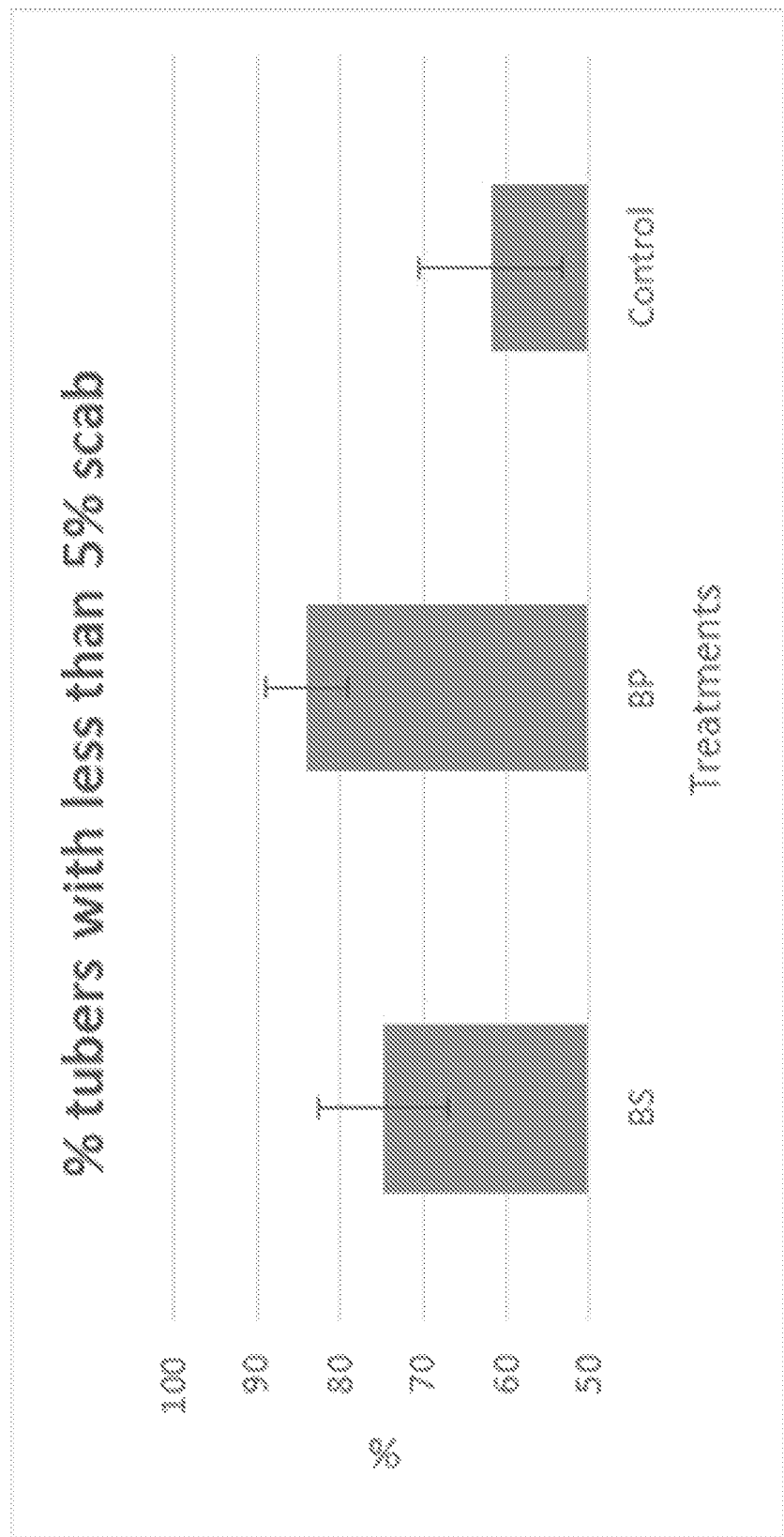

FIG. 14A provides percentages of potato tubers with more than 25% of the potato surface area having scab lesions, harvested from soils treated with *Bacillus subtilis* alone ("BS"), *Bacillus pumilus* alone ("BP"), or control ("Control") in Site 4 of the field experiment. FIG. 14B provides percentages of potato tubers with less than 5% of the potato surface area having scab lesions, harvested from soils treated with *Bacillus subtilis* alone ("BS"), *Bacillus pumilus* alone ("BP") or control ("Control") in Site 4 of the field experiment.

Figure 15A:
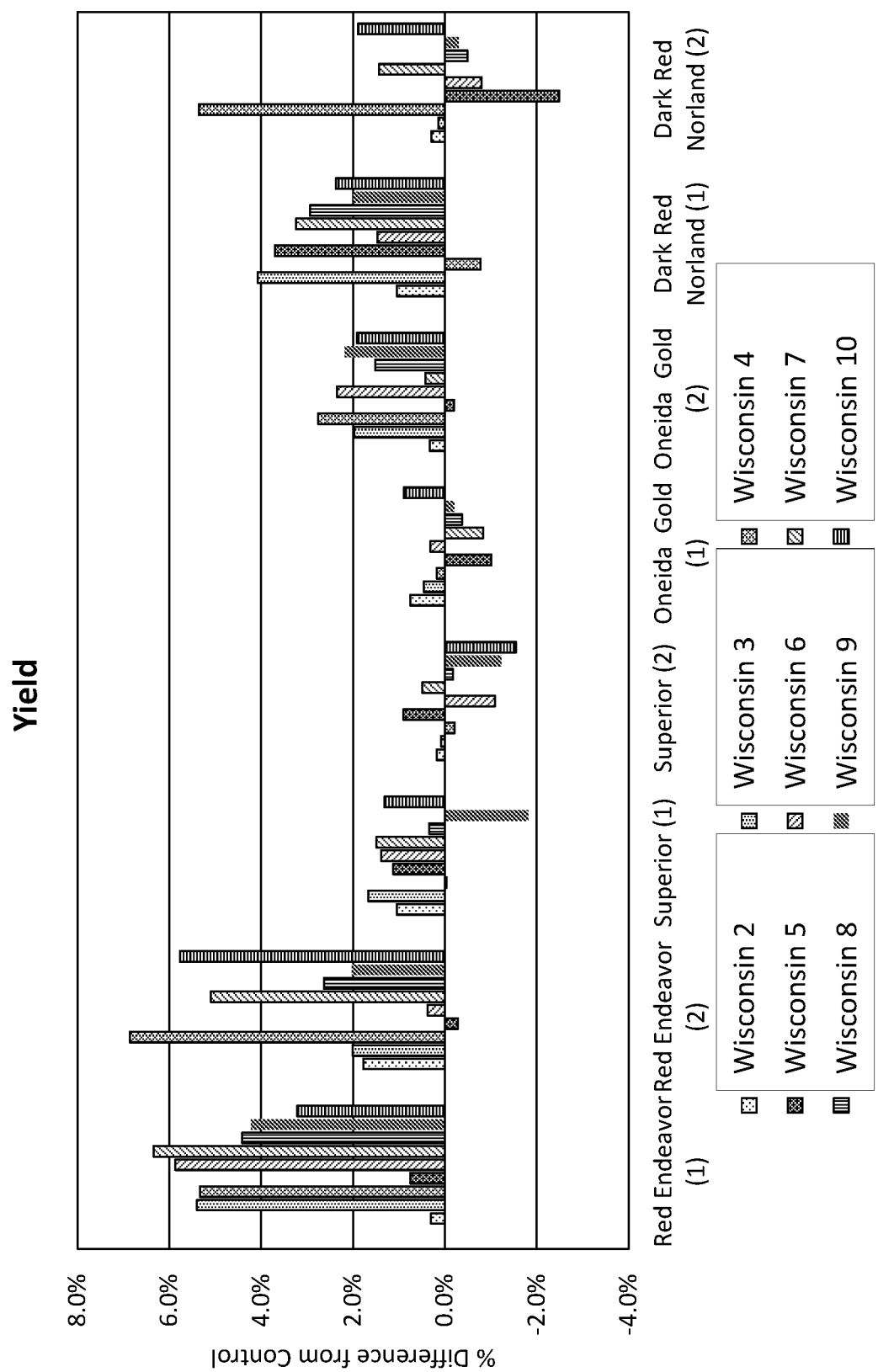
Figure 15B:
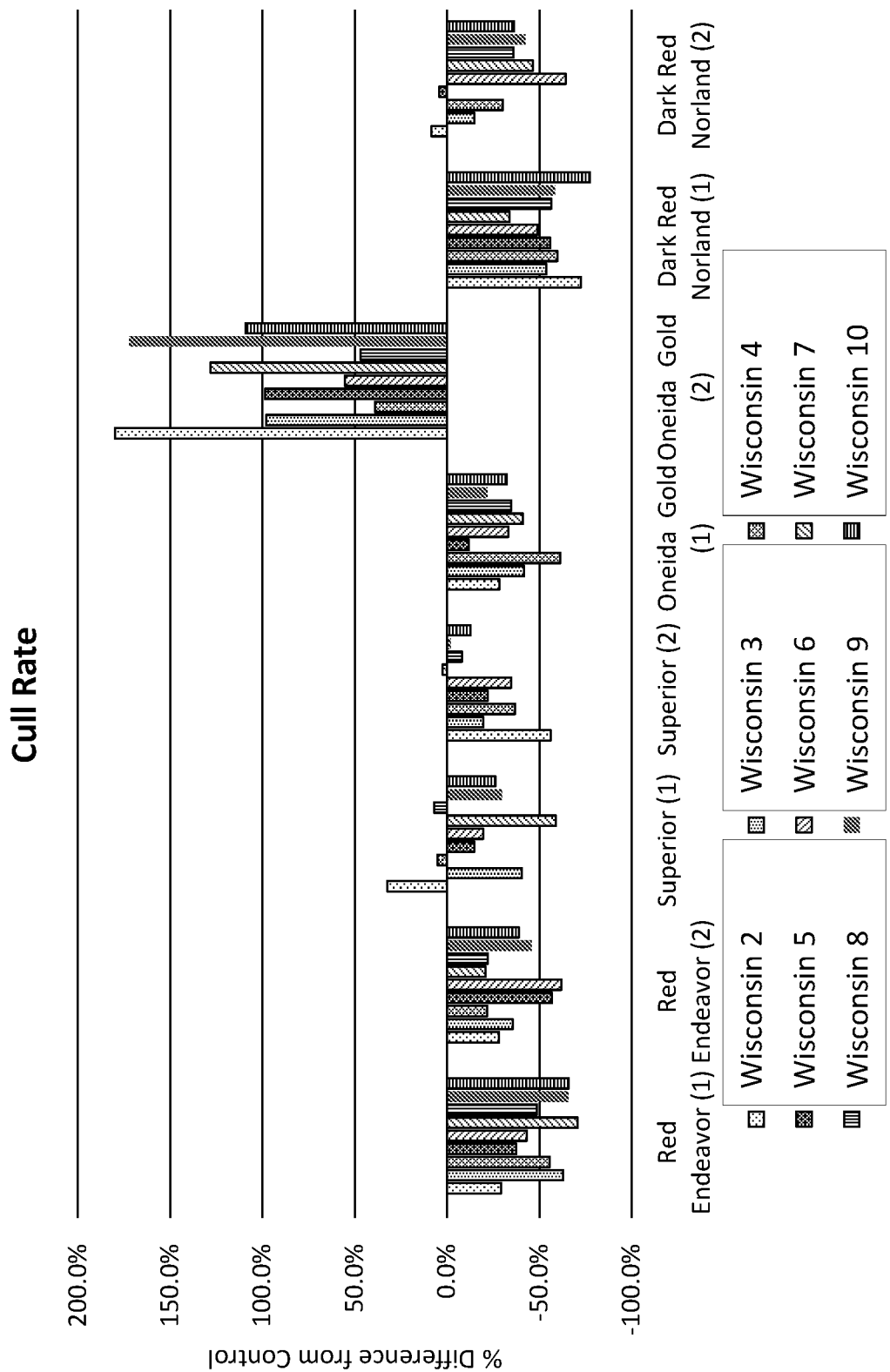
Figure 15C:
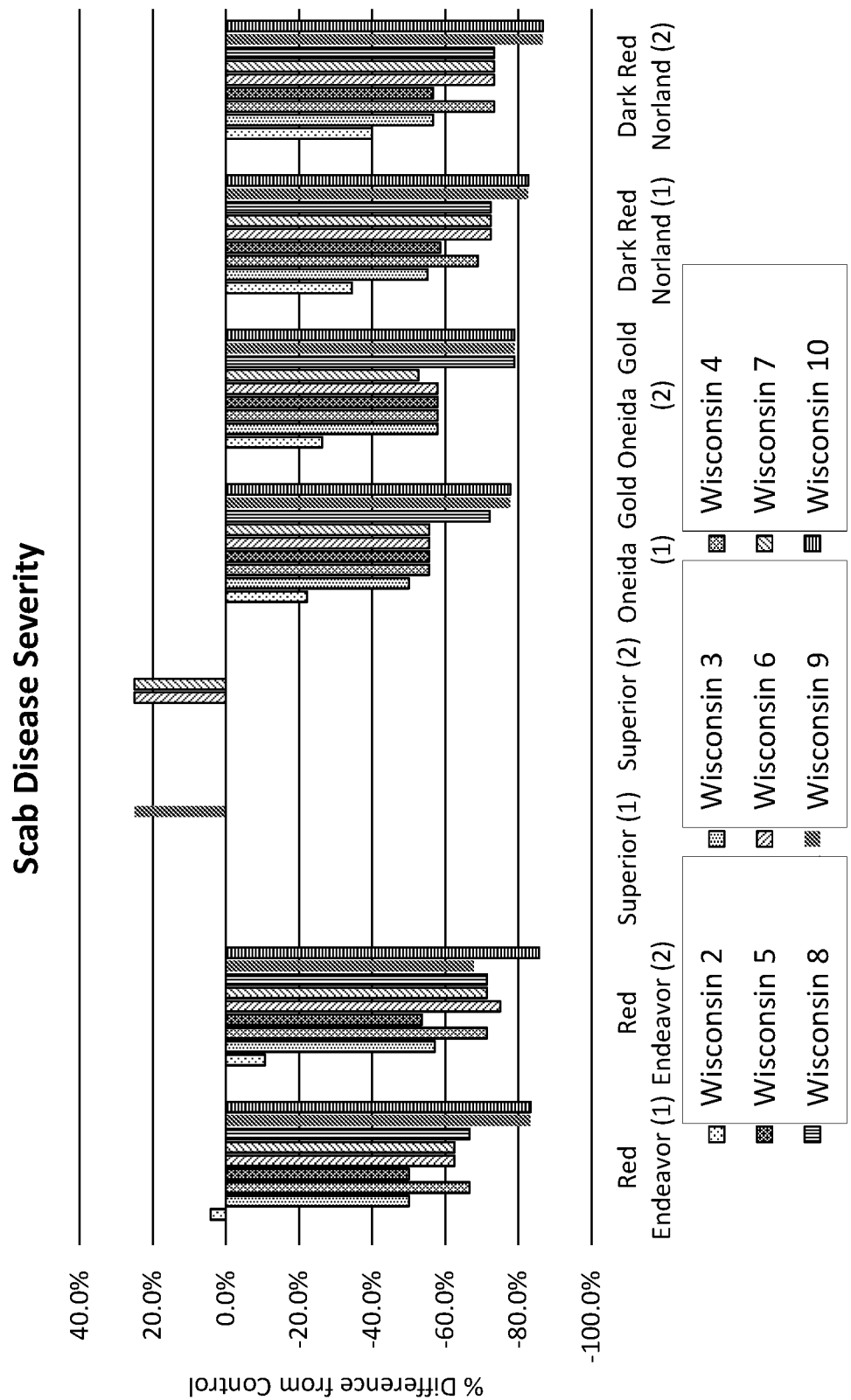

FIG. 15A provides percentage yield differences between potatoes from soils treated with various products of *Bacillus subtilis*, *Bacillus pumilus* or both, and a control (data also provided in TABLE 7). FIG. 15B provides percentage cull rate differences between potatoes treated with various products of *Bacillus subtilis*, *Bacillus pumilus* or both, and a control (data also provided in TABLE 8). FIG. 15C provides percentage differences of scab disease severity between potatoes treated with various products of *Bacillus subtilis*, *Bacillus pumilus* or both, and a control (TABLE also provided in TABLE 9).

Figure 16:
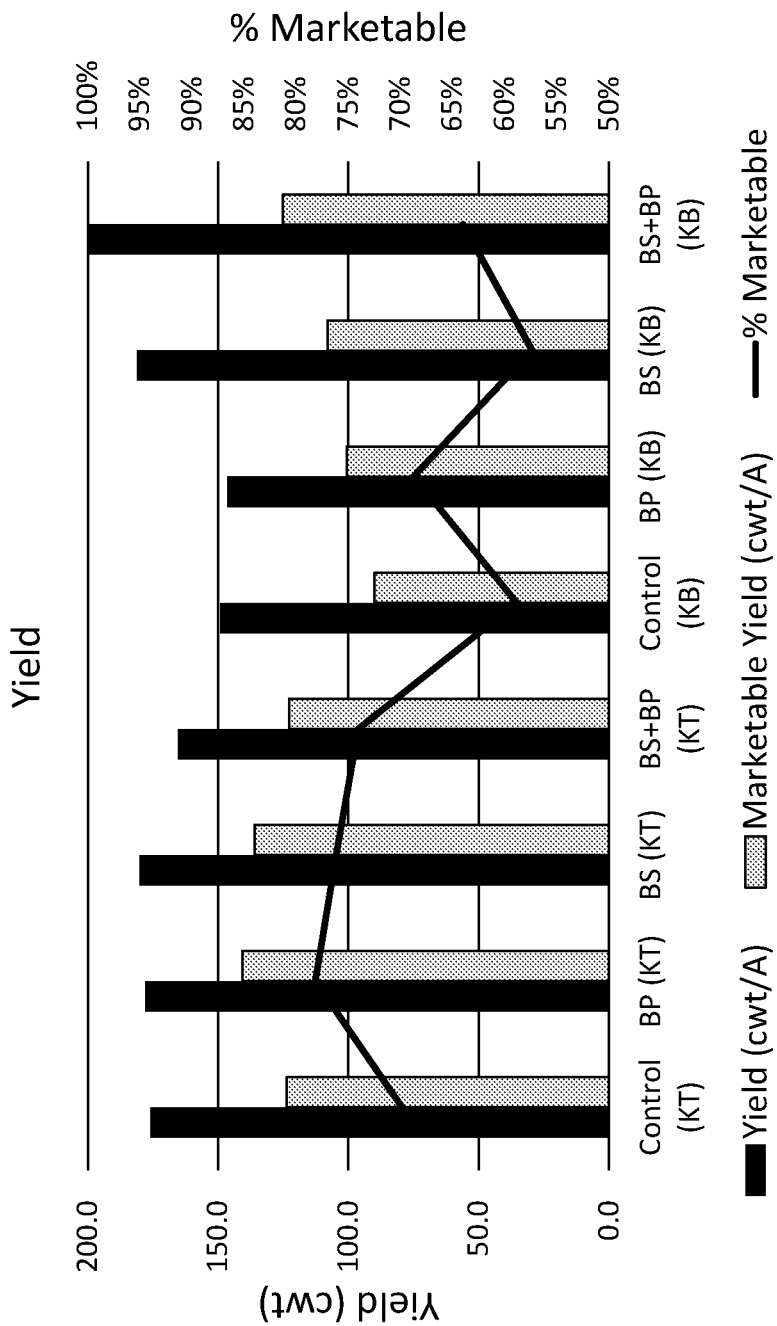

FIG. 16 provides yields of potatoes (cwt/A) from fields treated with various products of *Bacillus subtilis*, *Bacillus pumilus* or both, or a control (black bars); marketable yields of potatoes (cwt/A) from fields treated with various products of *Bacillus subtilis*, *Bacillus pumilus* or both, or a control (grey bars); and percentage marketable yields of potatoes (%) from fields treated with various products of *Bacillus subtilis*, *Bacillus pumilus* or both, or a control (grey line).

The figures depict various embodiments of the present invention for purposes of illustration only. One skilled in the art will readily recognize from the following discussion that alternative embodiments of the structures and methods illustrated herein may be employed without departing from the principles of the invention described herein.

4. DETAILED DESCRIPTION

4.1. Definitions

Unless defined otherwise, all technical and scientific terms used herein have the meaning commonly understood by a person skilled in the art to which this invention belongs. As used herein, the following terms have the meanings ascribed to them below.

The term "microorganism" as used herein includes, but is not limited to, bacteria, viruses, fungi, algae, yeasts, protozoa, worms, spirochetes, single-celled, and multi-celled organisms that are included in classification schema as prokaryotes, eukaryotes, Archea, and Bacteria, and those that are known to those skilled in the art.

The term "antimicrobial" as used herein refers to an efficacy or activity (i.e., of an agent or extract) that reduces or eliminates the (relative) number of active microorganisms or reduces the pathological results of a microbial infection. An "antimicrobial agent," as used herein, refers to a bioprotectant agent that prevents or reduces in vitro and/or in vivo infections or damages of a plant caused by a pathogenic microorganism. The antimicrobial agent includes, but is not limited to, an antibacterial agent, antiviral agent, and antifungal agent.

The term "carrier" as used herein refers to an "agriculturally acceptable carrier." An "agriculturally acceptable carrier" is intended to refer to any material which can be used to deliver a microbial composition as described herein, agriculturally beneficial ingredient(s), biologically active ingredient(s), etc., to a plant, a plant part (e.g., a seed), or a soil, and preferably which carrier can be added (to the plant, plant part (e.g., seed), or soil) without having an adverse effect on plant growth, soil structure, soil drainage or the like.

The term "effective amount" as used herein refers to a dose or amount that produces the desired effect for which it is used. In the context of the present methods, an effective amount is an amount effective for bioprotection by its antimicrobial activity.

The term "sufficient amount" as used herein refers to an amount sufficient to produce a desired effect. Specifically, the term "effective amount sufficient bioprotection from *Streptomyces scabies*" as used herein refers to a dose or amount that is sufficient for bioprotection from pathological symptoms associated with *Streptomyces scabies* infection.

The term "pathological symptom associated with *Streptomyces scabies*" as used herein refers to various symptoms detected in potatoes infected with *Streptomyces scabies*. The symptoms include, but not limited to, symptoms on the surface of potatoes including erumpent, russet, and pitted lesions. Erumpent lesions are raised lesions, russet lesions are defined as superficial corky tissue that covers large areas of the tuber surface and pitted lesions are dark colored sunken areas up to in deep. Scab lesions can occur anywhere on the tuber surface and more than one type of lesion may be present on a single tuber. Scab can affect young tubers with the lesions expanding as the tuber matures. The symptoms further include decrease of the growth of the seedlings. The pathological symptoms associated with *Streptomyces scabies* can be measured by various methods known in the art, for example, based on the areas of scab regions on the potato surface, incidence of scab lesions on potato tubers, decrease of total yields or marketable yields, increase of a culling rate, etc.

The term "bioprotection" as used herein refers to the enhancement of resistance of a plant to pathological actions by one or more microbial organisms, and such protection is compared to a similar, control plant not treated with a bioprotectant composition disclosed herein, otherwise situated in similar environment. Bioprotection can include reduction of plant damage due to plant pathogens. Such bioprotection may include an antimicrobial response by a plant, in which the enhanced antimicrobial response may be due to enhanced activities or response by the plant to resist one or more microorganisms or the bioprotection may be due to actions by components of compositions applied to the plant against one or more microorganisms. In a particular context, bioprotection refers to processes that improve the antimicrobial activity or response of plants, e.g., plants to which a bioprotectant is applied. Bioprotectant compositions may be delivered via a soil amendment(s). Such compositions, when provided to plants, by any method including as a soil amendment, may provide microoganisms as part of a consortium to reside on or in the plant as an endophyte or epiphyte.

The term "bioprotectant(s)" as used herein refers to any composition capable of enhancing the antimicrobial activity of a plant, antinematocidal activity of a plant, a reduction in pathological symptoms or lesions resulting from actions of a plant pathogen, compared to an untreated control plant otherwise situated similar environment. Unless clearly stated otherwise, a bioprotectant may be comprised of a single ingredient or a combination of several different ingredients, and the enhanced antimicrobial activity may be attributed to one or more of the ingredients, either acting independently or in combination.

The term "strain" refers in general to a closed population of organisms of the same species. Accordingly, the term "strain of lactic acid bacteria" generally refers to a strain of a species of lactic acid bacteria. More particularly, the term "strain" refers to members of a microbial species, wherein such members, i.e., strains, have different genotypes and/or phenotypes. Herein, the term "genotype" encompasses both the genomic and the recombinant DNA content of a microorganism and the microorganism's proteomic and/or metabolomic profile and post translational modifications thereof. Herein, the term "phenotype" refers to observable physical characteristics dependent upon the genetic constitution of a microorganism. As one skilled in the art would recognize, microbial strains are thus composed of individual microbial cells having a common genotype and/or phenotype. Further, individual microbial cells may have specific characteristics (e.g., a specific rep-PCR pattern) which may identify them as belonging to their particular strain. A microbial strain can comprise one or more isolates of a microorganism.

The term "soil exposed to *Streptomyces scabies*" as used herein refers to a soil (1) where a plant previously rooted therein showed a pathological symptom associated with *Streptomyces scabies*, (2) where a plant currently rooted therein shows a pathological symptom associated with *Streptomyces scabies*, or (3) where a potato which will be planted therein without any antimicrobial treatment is expected to show a pathological symptom associated with *Streptomyces scabies*.

4.2. Other Interpretational Conventions

Ranges recited herein are understood to be shorthand for all of the values within the range, inclusive of the recited endpoints. For example, a range of 1 to 50 is understood to include any number, combination of numbers, or sub-range from the group consisting of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50.

Unless otherwise indicated, reference to a compound that has one or more stereocenters intends each stereoisomer, and all combinations of stereoisomers, thereof.

4.3. Antimicrobial Compositions for Bioprotection of Potatoes from *Streptomyces scabies*

In a first aspect, compositions are presented for protecting potatoes from *Streptomyces scabies*. In some embodiments, the compositions comprise a bacterial culture comprising one or more *Bacillus* strain, such as *Bacillus pumilus* and *Bacillus subtilis*, demonstrated to be effective in inhibiting activity of *Streptomyces scabies*. The compositions can comprise *Bacillus pumilus*, *Bacillus subtilis*, or both *Bacillus pumilus* and *Bacillus subtilis*. In some embodiments, the compositions comprise a bacterial culture of *Bacillus pumilus*, a bacterial culture of *Bacillus subtilis*, or a bacterial culture of both *Bacillus pumilus* and *Bacillus subtilis*.

In some embodiments, the compositions comprise crude extracts from the *Bacillus* strain. Specifically, the composition can comprise crude extracts from *Bacillus pumilus* or *Bacillus subtilis*. In some embodiments, the composition comprises crude extracts from both *Bacillus pumilus* and *Bacillus subtilis*. In some embodiments, the composition comprises a purified fraction of crude extracts from *Bacillus pumilus*, *Bacillus subtilis*, or both.

In some embodiments, the compositions comprise Micrococcin P1 as an active component. In some embodiments, Micrococcin P1 is produced from bacteria. In other embodiments, chemically synthesized Micrococcin P1 is used.

In some embodiments, the compositions further comprise an agriculturally acceptable carrier. In some embodiments, the compositions comprise a cell-free supernatant of a microbial culture as an agriculturally acceptable carrier.

4.3.1. Active Components 4.3.1.1. *Bacillus pumilus*

In some embodiments, the compositions for bioprotection of potatoes from *Streptomyces scabies* comprise a bacterial culture comprising *Bacillus pumilus*. The bacterial culture comprising *Bacillus pumilus* can be obtained by inoculating and culturing *Bacillus pumilus*.

*Bacillus pumilus* used in various embodiments of the present invention can be a bacterial strain identified to have at least 95%, 96%, 97%, 98%, 99%, 99.5%, 99.8%, 99.9% or 100% identity to the 16S rRNA sequence of SEQ ID NO: 4. In some embodiments, *Bacillus pumilus* strain NES-CAP-1 (GenBank Accession No. MF079281.1) is used.

*Bacillus pumilus* used in various embodiments of the present invention can be a bacterial strain identified to have at least 95%, 96%, 97%, 98%, 99%, 99.5%, 99.8%, 99.9% or 100% identity to "*Bacillus pumilus*" by API test.

*Bacillus pumilus* used in various embodiments of the present invention can be a *Bacillus pumilus* strain identified to express Micrococcin P1. Expression of Micrococcin P1 can be tested using various methods known in the art, such as liquid chromatography, HPLC, mass spectrum. In some embodiments, *Bacillus pumilus* is selected based on its expression level of Micrococcin P1.

In some embodiments, *Bacillus pumilus* is selected based on its capability to suppress activity or growth of *Streptomyces scabies* on an agar plate. In some embodiments, *Bacillus pumilus* is selected based on the capability of its extract to suppress activity or growth of *Streptomyces scabies* on an agar plate. In some embodiments, *Bacillus pumilus* is selected based on its capability to protect a potato from *Streptomyces scabies* in a pot. In some embodiments, *Bacillus pumilus* is selected based on its capability to protect a potato from *Streptomyces scabies* in a field.

The capability to protect a potato from *Streptomyces scabies* can be determined by comparing damages of potatoes associated with *Streptomyces scabies* with and without treatment with *Bacillus pumilus*. The capability to protect a potato from *Streptomyces scabies* can be determined by comparing average surface areas on a potato affected by *Streptomyces scabies* with and without treatment with *Bacillus pumilus*. The capability to protect a potato from *Streptomyces scabies* can be determined by comparing percentage of surface areas having scab lesions on a potato with and without treatment with *Bacillus pumilus*. The capability to protect a potato from *Streptomyces scabies* can be determined by comparing potato yields with and without treatment with *Bacillus pumilus*. The capability to protect a potato from *Streptomyces scabies* can be determined by comparing a cull rate with and without treatment with *Bacillus pumilus*.

In some embodiments, *Bacillus pumilus* strain is selected when it can reduce damages associated with *Streptomyces scabies* by at least 10%, 20%, 30%, 40%, 50%, 60%, 70%, 80%, 90%, 95% in the pot experiment, or in the field experiment.

In some embodiments, the bacterial culture comprising *Bacillus pumilus* is obtained by inoculating *Bacillus pumilus* into a culture medium. The culture medium can be an LB broth or other culture medium available in the art.

In some embodiments, the culture medium inoculated with *Bacillus pumilus* can be incubated for 1 day, 2 days, 3-30 days, 3-20 days, 5-15 days, 5-10 days, 6-8 days or 7 days before being bottled. In some embodiments, the culture medium inoculated with *Bacillus pumilus* can be incubated at 20-37° C., 25-37° C., 28-35° C., 28-32° C. or 30° C.

In some embodiments, the *Bacillus* strain is selected for its capability to generate a zone of inhibition with a diameter larger than 2 mm when 1 μL, 2 μL, 3 μL, 4 μL, 5 μL, 6 μL, 7 μL, 8 μL, 9 μL 10 μL, 10-20 μL, 20-30 μL, 30-40 μL, 40-50 μL, 50-100 μL, 100-500 μL, 500-1000 μL of the bacterial culture is applied. In some embodiments, the zone of inhibition has a diameter larger than 3 mm, larger than 4 mm, larger than 5 mm, larger than 6 mm, larger than 7 mm, larger than 8 mm, larger than 9 mm, larger than 1 cm, or larger than 1.5 cm, when measured after incubation. The diameter can be measured 1 day, 2 days, 3 days, 3-7 days, or 5-10 days after application of the bacterial culture.

In some embodiments, the *Bacillus* strain is selected for its capability to generate a zone of inhibition with a diameter larger than 2 mm when 1 μL, 2 μL, 3 μL, 4 μL, 5 μL, 6 μL, 7 μL, 8 μL, 9 μL 10 μL, 10-20 μL, 20-30 μL, 30-40 μL, 40-50 μL, or 50-100 μL of the crude extract from the bacterial culture is applied. In some embodiments, the zone of inhibition has a diameter larger than 3 mm, larger than 4 mm, larger than 5 mm, larger than 6 mm, larger than 7 mm, larger than 8 mm, larger than 9 mm, larger than 1 cm, or larger than 1.5 cm, when measured after incubation. The diameter can be measured 1 day, 2 days, 3 days, 3-7 days, or 5-10 days of incubation after application of the crude extract.

In some embodiments, the composition comprises a strain of *Bacillus pumilus* ("*Bacillus pumilus* strain ITI-1" or "ITI-1") deposited with the Americal Type Culture Collection (ATCC), with the ATCC® Patent Designation No. of PTA-125304, under the Budapest Treaty on Sep. 26, 2018, under ATCC Account No. 200139.

4.3.1.2. *Bacillus subtilis*

In some embodiments, the compositions for bioprotection of potatoes from *Streptomyces scabies* comprise a bacterial culture comprising *Bacillus subtilis*. The bacterial culture comprising *Bacillus subtilis* can be obtained by inoculating and culturing *Bacillus subtilis*.

*Bacillus subtilis* used in various embodiments of the present invention can be a bacterial strain identified to have at least 95%, 96%, 97%, 98%, 99%, 99.5%, 99.8%, 99.9% or 100% identity to the 16S rRNA sequence of SEQ ID NOS: 5 or 6. In some embodiments, *Bacillus subtilis* strain BSFLG01 (GenBank Accession No. MF196314.1) is used. In some embodiments, *Bacillus subtilis* strain SSL2 (GenBank Accession No. MH192382.1) is used.

*Bacillus subtilis* used in various embodiments of the present invention can be a bacterial strain identified to have at least 95%, 96%, 97%, 98%, 99%, 99.5%, 99.8%, 99.9% or 100% identity to "*Bacillus subtilis*" by API test.

In some embodiments, *Bacillus subtilis* is selected based on its capability to suppress activity or growth of *Streptomyces scabies* on an agar plate. In some embodiments, *Bacillus subtilis* is selected based on the capability of its extract to suppress activity or growth of *Streptomyces scabies* on an agar plate. In some embodiments, *Bacillus subtilis* is selected based on its capability to protect a potato from *Streptomyces scabies* in a pot. In some embodiments, *Bacillus subtilis* is selected based on its capability to protect a potato from *Streptomyces scabies* in a field.

The capability to protect a potato from *Streptomyces scabies* can be determined by comparing damages of potatoes associated with *Streptomyces scabies* with and without treatment with *Bacillus subtilis*. The capability to protect a potato from *Streptomyces scabies* can be determined by comparing average surface areas on a potato affected by *Streptomyces scabies* with and without treatment with *Bacillus subtilis*. The capability to protect a potato from *Streptomyces scabies* can be determined by comparing average surface area with scab lesions on a potato with and without treatment with *Bacillus subtilis*. The capability to protect a potato from *Streptomyces scabies* can be determined by comparing potato yields with and without treatment with *Bacillus subtilis*. The capability to protect a potato from *Streptomyces scabies* can be determined by comparing a cull rate with and without treatment with *Bacillus subtilis*.

In some embodiments, *Bacillus subtilis* strain is selected when it can reduce damages associated with *Streptomyces scabies* by at least 10%, 20%, 30%, 40%, 50%, 60%, 70%, 80%, 90%, 95% in the pot experiment, or in the field experiment.

In some embodiments, the bacterial culture comprising *Bacillus subtilis* is obtained by inoculating *Bacillus subtilis* into a culture medium. The culture medium can be an LB broth or other culture medium available in the art.

In some embodiments, the culture medium inoculated with *Bacillus subtilis* can be incubated for 1 day, 2 days, 3-30 days, 3-20 days, 5-15 days, 5-10 days, 6-8 days or 7 days before being bottled. In some embodiments, the culture medium inoculated with *Bacillus subtilis* can be incubated at 20-37° C., 25-37° C., 28-35° C., 28-32° C. or 30° C.

In some embodiments, the *Bacillus* strain is selected for its capability to generate a zone of inhibition with a diameter larger than 2 mm when 1 µL, 2 µL, 3 µL, 4 µL, 5 µL, 6 µL, 7 µL, 8 µL, 9 µL 10 µL, 10-20 µL, 20-30 µL, 30-40 µL, 40-50 µL, 50-100 µL, 100-500 µL, 500-1000 µL of the bacterial culture is applied. In some embodiments, the zone of inhibition has a diameter larger than 3 mm, larger than 4 mm, larger than 5 mm, larger than 6 mm, larger than 7 mm, larger than 8 mm, larger than 9 mm, larger than 1 cm, or larger than 1.5 cm, when measured after incubation. The diameter can be measured 1 day, 2 days, 3 days, 3-7 days, or 5-10 days after application of the bacterial culture.

In some embodiments, the *Bacillus* strain is selected for its capability to generate a zone of inhibition with a diameter larger than 2 mm when 1 µL, 2 µL, 3 µL, 4 µL, 5 µL, 6 µL, 7 µL, 8 µL, 9 µL 10 µL, 10-20 µL, 20-30 µL, 30-40 µL, 40-50 µL, or 50-100 µL of the crude extract from the bacterial culture is applied. In some embodiments, the zone of inhibition has a diameter larger than 3 mm, larger than 4 mm, larger than 5 mm, larger than 6 mm, larger than 7 mm, larger than 8 mm, larger than 9 mm, larger than 1 cm, or larger than 1.5 cm, when measured after incubation. The diameter can be measured 1 day, 2 days, 3 days, 3-7 days, or 5-10 days of incubation after application of the crude extract.

In some embodiments, the composition comprises a strain of *Bacillus subtilis* ("*Bacillus subtilis* strain ITI-2" or "ITI-2") deposited with the ATCC® Patent Designation No. of PTA-125303 under the Budapest Treaty on Sep. 26, 2018, under ATCC Account No. 200139. In some embodiments, the composition comprises a strain of *Bacillus subtilis* ("*Bacillus subtilis* strain ITI-3" or "ITI-3"), deposited with the ATCC® Patent Designation No. of PTA-125302 under the Budapest Treaty on Sep. 26, 2018, under ATCC Account No. 200139.

4.3.1.3. Micrococcin P1

In some embodiments, the composition of the present invention comprises Micrococcin P1. In some embodiments, Micrococcin P1 is produced by a *Bacillus* strain. The *Bacillus* strain can be selected based on its expression of Micrococcin P1. The *Bacillus* strain can be *Bacillus pumilus*.

In some embodiments, the composition comprises Micrococcin P1 produced by a genetically engineered bacterium. In some embodiments, the bacterium is genetically engineered to produce Micrococcin P1 by delivering one or more genes involved in the biosynthesis of Micrococcin P1. In some embodiments, the bacterium is genetically engineered by using the method described in Philip R. Bennallack et al., Reconstitution and Minimization of a Micrococcin Biosynthetic Pathway in *Bacillus subtilis*, Journal of Bacteriology (2016), incorporated by reference in its entirety herein.

In some cases, the composition comprises Micrococcin P1 by comprising bacteria capable of expressing Micrococcin P1 naturally or by a genetic modification. In other cases, the composition comprises Micrococcin P1 by including crude extracts of the bacteria capable of expression of Micrococcin P1 naturally or by genetic engineering. The crude extracts can be generated by obtaining a fraction of the bacterial culture including Micrococcin P1.

Micrococcin P1 can be present at a concentration sufficient to induce a zone of inhibition when the composition is applied to an agar plate culture of *Streptomyces scabies*. Micrococcin P1 can be present at a concentration sufficient to protect a potato from *Streptomyces scabies* when the composition is applied to a pot. Micrococcin P1 can be present at a concentration sufficient to protect a potato from *Streptomyces scabies* when the composition is applied to a field. The concentration of Micrococcin P1 effective for the bioprotection from *Streptomyces scabies* can be determined by testing dose-dependent responses. In some embodiments, Micrococcin P1 is present at a concentration greater than 1 µg/L, 10 µg/L, 100 µg/L, 500 µg/L, 1 mg/L, 5 mg/L, 10 mg/L, 100 mg/L, or 500 mg/L. In some embodiments, Micrococcin P1 is present at a concentration greater than 1 nM, 10 nM, 100 nM, 200 nM, 500 nM, 1 µM or 10 µM.

In some embodiments, Micrococcin P1 is applied at a concentration greater than 1 µg/L, 10 µg/L, 100 µg/L, 500 µg/L, 1 mg/L, 5 mg/L, 10 mg/L, 100 mg/L, or 500 mg/L. In some embodiments, Micrococcin P1 is applied at an amount greater than 1 ag/Acre, 10 ag/Acre, 100 ag/Acre, 500 ag/Acre, 1 mg/Acre, 5 mg/Acre, 10 mg/Acre, 100 mg/Acre, 500 mg/Acre, or 1 g/Acre.

In some embodiments, the composition can include Micrococcin P1, which is chemically synthesized. In some embodiments, the composition can include Micrococcin P1, which is biologically produced, but purified.

4.3.2. Agriculturally Acceptable Carrier

In some embodiments, the compositions further comprise an agriculturally acceptable carrier. The agriculturally acceptable carrier can be added to enhance antimicrobial activity of the compositions. In some embodiments, the agriculturally acceptable carrier is added to enhance stability of the antimicrobial agent (e.g., Micrococcin P1) during storage or after application of the composition to a field. In some embodiments, the agriculturally acceptable carrier is added to provide an effective concentration of active components before being applied to a soil or to a plant.

4.3.2.1. Culture Medium

In some embodiments, the composition for treating *Streptomyces scabies* infection comprise culture medium as an agriculturally acceptable carrier. Culture medium is a mixture which supports the growth of microbial cells, such as *Bacillus pumilus*, *Bacillus subtilis*, or other microbes disclosed herein. Culture medium can contain ingredients such as peptone, soy peptone, molasses, potato starch, yeast extract powder, or combinations thereof.

4.3.2.2. Filtered Fraction of Microbial Culture

In some embodiments, the compositions of treating *Streptomyces scabies* further comprise a cell-free supernatant of a microbial culture inoculated with one or more isolated microorganism, wherein the microorganism comprises *Aspergillus* spp., *Bacillus* spp., *Rhodopseudomonas* spp., *Candida* spp., *Lactobacillus* spp., *Saccharomyces* spp., or *Lactococcus* spp.; or combinations thereof.

In some embodiments, the compositions of treating *Streptomyces scabies* further comprise a cell-free supernatant of a microbial culture inoculated with one or more isolated microorganism, wherein the microorganism comprises *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; or combinations thereof.

In some embodiments, the compositions of treating *Streptomyces scabies* comprise a cell-free supernatant of a microbial culture inoculated with one or more isolated microorganism, wherein the microorganism comprises *Aspergillus* spp., for example, *Aspergillus oryzae*, IN-AO1, deposited Sep. 4, 2014 with ATCC, PTA-121551; *Bacillus* spp., for example, *Bacillus amyloliquefaciens*, IN-BS1, deposited Jan. 11, 2012 with ATCC, PTA-12385; *Rhodopseudomonas* spp., for example, *Rhodopseudomonas palustris*, IN-RP1, deposited Jan. 11, 2012 with ATCC, PTA-12387; *Rhodopseudomonas palustris*, IN-RP2, deposited Sep. 4, 2014 with ATCC, PTA-121533; *Candida* spp., for example, *Candida utilis*, IN-CU1, deposited Sep. 4, 2014 with ATCC, PTA-12550; *Lactobacillus* spp., for example, *Lactobacillus helveticus*, IN-LHI, deposited Jan. 11, 2012, with ATCC, PTA 12386; *Lactobacillus rhamnosus*, IN-LR1, deposited Sep. 4, 2014 with ATCC, PTA 121554; *Lactobacillus paracasei*, IN-LC1, deposited Sep. 4, 2014 with ATCC, PTA-121549; *Lactobacillus plantarum*, IN-LPl, deposited Sep. 4, 2014 with ATCC, PTA 121555; *Lactococcus* spp., for example, *Lactococcus lactis*, IN-LL1, deposited Sep. 4, 2014 with ATCC, PTA-121552; *Pseudomonas* spp., for example, *Pseudomonas aeruginosa* or *Pseudomonas fluorescens*; *Saccharomyces* spp., for example, *Saccharomyces cerevisiae*, IN-SC1, deposited on Jan. 11, 2012 with ATCC, PTA-12384; or *Streptococcus* spp., for example, *Streptococcus lactis*; or combinations thereof, or a microbial consortia comprising one or more of the above, for example, IN-M1, deposited Jan. 11, 2012 with ATCC, PTA-12383 and/or IN-M2, deposited Sep. 4, 2014 with ATCC, PTA-121556. IN-BS1, ATCC Deposit No. PTA-12385, was previously identified to be *Bacillus subtilis* in US Publication Nos. 20160100587 and 20160102251, and U.S. Pat. No. 9,175,258 based on 16S rRNA sequence and API testing, but later identified to be *Bacillus amyloliquefaciens* by full genome sequencing. IN-LC1, ATCC Deposit No. PTA-121549, was previously identified to be *Lactobacillus casei* in US Publication Nos. 20160100587 and 20160102251, and U.S. Pat. No. 9,175,258 based on 16S rRNA sequence and API testing, but later identified to be *Lactobacillus paracasei* by full genome sequencing.

In some embodiments, the cell-free supernatant is filter-sterilized or sterilized by methods known to those of skill in the art. The cell-free supernatant can be made by methods described in US Publication Nos. 20160100587 and 20160102251, and U.S. Pat. No. 9,175,258, which are incorporated by reference in their entireties herein.

For example, microorganisms grown for producing cell-free supernatant compositions of the present disclosure can be grown in fermentation, nutritive or culture broth in large, industrial scale quantities. For example, and not to be limiting, a method for growing microorganisms in 1000 liter batches comprises media comprising 50 liters of non-sulfur agricultural molasses, 3.75 liters wheat bran, 3.75 liters kelp, 3.75 liters bentonite clay, 1.25 liters fish emulsion (a commercially available organic soil amendment, from Nutrivert, Dunham, Quebec non-pasteurized), 1.25 liters soy flour, 675 mg. commercially available sea salt, 50 liters selected strains of microorganisms, up to 1000 liters non-chlorinated warm water. A method for growing the microorganisms can further comprise dissolving molasses in some of the warm water, adding the other ingredients to the fill tank, keeping the temperature at 30° C., and, after the pH drops to about 3.7 within 5 days, stirring lightly once per day and monitoring pH. The culture can incubate for 6 weeks or a predetermined time, the culture is then standardized (diluted or concentrated) to a concentration of $1\times10^5$-$1\times10^7$, or $1\times10^6$ cells/mL, after which the microorganisms are removed to result in a cell-free supernatant composition, a composition of the present disclosure.

A microbial culture, which is the source of a cell-free supernatant composition of the present disclosure can be inoculated with and comprise a combination of microorganisms from several genera and/or species. These microorganisms grow and live in a cooperative fashion, in that some genera or species may provide by-products or synthesized compounds that are beneficial to other microorganisms in the combination. For example, the microbial culture, which is the source of a cell-free supernatant composition of the present disclosure can be inoculated with and comprise both aerobic microorganisms, which need oxygen for metabolic activities, and anaerobic microorganisms, which use other sources of energy such as sunlight or the presence of specific substrates. This enables the microorganisms to colonize substrates in different regions of an environment. A microbial culture, which is the source of a cell-free supernatant composition of the present disclosure can be inoculated with and comprise facultative microorganisms, for example, strains of *Lactobacillus*, which modulate metabolic activities according to oxygen and/or nutrient concentrations in the environment.

Though not wishing to be bound by any particular theory, it is currently believed that microbial cultures, which are the sources of cell-free supernatant compositions disclosed in the present disclosure may, during fermentation (culture) produce metabolites that are reactive in a cooperative manner. For example, a substrate or enzyme excreted by one or more microorganisms can be acted on by excreted products from other microorganisms in the culture to form metabolites, which can be referred to as tertiary metabolites. These excreted products and those products formed from the interactions of excreted products may work in concert in a beneficial manner to enhance or induce bioprotective properties in plants.

All species of living organisms include individuals that vary genetically and biochemically from each other but are still within what is called the spectrum of normal variations within the species. These individual natural variations can be the result of nondisruptive substitution or deletions in the gene sequence, variation in gene expression or RNA processing and/or variations in peptide synthesis and/or variation of cellular processing of intra cellular, membrane or secreted molecules. A microbial culture, which is the source of a cell-free supernatant composition of the present disclosure can be inoculated with microorganisms that are within or without the normal variations of a species. Identification of such microorganisms may be detected by genetic, molecular biological methods known to those skilled in the art, and/or by methods of biochemical testing.

For example, a microbial culture, which is the source of a cell-free supernatant composition of the present disclosure can be inoculated with and comprise microorganisms that were selected by isolating individual colonies of a particular microorganism. The colony members were characterized, for example, by testing enzyme levels present in the isolated microorganism and the activity with particular substrates in a panel of substrates, to establish an enzyme profile for the isolated microorganism.

Examples of these microorganisms that can be grown in cultures from which cell-free supernatants are derived include, but are not limited to, *Aspergillus* spp., *Bacillus* spp., *Rhodopseudomonas* spp., *Candida* spp., *Lactobacillus* spp., *Lactococcus* spp., *Pseudomonas* spp., *Saccharomyces* spp., or *Streptococcus* spp.; combinations thereof, or microbial consortia comprising one or more of these microorganisms, including IN-M1, deposited Jan. 11, 2012 with ATCC, PTA-12383, and/or IN-M2, deposited Sep. 4, 2014 with ATCC, PTA-121556.

Compositions of the present disclosure can comprise differing amounts and combinations of these and other isolated microorganisms depending on the methods being performed. A microbial culture is formed by inoculating a microbial nutrient solution, commonly referred to as a broth, with one or more microorganisms disclosed herein. A microbial culture is formed by the growth and metabolic activities of the inoculated microorganisms. Thus, in various aspects, the microbial culture is inoculated with and comprises at least two of *Aspergillus* spp., *Bacillus* spp., *Rhodopseudomonas* spp., *Candida* spp., *Lactobacillus* spp., *Pseudomonas* spp., *Saccharomyces* spp., or *Streptococcus* spp. In an aspect, the microbial culture is inoculated with and comprises *Aspergillus oryzae*, *Bacillus amyloliquefaciens*, *Lactobacillus helveticus*, *Lactobacillus paracasei*, *Rhodopseudomonas palustris*, and *Saccharomyces cerevisiae*. In an aspect, the microbial culture is inoculated with and comprises a mixed culture, IN-M1 (Accession No. PTA-12383). In an aspect, the microbial culture is inoculated with and comprises *Aspergillus oryzae*, *Bacillus amyloliquefaciens*, *Candida utilis*, *Lactobacillus paracasei*, *Lactobacillus helveticus*, *Lactobacillus plantarum*, *Lactobacillus rhamnosus*, *Lactococcus lactis*, *Rhodopseudomonas palustris*, and *Saccharomyces cerevisiae*.

In an aspect, a microbial culture is inoculated with and comprises a mixed culture, the consortia IN-M1, deposited with the ATCC Patent Depository under the Budapest Treaty, on Jan. 11, 2012, under Account No. 200139, and given Accession No. PTA-12383. IN-M1 consortia comprises *Rhodopseudomonas palustris*, IN-RP1, ATCC Deposit No. PTA-12387; *Aspergillus oryzae*, *Saccharomyces cerevisiae*, IN-SC1, ATCC Deposit No. PTA-12384, *Bacillus amyloliquefaciens*, IN-BS1, ATCC Deposit No. PTA-12385; *Lactobacillus helveticus*, IN-LH1, ATCC Deposit No. PTA-12386; and *Lactobacillus paracasei*. In an aspect, the microbial culture is inoculated with and comprises a mixed culture, IN-M1, in combination with one or more disclosed microbial organisms. After growth, the microbial culture is either diluted or concentrated to be $1 \times 10^5$-$1 \times 10^7$, or $1 \times 10^6$ cells/mL and a cell-free supernatant composition is derived from this IN-M1 fermentation culture by removing the microorganisms that were present in the microbial fermentation culture.

In an aspect, a microbial fermentation culture is inoculated with a mixed culture, IN-M2, deposited with the ATCC Patent Depository under the Budapest Treaty, on Sep. 4, 2014, with the designation IN-M2, under Account No. 200139, with the ATCC Patent Deposit Designation No. PTA-121556. The microbial consortia, IN-M2 comprises *Lactobacillus paracasei*, IN-LC1, ATCC Deposit No. PTA-121549; *Lactobacillus helveticus*, IN-LH1, ATCC Deposit No. PTA-12386; *Lactococcus lactis*, IN-LL1, ATCC Deposit No. PTA-121552; *Lactobacillus rhamnosus*, IN-LR1, ATCC Deposit No. PTA-121554; *Lactobacillus plantarum*, IN-LP1, ATCC Deposit No. PTA-121555; *Rhodopseudomonas palustris* IN-RP1, ATCC Deposit No. PTA-12387; *Rhodopseudomonas palustris*, IN-RP2, ATCC Deposit No. PTA-121553; *Saccharomyces cerevisiae*, IN-SC1, ATCC Deposit No. PTA-12384; *Candida utilis*, IN-CU1, ATCC Deposit No. PTA-121550; *Aspergillus oryzae*, IN-AO1, ATCC Deposit No. PTA-121551; and *Bacillus amyloliquefaciens*, IN-BS1, ATCC Deposit No. PTA-12385. In an aspect, the microbial fermentation culture is inoculated with and comprises a mixed culture, IN-M2, in combination with one or more disclosed microbial organism. After growth, the microbial culture is either diluted or concentrated to be $1 \times 10^5$-$1 \times 10^7$, or $1 \times 10^6$ cells/mL and a cell-free supernatant composition is derived from this IN-M2 culture by removing the microorganisms that were present in the microbial culture.

4.3.2.2.1. Selection Criteria

Compositions of microorganisms for providing a cell-free supernatant can be selected based on one or more criteria provided herein. Specifically, antimicrobial activity of active components can be combined with a cell-free supernatant of various microorganisms and then tested against *Streptomyces scabies* on a culture plate, in a culture media, or in the field. Microorganisms are selected when their supernatant fractions provide synergistic, additive, or any other positive effect on antimicrobial activity of the active components, such as *Bacillus pumilus, Bacillus pumilus*, Micrococcin P1, or a combination thereof.

4.3.3. Other Optional Components

In some embodiments, an antimicrobial composition of the present disclosure may further comprise one or more additional or optional components, including but not limited to, herbicides, insecticides, fungicides, nutrient compounds, peptides, proteins, delivery components, or combination thereof.

In some embodiments, the antimicrobial composition further comprises a nutrient component. The nutrient component can be powders, granules, or pellets, or a liquid, including solutions or suspensions, which contains nutrients in the solution or in the mixture.

In some embodiments, the antimicrobial composition further comprises copper or its alloy, including but not limited to, brasses, bronzes, cupronickel, and copper-nickel-zinc.

4.4. Methods of Protecting Potatoes from *Streptomyces scabies*

In an aspect, provided herein are methods for protecting potatoes from *Streptomyces scabies* by applying an effective amount of the antimicrobial composition of the present invention.

4.4.1. Methods of Application

The antimicrobial composition can be applied at a particular time, or one or more times, depending on the pathogen population in the soil, environmental conditions and potato susceptibility. The compositions can be applied to the soil (1) where a plant rooted therein showed a pathological symptom associated with *Streptomyces scabies*, (2) where a plant currently rooted therein shows a pathological symptom associated with *Streptomyces scabies*, or (3) where a potato which will be planted therein is expected to show a pathological symptom associated with *Streptomyces scabies*. In some embodiments, the compositions are applied to the seeds that will be planted to such a soil. In some embodiments, the compositions are applied to the seeds that have been planted to such a soil. In some embodiments, the compositions are applied to the plant that is rooted in such a soil. In some embodiments, the compositions are applied to a plant that shows a pathological symptom associated with *Streptomyces scabies*.

The compositions can be applied subsequent to or prior to infection by *Streptomyces scabies*. In some embodiments, the composition is applied at least 1 week, 2 weeks, 3 weeks, 1 months, 2 months, 3 months, 4 months, 5 months, or 6 months before planting a seed. In some embodiments, the composition is applied at least 1 week, 2 weeks, 3 weeks, 1 months, 2 months, 3 months, 4 months, 5 months, or 6 months after planting a seed. In some embodiments, the composition is applied 1 week, 2 weeks, 3 weeks, 4 weeks, 5 weeks, 5-20 weeks, 10-15 weeks, 10-14 weeks, 11 weeks, 12 weeks, 13 weeks, or 14 weeks before harvesting a potato.

Suitable application methods include, but are not limited to, high or low pressure spraying, drenching, coating, immersion, and soil injection. In various aspects, disclosed compositions can be applied to soil or other plant growth media and/or can be applied to seeds prior to or during planting.

When treating seeds, disclosed compositions can be applied by a variety of techniques including, but not limited to, high or low pressure spraying, coating, immersion, and injection. Once treated, seeds can be planted in natural or artificial soil and cultivated using conventional procedures to produce plants. After plants have propagated from seeds treated in accordance with the present disclosure, the plants may be treated with one or more applications of disclosed compositions.

Disclosed compositions can be applied to all or part of the plant. For example, a disclosed composition can be applied to the stems, roots, leaves, and/or propagules (e.g., cuttings). The plant may be treated at one or more developmental stages.

In some embodiments, the compositions can be applied to a delivery vehicle, wherein the delivery vehicle serves as a means of transporting the bioprotective properties from the delivery vehicle to the soil, plant, seed, field, etc. For example, disclosed compositions can be applied to a delivery vehicle (e.g., a particle, a polymer, or a substrate) to be used in filtration systems for the treatment of irrigation water. This technique may be useful in a variety of plant environments such as fields, greenhouse facilities, vertical farms, urban greening systems, and hydroponic systems. In some embodiments, disclosed compositions can be applied to a polymer as a wetting agent and/or gel that releases water as needed. In some embodiments, disclosed compositions can be applied to a delivery system for actives that effect solubility to concentrate actives for seed coatings. As used herein, "actives," refers to a molecule, or combination of molecules, having desired bioprotective properties that are produced during fermentation.

4.4.2. Amounts of Application

The antimicrobial compositions of the present invention is applied in an effective amount for bioprotection of a potato from *Streptomyces scabies*. In some embodiments, the amount is sufficient to prevent *Streptomyces scabies* infection. In some embodiments, the amount is sufficient to treat or reduce one or more symptoms associated with *Streptomyces scabies*. The specific amounts vary depending on the types and condition of soils, the types and conditions of potatoes, potency and activity of *Streptomyces scabies*, etc. The specific amounts can also vary depending on the environment, for example, whether it is in a pot or in a field. In some embodiments, the composition of the present invention is mixed with or diluted in an agriculturally acceptable carrier before used.

The specific amounts can be determined by using methods known in the art, for example, by testing dose dependent response. In some embodiments, the specific amount is determined by testing dose dependent response on a culture plate with *Streptomyces scabies*, for example, by measuring a zone of inhibition. In some embodiments, the specific amount is determined by testing dose dependent response in a pot or in a field. In some embodiments, the specific amount is determined based on the concentration of Micrococcin P1 in the composition. In some embodiments, the specific amount is determined based on the concentration of *Bacillus subtilis, Bacillus pumilus* or both.

When the composition is applied to a pot, the composition can be applied to provide a final concentration of *Bacillus subtilis, Bacillus pumilus*, or both to reach a concentration that ranges between $10^7$ and $10^9$ CFU/cm$^3$, between $2.5 \times 10^7$ and $7.5 \times 10^8$ CFU/cm$^3$, between $5 \times 10^7$ and $5 \times 10^8$ CFU/cm$^3$, or $10^8$ CFU/cm$^3$. When the composition is applied to a field, the composition can be applied in an amount that ranges between 0.2 and 3 gal/A, between 0.5 and 2.5 gal/A, between 0.75 and 2 gal/A, 0.5 gal/A, 1 gal/A, 1.25 gal/A, 1.5 gal/A, or 2 gal/A.

4.5. Examples

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations can be used, e.g., bp, base pair(s); kb, kilobase(s); pl, picoliter(s); s or see, second(s); min, minute(s); h or hr, hour(s); aa, amino acid(s); nt, nucleotide(s); and the like.

The practice of the present invention will employ, unless otherwise indicated, conventional methods of protein chemistry, biochemistry, recombinant DNA techniques and pharmacology, within the skill of the art.

4.5.1. Example 1: Isolation and Purification of Rhizobacteria

Rhizosphere soil and root samples were collected from various plant rhizospheres from Emile A. Lods Agronomy Research Centre (45° 26"05.5'N, 73° 55"57.2'W) and Morgan Arboretum (45° 26' 06.5" N, 73° 57"11.9'W) of the Macdonald Campus of McGill University. Rhizobacteria were isolated by dilution plate technique using phosphate buffered saline (PBS) solution. The rhizobacteria were serially diluted on LBA (Luria-Bertani Agar; composition (g/L): Tryptone—10 g, Yeast Extract—5 g, NaCl—5 g, Agar—15 g) and King's B Agar (composition (g/L): Peptone—20 g, glycerol—10 mL, K$_2$HPO$_4$— 1.5 g, MgSO$_4$.7H$_2$O—1.5 g, Agar—15 g) plates and incubated at 30° C. for at least 3 days. The plates were frequently observed for appearance of bacterial colonies during incubation. Colonies showing differences in size, color and morphology, were picked and streaked onto respective media plates followed by incubation as described earlier. Single colonies were again streaked on respective media plates until pure cultures were obtained. Morphologically distinct colonies were selected and grown in LB broth (shaken at 150 rpm on a rotary shaker at 30° C.) and stored in 25% glycerol (v/v) at −80° C.

4.5.2. Example 2: Screening of Antagonistic Rhizobacteria

Selected rhizobacterial isolates were cultured on LB agar ("LBA") plates and single colonies were selected for screening studies against *Streptomyces scabies*. Spore suspension of *Streptomyces scabies* was prepared in sterilized saline solution (0.85% NaCl) from already sporulating colonies that were allowed to grow on Potato Dextrose Agar (PDA; Difco, Detroit, MI) at 30° C. The antimicrobial activity of selected rhizobacterial isolates was tested using spot on lawn assay as provided in FIGS. 1A and B. Spore suspension (100 µL) was evenly spread on PDA using a sterile cell spreader and 10 µL of overnight culture (grown in LB broth at 30° C.) of each isolated strain was spotted on the lawn of *Streptomyces scabies*. The plates were incubated at 30° C. for 72 h. Antimicrobial activity was revealed by a zone of inhibition surrounding rhizobacterial isolates (FIGS. 1A-B).

4.5.3. Example 3: Identification of the Microbes

4.5.3.1. Example 3-1: Identification of the Microbes Based on 16S rRNA Sequences Colonies having antagonistic activity against *Streptomyces scabies* by creating a zone of inhibition as provided in Example 2 were selected and LB broth was inoculated with one of the colonies. The bacterial cultures were then allowed to grow on a shaker at 150 rpm for 2 days at 30±1° C. DNA was extracted from cells using QIAamp DNA Mini Kit (Cat. #51304, Qiagen, Toronto, Canada). The near full-length 16S rRNA was amplified using primers 27F (5' AGA GTT TGA TCM TGG CTC AG 3') and 1492R (5' TAC GGY TAC CTT GTT ACG ACT T 3'). The polymerase chain reaction (PCR) protocol involved: 25 µL Dream Taq PCR mastermix (Cat. #K1071, Fisher Scientific, Montreal, Canada), 5 µL each primer (1 µM) (IDT, Coralville, 10, USA), 5 µL template DNA in a final 50 µL reaction volume.

The thermocycling conditions involved 95° C. for 3 min followed by 40 cycles of 95° C. for 30 sec, 55° C. for 30 sec, 72° C. for 1 min and final extension of 72° C. for 5 min. Amplification was checked by electrophoresis in a 1.5% agarose gel stained with SYBR® Safe DNA gel stain (Cat. #S33102, Thermo Fisher Scientific, Canada) and bands were visualized (Gel Doc EZ Imager, Bio-Rad, Hercules, CA, USA). The sizes of the PCR fragments were compared against a 100-bp DNA ladder (Cat. #: 15628019; ThermoFisher Scientific, Canada). The 16S rRNA sequencing was done at Genome Quebec (McGill University and Genome Quebec Innovation Centre, Montreal, Canada), and compared with published 16S rRNA sequences using NCBI nucleotide Blast search. The forward and reverse sequences were aligned and a consensus sequence was created (TABLES 1-3).

The sequence analysis provided in TABLES 1-3 show that bacteria with antagonistic activity against *Streptomyces scabies* have 99-100% sequence identity to 16s rRNA of *Bacillus pumilus* or *Bacillus subtilis* sequences provided by NCBI. Specifically, 1$^{st}$ bacterium (ITI-1) was found to have 16s rRNA gene sequence with 100% identity and 100% coverage with *Bacillus pumilus* strain NES-CAP-1 (GenBank Accession No. MF079281.1); 2$^{nd}$ bacterium (ITI-2) was found to have 16s rRNA gene sequence with 99% identity and 100% coverage with *Bacillus subtilis* strain BSFLG01 (GenBank Accession No. MF196314.1); and 3$^{rd}$ bacterium (ITI-3) was found to have 16s rRNA gene sequence with 10000 identity and 10000 coverage with *Bacillus subtilis* strain SSL2 (GenBank Accession No. MH192382.1).

TABLE 1

| Primers | 16s rRNA gene sequence of the 1$^{st}$ barcterium with antagonistic activity against *Streptomyces scabies* (ITI-1) | Identification by NCBI Nucleotide BLAST Search |
|---|---|---|
| 27F<br>1492R | GAGCTTGCTCCCGGATGTTAGCGGCGGACGGGTGAGTAA<br>CACGTGGGTAACCTGCCTGTAAGACTGGGATAACTCCGG<br>GAAACCGGAGCTAATACCGGATAGTTCCTTGAACCGCAT<br>GGTTCAAGGATGAAAGACGGTTTCGGCTGTCACTTACAG<br>ATGGACCCGCGGCGCATTAGCTAGTTGGTGAGGTAACGG<br>CTCACCAAGGCGACGATGCGTAGCCGACCTGAGAGGGT<br>GATCGGCCACACTGGGACTGAGACACGGCCCAGACTCCT<br>ACGGGAGGCAGCAGTAGGGAATCTTCCGCAATGGACGA<br>AAGTCTGACGGAGCAACGCCGCGTGAGTGATGAAGGTTT<br>TCGGATCGTAAAGCTCTGTTGTTAGGGAAGAACAAGTGC<br>AAGAGTAACTGCTTGCACCTTGACGGTACCTAACCAGAA<br>AGCCACGGCTAACTACGTGCCAGCAGCCGCGGTAATACG<br>TAGGTGGCAAGCGTTGTCCGGAATTATTGGGCGTAAAGG<br>GCTCGCAGGCGGTTTCTTAAGTCTGATGTGAAAGCCCCC<br>GGCTCAACCGGGAGGGTCATTGGAAACTGGGAAACTT<br>GAGTGCAGAAGAGGAGAGTGGAATTCCACGTGTAGCGG<br>TGAAATGCGTAGAGATGTGGAGGAACACCAGTGGCGAA<br>GGCGACTCTCTGGTCTGTAACTGACGCTGAGGAGCGAAA<br>GCGTGGGGAGCGAACAGGATTAGATACCCTGGTAGTCC<br>ACGCCGTAAACGATGAGTGCTAAGTGTTAGGGGGTTTCC<br>GCCCCTTAGTGCTGCAGCTAACGCATTAAGCACTCCGCC<br>TGGGGAGTACGGTCGCAAGACTGAAACTCAAAGGAATT<br>GACGGGGGCCCGCACAAGCGGTGGAGCATGTGGTTTAA<br>TTCGAAGCAACGCGAAGAACCTTACCAGGTCTTGACATC<br>CTCTGACAACCCTAGAGATAGGGCTTTCCCTTCGGGGAC<br>AGAGTGACAGGTGGTGCATGGTTGTCGTCAGCTCGTGTC<br>GTGAGATGTTGGGTTAAGTCCCGCAACGAGCGCAACCCT<br>TGATCTTAGTTGCCAGCATTCAGTTGGGCACTCTAAGGT<br>GACTGCCGGTGACAAACCGGAGGAAGGTGGGGATGACG<br>TCAAATCATCATGCCCCTTATGACCTGGGCTACACACGT<br>GCTACAATGGACAGAACAAAGGGCTGCGAGACCGCAAG | 100% identity and 100% coverage with *Bacillus pumilus* strain NES-CAP-1 (GenBank Accession No. MF079281.1) |

TABLE 1-continued

| Primers | 16s rRNA gene sequence of the 1st barcterium with antagonistic activity against *Streptomyces* scabies (ITI-1) | Identification by NCBI Nucleotide BLAST Search |
|---|---|---|
| | GTTTAGCCAATCCCACAAATCTGTTCTCAGTTCGGATCGC<br>AGTCTGCAACTCGACTGCGTGAAGCTGGAATCGCTAGTA<br>ATCGCGGATCAGCATGCCGCGGTGAATACGTTCCCGGGC<br>CTTGTACACACCGCCCGTCACACCACGAGAGTTTGCAAC<br>ACCCGAAGTCGGTGAGGTAACC (SEQ ID NO: 1) | |

TABLE 2

| Primers | 16s rRNA gene sequence of the 2nd barcterium with antagonistic activity against *Streptomyces* scabies (ITI-2) | Identification by NCBI Nucleotide BLAST Search |
|---|---|---|
| 27F<br>1492R | GCAGTCGAGCGGACAGATGGGAGCTTGCTCCCTGATGTT<br>AGCGGCGGACGGGTGAGTAACACGTGGGTAACCTGCCT<br>GTAAGACTGGGATAACTCCGGGAAACCGGGGCTAATAC<br>CGGATGCTTGTTTGAACCGCATGGTTCAAACATAAAAGG<br>TGGCTTCGGCTACCACTTACAGATGGACCCGCGGCGCAT<br>TANNTAGTTGGTGAGGTAACGGCTCACCAAGGCAACGAT<br>GCGTAGCCGACCTGAGAGGGTGATCGGCCACACTGGGA<br>CTGAGACACGGCCCAGACTCCTACGGGAGGCAGCAGTA<br>GGGAATCTTCCGCAATGGACGAAACTCTGACGGAGCAA<br>CGCCGCGTGAGTGATGAAGGTTTTCGGATCGTAAAGCTC<br>TGTTGTTAGGGAAGAACAAGTACCGTTCGAATAGGGCGG<br>TACCTTGACGGTACCTAACCAGAAAGCCACGGCTAACTA<br>CGTGCCAGCAGCCGCGGTAATACGTAGGTGGCAAGCGTT<br>GTCCGGAATTATTGGGCGTAAAGGGCTCGCAGGCGGTTT<br>CTTAAGTCTGATGTGAAAGCCCCCGGCTCAACCGGGGAG<br>GGTCATTGGAAACTGGGGAACTTGAGTGCAGAAGAGGA<br>GAGTGGAATTCCACGTGTAGCGGTGAAATGCGTAGAGAT<br>GTGGAGGAACACCAGTGGCGAAGGCGACTCTCTGGTCTG<br>TAACTGACGCTGAGGAGCGAAAGCGTGGGGAGCGAACA<br>GGATTAGATACCCTGGTAGTCCACGCCGTAAACGATGAG<br>TGCTAAGTGTTAGGGGGTTTCCGCCCCTTAGTGCTGCAG<br>CTAACGCATTAAGCACTCCGCCTGGGGAGTACGGTCGCA<br>AGACTGAAACTCAAAGGAATTGACGGGGGCCCGCACAA<br>GCGGTGGAGCATGTGGTTTAATTCGAAGCAACGCGAAG<br>AACCTTACCAGGTCTTGACATCCTCTGACAATCCTAGAG<br>ATAGGACGTCCCCTTCGGGGGCAGAGTGACAGGTGGTGC<br>ATGGTTGTCGTCAGCTCGTGTCGTGAGATGTTGGGTTAA<br>GTCCCGCAACGAGCGCAACCCTTGATCTTAGTTGCCAGC<br>ATTCAGTTGGGCACTCTAAGGTGACTGCCGGTGACAAAC<br>CGGAGGAAGGTGGGGATGACGTCAAATCATCATGCCCCT<br>TATGACCTGGGCTACACACGTGCTACAATGGACAGAACA<br>AAGGGCAGCGAAACCGCGAGGTTAAGCCAATCCCACAA<br>ATCTGTTCTCAGTTCGGATCGCAGTCTGCAACTCGACTGC<br>GTGAAGCTGGAATCGCTAGTAATCGCGGATCAGCATGCC<br>GCGGTGAATACGTTCCCGGGCCTTGTACACACCGCCCGT<br>CACACCACGAGAGTTTGTAACACCCGAAGTCGGTGAGGT<br>AACC (SEQ ID NO: 2) | 99% identity and 100% coverage with *Bacillus subtilis* strain BSFLG01 (GenBank Accession No. MF196314.1) |

TABLE 3

| Primers | 16s rRNA gene sequence of the 3rd barcterium with antagonistic activity against *Streptomyces* scabies (ITI-3) | Identification by NCBI Nucleotide BLAST Search |
|---|---|---|
| 27F<br>1492R | TAGTTGGTGAGGTAACGGCTCACCAAGGCAACGATGCGT<br>AGCCGACCTGAGAGGGTGATCGGCCACACTGGGACTGA<br>GACACGGCCCAGACTCCTACGGGAGGCAGCAGTAGGGA<br>ATCTTCCGCAATGGACGAAAGTCTGACGGAGCAACGCCG<br>CGTGAGTGATGAAGGTTTTCGGATCGTAAAGCTCTGTTG<br>TTAGGGAAGAACAAGTACCGTTCGAATAGGGCGGTACCT<br>TGACGGTACCTAACCAGAAAGCCACGGCTAACTACGTGC<br>CAGCAGCCGCGGTAATACGTAGGTGGCAAGCGTTGTCCG<br>GAATTATTGGGCGTAAAGGGCTCGCAGGCGGTTTCTTAA<br>GTCTGATGTGAAAGCCCCCGGCTCAACCGGGGAGGGTCA<br>TTGGAAACTGGGGAACTTGAGTGCAGAAGAGGAGAGTG<br>GAATTCCACGTGTAGCGGTGAAATGCGTAGAGATGTGGA<br>GGAACACCAGTGGCGAAGGCGACTCTCTGGTCTGTAACT<br>GACGCTGAGGAGCGAAAGCGTGGGGAGCGAACAGGATT<br>AGATACCCTGGTAGTCCACGCCGTAAACGATGAGTGCTA | 100% identity and 100% coverage with *Bacillus subtilis* strain SSL2 (GenBank Accession No. MH192382.1) |

TABLE 3-continued 16s rRNA gene sequence of the 3rd barcterium with Identification by
antagonistic activity against *Streptomyces* scabiesNCBI Nucleotide
Primers (ITI-3) BLAST Search

```
AGTGTTAGGGGGTTTCCGCCCCTTAGTGCTGCAGCTAAC
GCATTAAGCACTCCGCCTGGGGAGTACGGTCGCAAGACT
GAAACTCAAAGGAATTGACGGGGGCCCGCACAAGCGGT
GGAGCATGTGGTTTAATTCGAAGCAACGCGAAGAACCTT
ACCAGGTCTTGACATCCTCTGACAATCCTAGAGATAGGA
CGTCCCCTTCGGGGGCAGAGTGACAGGTGGTGCATGGTT
GTCGTCAGCTCGTGTCGTGAGATGTTGGGTTAAGTCCCG
CAACGAGCGCAACCCTTGATCTTAGTTGCCAGCATTCAG
TTGGGCACTCTAAGGTGACTGCCGGTGACAAACCGGAGG
AAGGTGGGGATGACGTCAAATCATCATGCCCCTTATGAC
CTGGGCTACACACGTGCTACAATGGACAGAACAAAGGG
CAGCGAAACCGCGAGGTTAAGCCAATCCCACAAATCTGT
TCTCAGTTCGGATCGCAGTCTGCAACTCGACTGCGTGAA
GCTGGAATCGCTAGTAATCGCGGATCAGCATGCCGCGGT
GAATACGTTCCCGGGCCTTGTACACACCGCCCGTCACAC
CACGAGAGTTTGTAACACCCGAAGTCGGTGAGGTAACC
(SEQ ID NO: 3)
```

4.5.3.2. Example 3-2: Identification of the Microbes Based on API Tests

API 50 CHB/E Medium (Biomerieux 50 430) is intended for the identification of *Bacillus* and related genera. It is a ready-to-use medium which allows the fermentation of the 49 carbohydrates on the API 50 CH strip. A bacterial suspension of the test microorganism is made in the medium and each tube of the strip is then inoculated with the suspension. During incubation, the carbohydrates are fermented to acids which result in a decrease of the pH, detected by change in color of the indicator.

Three strains of bacteria identified as *Bacillus subtilis* (ITI-2 and ITI-3) and *Bacillus pumilus* (ITI-1) in Example 3-2 (their rRNA sequences are provided in TABLES 1-3) were streaked onto LBA plates and incubated at 30° C. for 48 hours. Several colonies from the pure culture were suspended in an ampule of API NaCl 0.85% (2 ml) in order to prepare a turbid bacterial suspension. A second ampule of API NaCl 0.85% was used in order to prepare a suspension with a turbidity equivalent to McFarland 2 by transferring certain number of drops from the previous suspension, recording the number of drops used (n). Inoculation of API 50 CHB/E ampule was performed by transferring twice the number of drops of suspension (2n) into the ampule followed by thorough mixing. The API 50 CHB/E Medium was then transferred to the gallery by filling all the 49 tubes, followed by incubation for 48 hours (+2 hours) @30° C. and then scored for activity according the manufacturer's instructions. A positive test corresponds to acidification revealed by the phenol red indicator contained in the medium changing to yellow. For the Aesculin test, a change in color from red to black was observed. Microbial identification was performed by entering the test results (positive or negative tests) in the apiweb identification website, apiweb.biometrieux.com. Results from the apiweb identification site are provided below in TABLE 4.

TABLE 4

| Test #. | Abbreviation[1] | Substrate[2] | Bacillus pumilus (ITI-1) | Bacillus subtilis (ITI-2) | Bacillus subtilis (ITI-3) |
|---|---|---|---|---|---|
| 1 | GLY | Glycerol | + | + | + |
| 2 | ERY | Erythritol | − | − | − |
| 3 | DARA | D-Arabinose | − | − | − |
| 4 | LARA | L-Arabinose | + | + | + |
| 5 | RIB | Ribose | + | + | + |
| 6 | DXYL | D-Xylose | − | + | + |
| 7 | LXYL | L-Xylose | − | − | − |
| 8 | ADO | Adonitol | − | − | − |
| 9 | MDX | β-Methylxyloside | − | − | − |
| 10 | GAL | Galactose | − | − | − |
| 11 | GLU | D-Glucose | + | + | + |
| 12 | FRU | D-Fructose | + | + | + |
| 13 | MNE | D-Mannose | + | + | + |
| 14 | SBE | L-Sorbose | − | − | − |
| 15 | RHA | Rhamnose | − | − | − |
| 16 | DUL | Dulcitol | − | − | − |
| 17 | INO | Inositol | − | + | + |
| 18 | MAN | Mannitol | + | + | + |
| 19 | SOR | Sorbitol | − | + | + |
| 20 | MDM | α-Methyl-D-mannoside | − | − | − |
| 21 | MDG | α-Methyl-D-glucoside | − | + | + |
| 22 | NAG | N-Acetylglucosamine | + | − | − |
| 23 | AMY | Amygdalin | + | + | + |
| 24 | ARB | Arbutin | + | − | − |
| 25 | ESC | Aesculin | + | + | + |
| 26 | SAL | Salicin | + | − | − |
| 27 | CEL | Cellobiose | + | + | + |
| 28 | MAL | Maltose | − | + | + |
| 29 | LAC | Lactose | − | − | − |
| 30 | MEL | Melibiose | − | + | + |
| 31 | SAC | Sucrose | + | + | + |
| 32 | TRE | Trehalose | + | + | + |
| 33 | INU | Inulin | − | + | + |
| 34 | MLZ | Melezitose | − | − | − |
| 35 | RAF | D-Raffinose | − | + | + |
| 36 | AMD | Starch | − | + | + |
| 37 | GLYG | Glycogen | − | + | + |
| 38 | XLT | Xylitol | − | − | − |
| 39 | GEN | β-Gentiobiose | − | − | − |
| 40 | TUR | D-Turanose | − | + | − |
| 41 | LYX | D-Lyxose | − | − | − |
| 42 | TAG | D-Tagatose | + | − | − |
| 43 | DFUC | D-Fucose | − | − | − |
| 44 | LFUC | L-Fucose | − | − | − |
| 45 | DARL | D-Arabitol | − | − | − |
| 46 | LARL | L-Arabitol | − | − | − |
| 47 | GNT | Gluconate | − | − | − |

TABLE 4-continued

| Test #. | Abbreviation[1] | Substrate[2] | Bacillus pumilus (ITI-1) | Bacillus subtilis (ITI-2) | Bacillus subtilis (ITI-3) |
|---|---|---|---|---|---|
| 48 | 2KG | 2-Ketogluconate | − | − | − |
| 49 | 5KG | 5-Ketogluconate | − | − | − |

[1](Ref. 50 430; API 50 CHB/E Medium; Biomerieux Inc., Durham, NC, USA)
[2]Logan N A & R C W Berkeley. 1984. Identification of *Bacillus* strains using the API system. J. Gen. Microbiol. 130: 1871-1882.
+ stands for Positive Reaction;
− stands for Negative Reaction The API test showed that one strain has activity 99.9% similar to *Bacillus pumilus* and two strains have activity 99.8 or 99.9% similar to *Bacillus subtilis*. These results confirmed that one strain identified to have antagonistic activity against *Streptomyces scabies* is *Bacillus pumilus* (ITI-1) and two strains are *Bacillus subtilis* (ITI-2 and 3).

Thus, based on both 16S rRNA gene sequencing and API test, the isolates were identified as *Bacillus pumilus* (ITI-1), *Bacillus subtilis* (ITI-2) and *Bacillus subtilis* (ITI-3) as summarized below in TABLE 5.

TABLE 5

| Bacterium | 16S rRNA gene sequencing | | API 50 CHB | |
|---|---|---|---|---|
| | Identification | Similarity (%) | Identification | Similarity (%) |
| *Bacillus* ITI-1 | *Bacillus pumilus* | 100% | *Bacillus pumilus* | 99.9% |
| *Bacillus* ITI-2 (small) | *Bacillus subtilis* | 99% | *Bacillus subtilis* | 99.8% |
| *Bacillus* ITI-3 (large) | *Bacillus subtilis* | 100% | *Bacillus subtilis* | 99.9% |

4.5.4. Example 4: Antimicrobial Activity of *Bacillus pumilus* and *Bacillus subtilis* Against *Streptomyces scabies*

*Bacillus pumilus* and *Bacillus subtilis* identified above in Example 3 were grown in LB broth and incubated on a shaker shaken at 150 rpm at 30±1° C. for 24 h. *Streptomyces scabies* was grown on PDA and incubated at 30° C. until the colonies sporulated. A spore suspension was prepared in 0.85% saline solution and was evenly spread on PDA plate. A 10 µL drop of overnight culture of *Bacillus pumilus* and *Bacillus subtilis* were spotted onto the PDA lawn of *Streptomyces scabies* and incubated for 3 days as described above. A zone of inhibition surrounding *Bacillus pumilus* and *Bacillus subtilis* colonies demonstrated antimicrobial activity against *Streptomyces scabies* (FIG. 1A). This experiment confirmed that *Bacillus pumilus* and *Bacillus subtilis* have antimicrobial activity against *Streptomyces scabies*.

In addition, the antimicrobial activity of the crude extracts from *Bacillus pumilus* and *Bacillus subtilis* was assessed via agar well diffusion assay. A spore suspension of *Streptomyces scabies* was overlaid on PDA and the plates were allowed to air dry. A 50 µL drop of crude extracts from *Bacillus pumilus* (top), *Bacillus pumilus* (right), and *Bacillus subtilis* (left) were poured into agar well and a control solution was pour on the bottom of the agar well. The Petri plates were incubated for 3 days 30° C. after which the bacterial lawns demonstrated growth inhibition zones near the application of the crude extracts (FIG. 1B). These results show that the crude extracts from *Bacillus pumilus* and *Bacillus subtilis* contain an antibiotic composition.

4.5.5. Example 5: Extraction, Purification, and Identification of the Antibiotic Produced by *Bacillus pumilus*

The 5 day-old bacterial culture of *Bacillus pumilus* was harvested and the antimicrobial compound isolated by phase partitioning the bacterial culture with 40% butanol while being shaken for 30 min (150 rpm). The butanol mixture was then allowed to stand overnight at 4° C. to phase partition butanol. The top butanol layer containing the antimicrobial compound was carefully collected and concentrated to dryness at 50° C. under vacuum by rotary evaporation (Yamato RE500; Yamato, CA, USA).

The concentrated material (crude extract) in the vessel was suspended in 10% acetonitrile (AcN/$H_2O$, v/v) and frozen at −20° C. until further analysis. The crude extract was centrifuged (Sorvall Biofuge Pico, Mandel Scientific, ON, Canada) at 13,000 rpm for 30 min to remove insoluble particles. The supernatant was filter sterilized (PVDF, 0.45 m, Fisher Scientific, Montreal, Canada) and tested for biological activity against *Streptomyces scabies*. The filtered extract was then loaded onto a C18 column (Restek™, Fisher Scientific, Montreal, Canada) and eluted with 20 mL of 10%, 20%, 40%, 60%, 80% and 100% acetonitrile and the fractions were collected. The eluted fractions under various concentrations of acetonitrile were lyophilized (SNL216V, Savant Instruments Inc., NY, USA), suspended in sterilized distilled water and tested for biological activity against *Streptomyces scabies*. The fraction showing an inhibition zone against *Streptomyces scabies* was selected for further fractionation by HPLC. The active fraction was stored in sterilized vials at 4° C. prior to HPLC analysis.

The fraction showing biological activity against *Streptomyces scabies* was further fractionated by HPLC (Waters Corporation, USA). The HPLC system was equipped with a Vydac C18 reversed-phase column (4.6×250 mm, 5 µm; cat. #218TP 5, Vydac, CA, USA) and fitted with waters 1525 Binary HPLC pump, a waters 2487 dual λ absorbance detector (Waters Corporation, USA) set at 214 nm and a WISP 712 autosampler. Prior to HPLC analysis the samples were centrifuged at 13,000 rpm for 10 min and 100 µL of the active fraction was subjected to HPLC analysis. Chromatography was conducted for 60 min using acetonitrile and water as solvents with a flow rate of 1 mL/min. The elution was carried out using a gradient of 10-95% acetonitrile (v/v) from 0-50 min, 95-10% acetonitrile from 50-52 min and finally at 10% acetonitrile from 52-60 min. Fractions were collected at 1-min intervals.

The collected samples were lyophilized in order to remove acetonitrile and suspended in sterilized water and tested for biological activity against *Streptomyces scabies*. Fractions showing antimicrobial activity against *Streptomyces scabies* were pooled together and subjected to another round of HPLC purification, freeze drying and biological activity assessment until a single pure peak was achieved.

The purified active material eluting as a single peak was collected and stored at 4° C. until further analyzed by mass spectrometry.

Figure 2A:
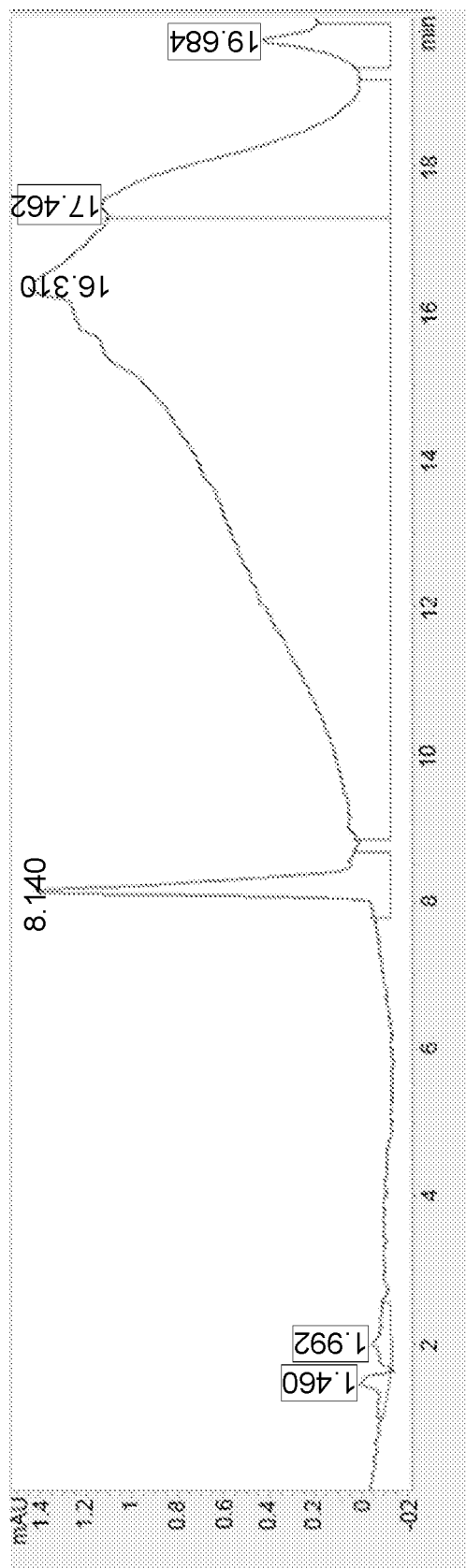
Figure 2B:
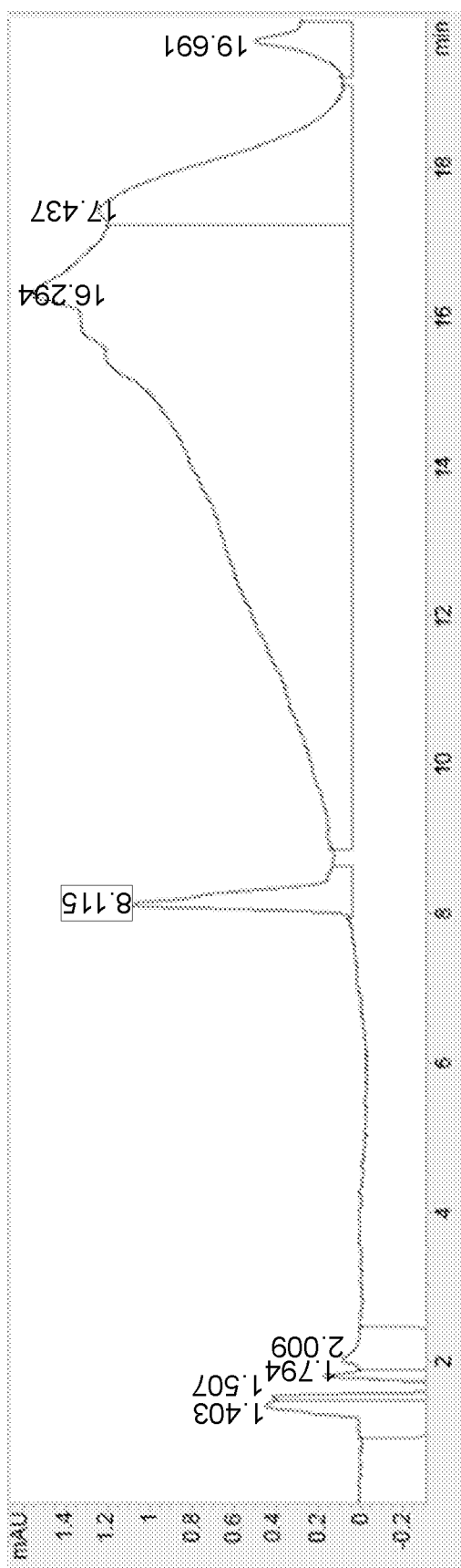

Liquid Chromatography Electrospray Ionization MS (LC-ESI-MS):

LC-ESI-MS analysis was performed over the mass range of m/z 50-2000 by passing the purified sample through a Spurcil C18 column (Dikma Technologies Inc., Canada; Cat. #: 82013) (2.1×150 mm, 3 m particle size) using Acetonitrile/$H_2O$/0.1% (v/v) formic acid on an Agilent 1100 HPLC system, coupled with LTQ Orbitrap Velos with ETD (Thermo Fisher Scientific) ion trap mass spectrometer in positive ion mode. The sample was run with a gradient of 10-95% acetonitrile for 17.0 min followed by 95-10% acetonitrile for 2.0 min and finally isocratic at 10% acetonitrile for 1.0 min. The flow rate was 0.2 mL/min with a run time of 20 min (FIGS. 2A-B and 3A-B). HPLC chromatogram of the purified fraction from Bacillus pumilus (FIG. 2A) was compared with HPLC chromatogram of the standard Micrococcin P1 purchased from Bioaustralis Fine Chemcials (Smithfield, NSW, Australia) (FIG. 2B).

Figure 3A:
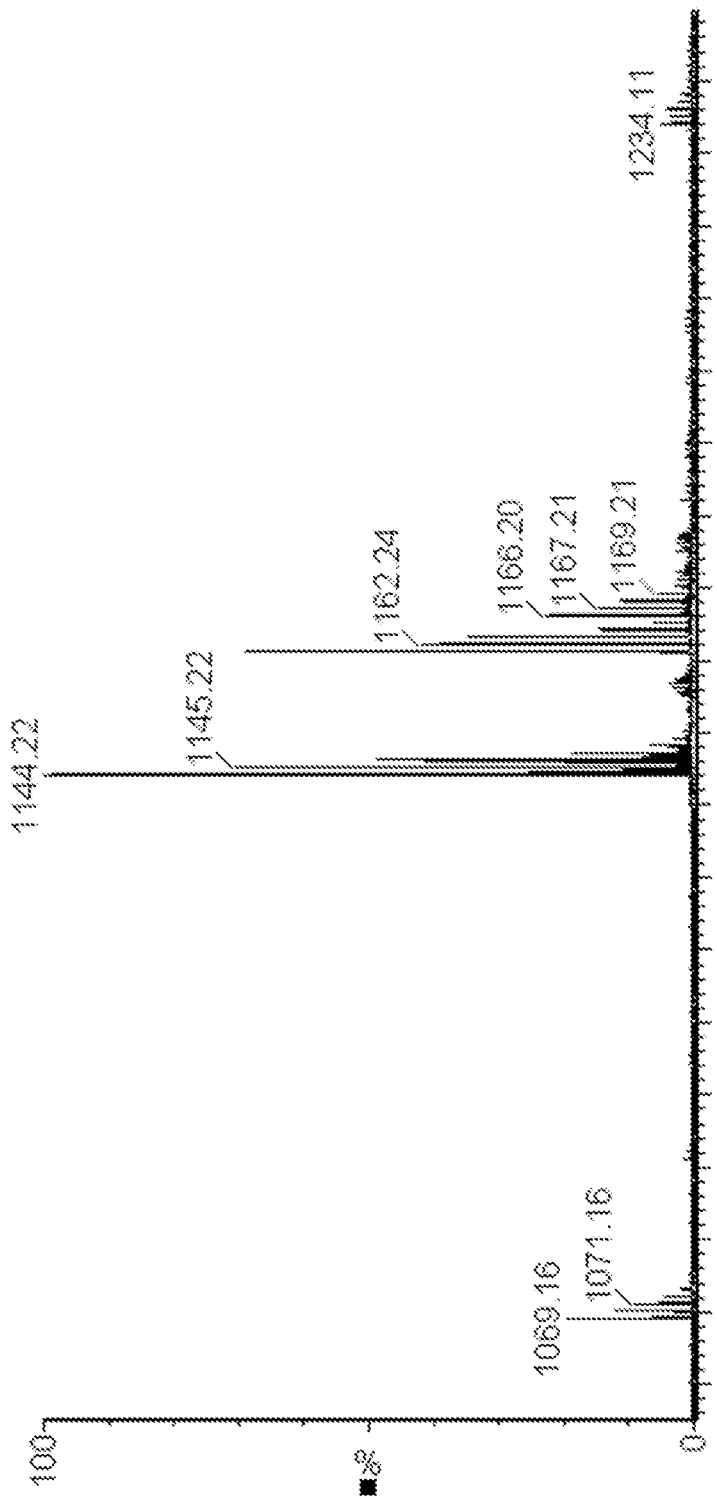
Figure 3B:
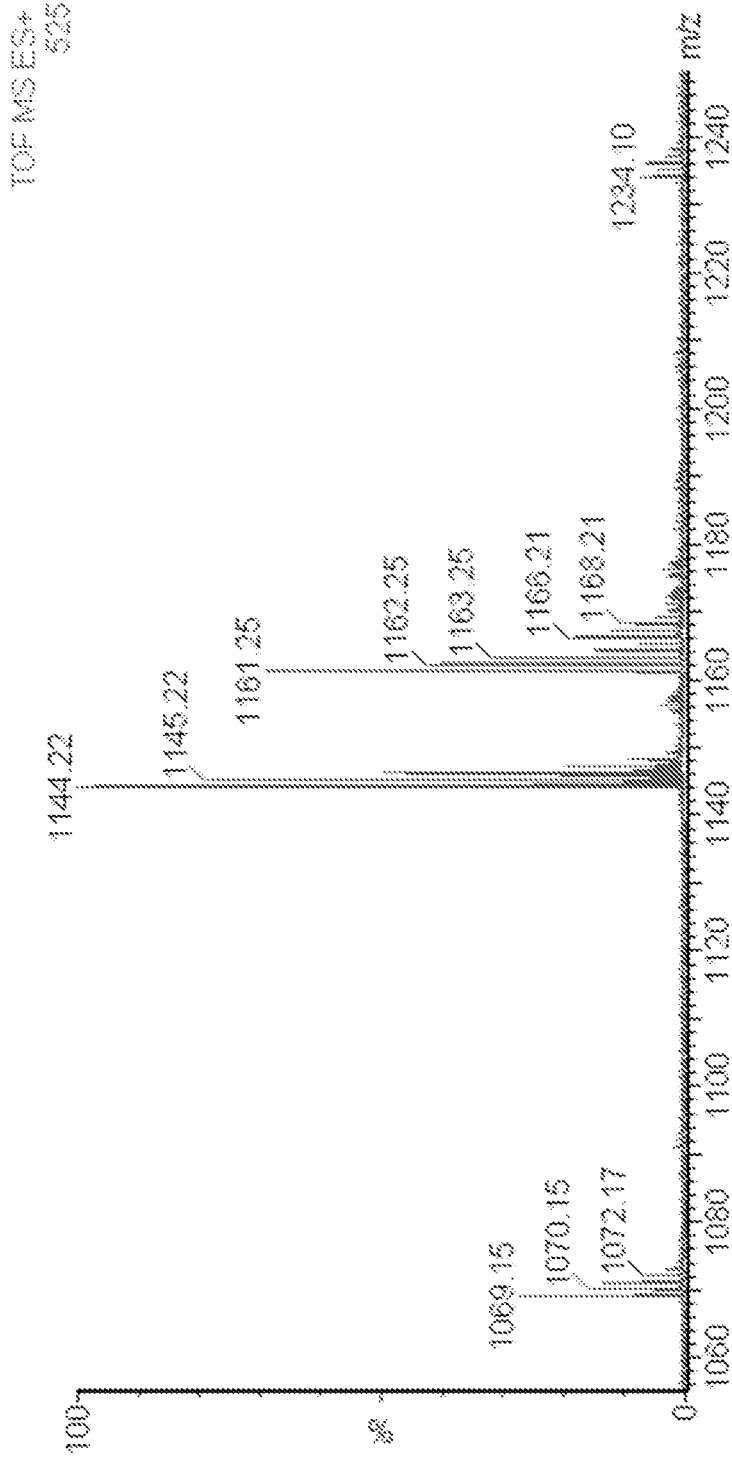

LC-MS chromatogram was further compared between the Bacillus pumilus active fraction (FIG. 3A) and standard Micrococcin P1 (FIG. 3B). LC-MS chromatogram of the analyzed Bacillus pumilus active fraction revealed three peaks of Micrococcin P1 homologues which corresponded to m z 1,144.22 $[M+H]^+$, m/z 1,161.25 $[M+NH_4]^+$, m/z 1,166.22 $[M+Na]^+$ (FIG. 3A). LC-MS chromatogram of the standard Micrococcin showed m/z 1,144.22 $[M+H]^+$, m/z 1,161.25 $[M+NH_4]^+$, m/z 1,166.21 $[M+Na]^+$ (FIG. 3B). When tested for biological activity, the standard Micrococcin P1 also showed antimicrobial activity against Streptomyces scabies.

Figure 4A:
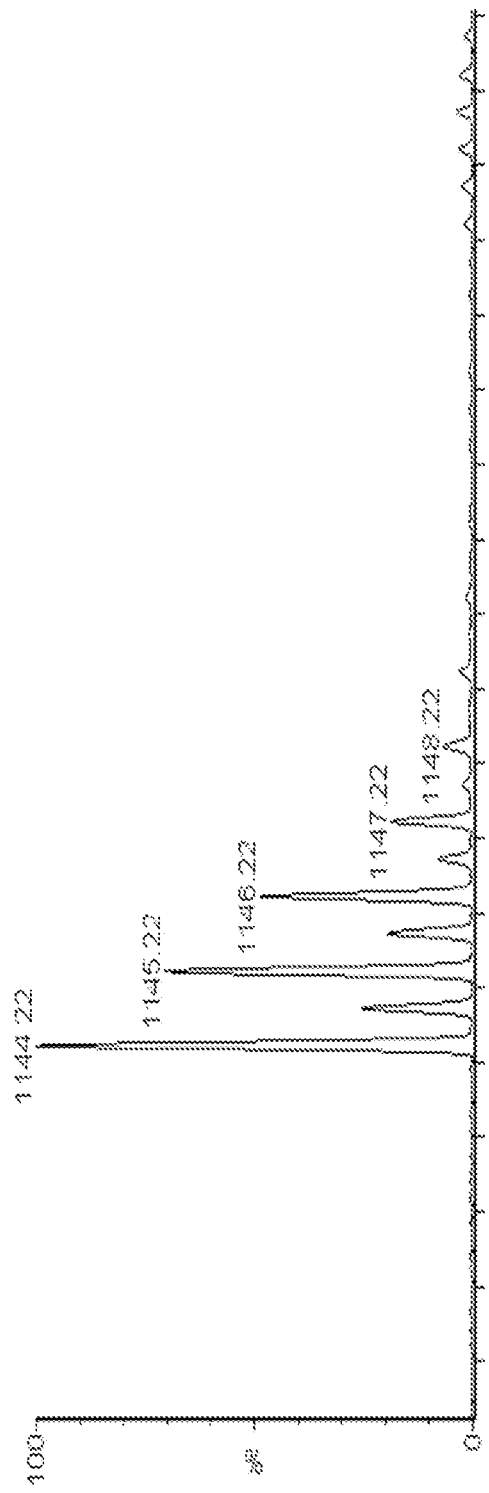
Figure 4B:
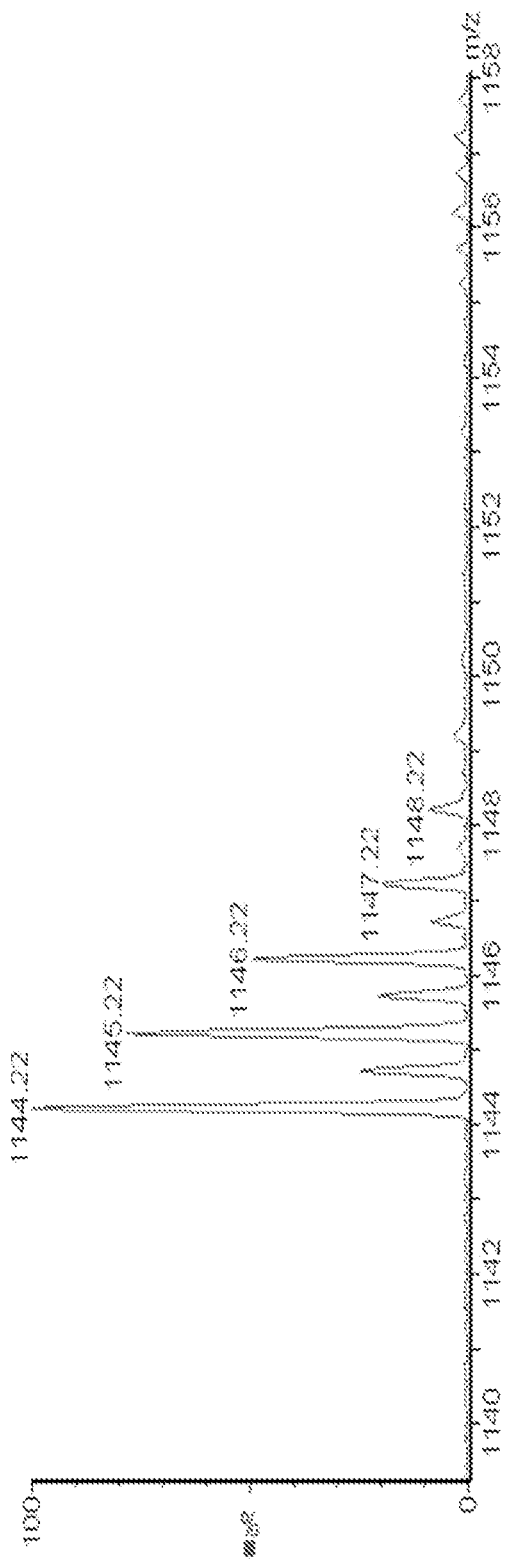

ESI-MS spectrum of the purified fraction from Bacillus pumilus (FIG. 4A) was also compared with ESI-MS spectrum of the standard Micrococcin P1 (FIG. 4B).

Figure 5:
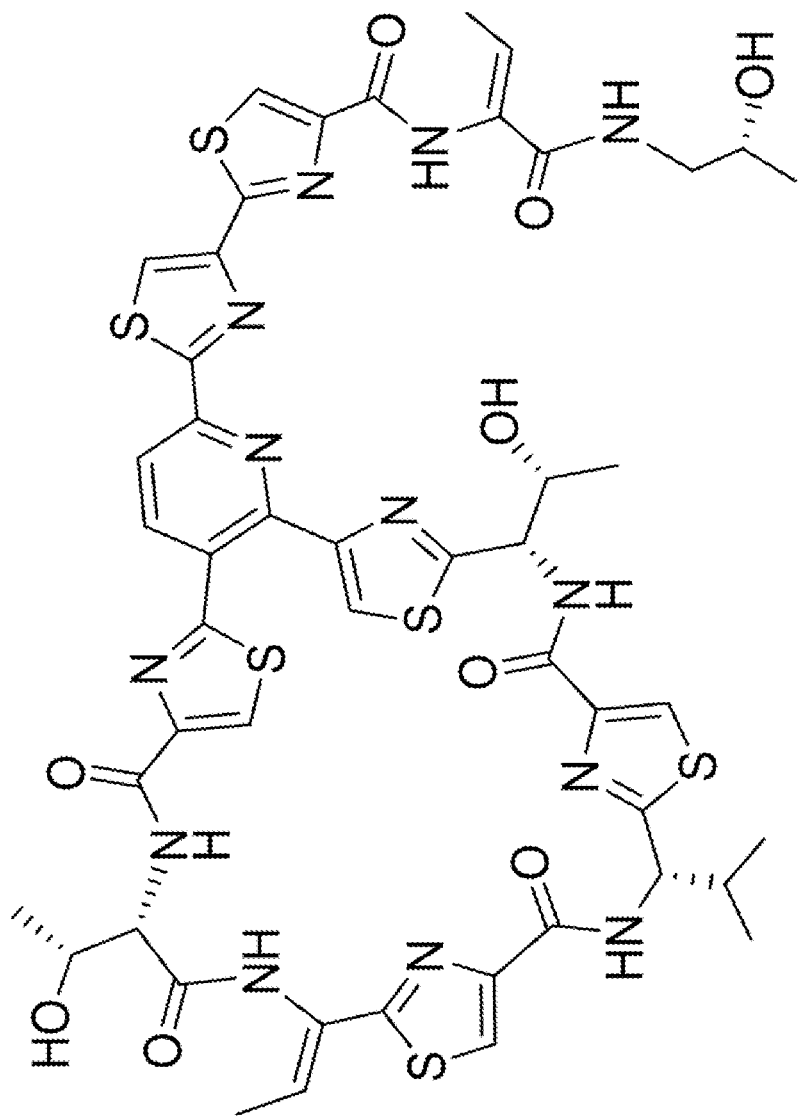

HPLC chromatogram, LC-MS chromatogram, and ESI-MS spectrum were detected significantly similar between the purified fraction from Bacillus pumilus (FIGS. 2A, 3A, and 4A) and standard Micrococcin P1 (FIGS. 2B, 3B, and 4B), suggesting that the antibiotic in the purified fraction is Micrococcin P1 (FIG. 5).

Figure 6:
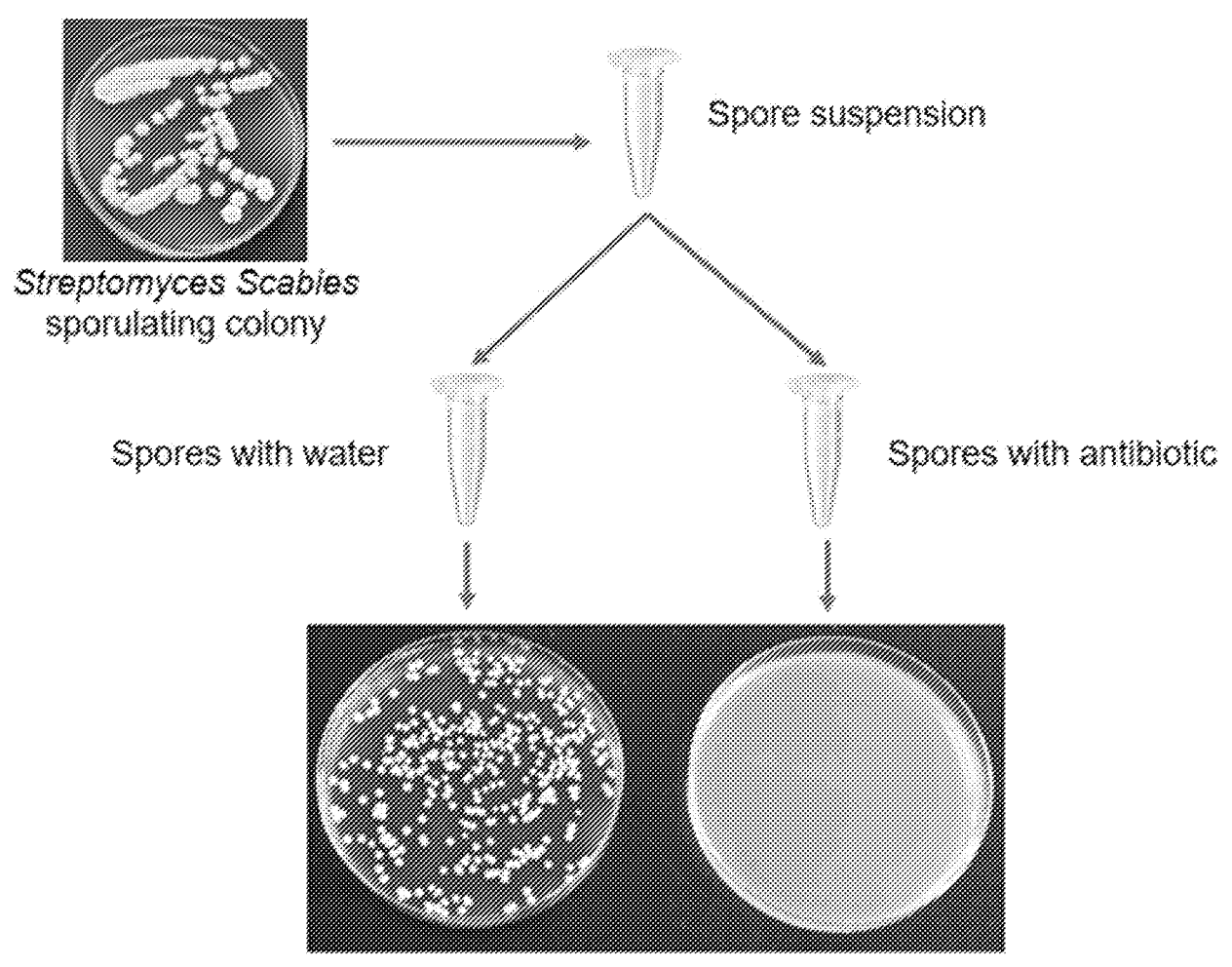

4.5.6. Example 6: Sporicidal Activity of the Antibiotic Micrococcin P1 Produced by Bacillus pumilus Against Streptomyces scabies Spores Streptomyces scabies was grown on Potato Dextrose Agar (PDA) and incubated at 30° C. until the colonies sporulated. A spore suspension was prepared in 0.85% saline solution and divided into two equal parts, one treated with crude Micrococcin P1 antibiotic extract (FIG. 6, plate on the right) and the other treated with sterile water (FIG. 6, plate on the left). The suspension was then incubated at 30° C. for 24 h and then spread on PDA plate. The plates were incubated at 30° C. for further 4 days. Results show that that the antibiotic inhibited spore germination (FIG. 6).

4.5.7. Example 7: Dose Dependent Antibacterial Activity of Micrococcin P1

The antimicrobial activities of Micrococcin P1 at various concentrations were assessed via agar well diffusion assay. A spore suspension of Streptomyces scabies was overlaid on PDA and the plates were allowed to air dry. A 50 μL drop of Micrococcin P1 diluted in various concentrations were applied into agar well. The petri plates were incubated for 3 days 30° C. and then the bacterial lawns were observed to measure growth inhibition zones around the application of Micrococcin P1.

Figure 7:
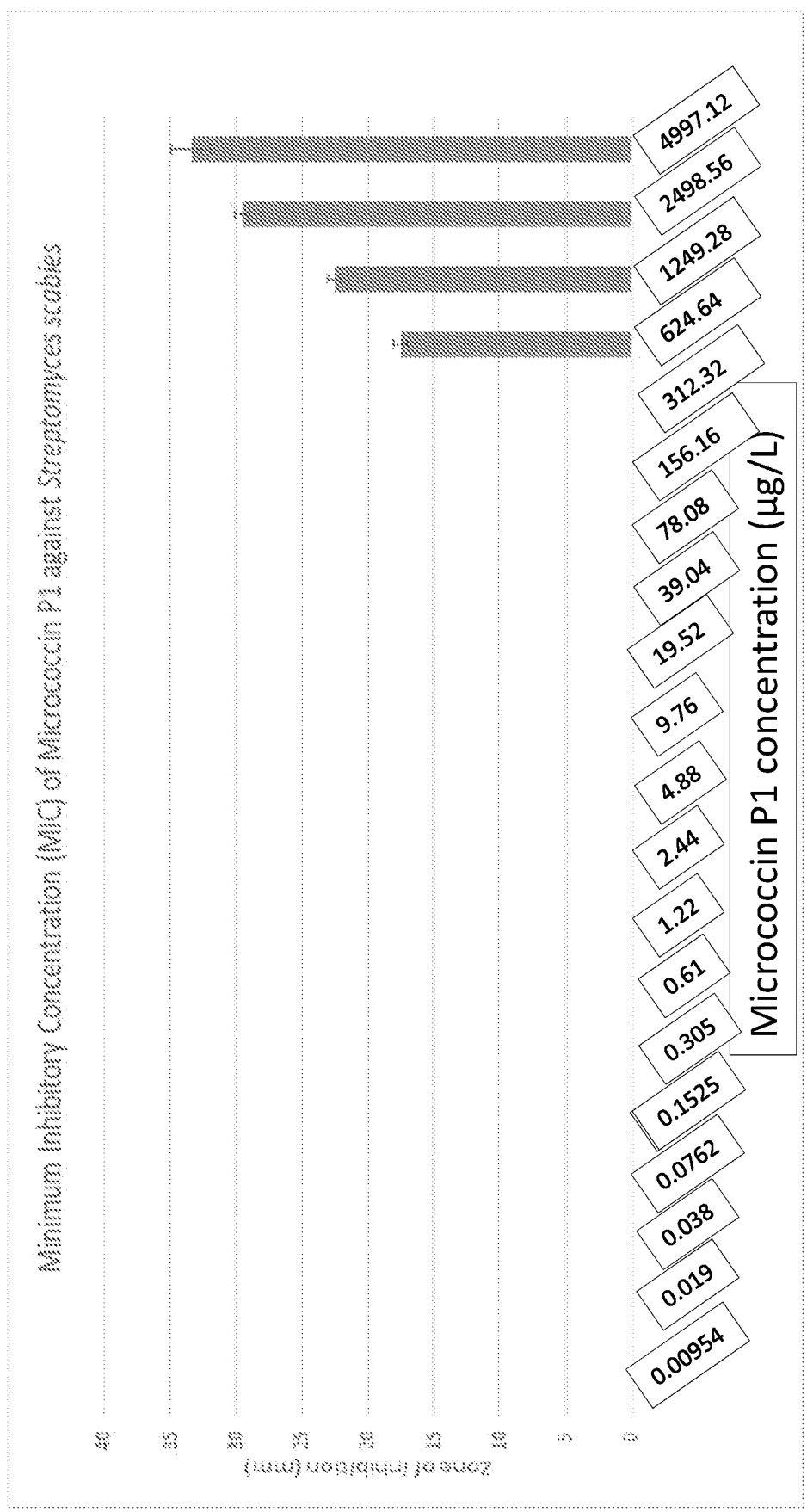

Micrococcin P1 demonstrated the antibacterial activities, providing growth inhibition zones on the plate only when applied at 31.25 ng or more per well in a 50 μL, which is at a concentration greater than 0.625 mg/L (i.e., 546 nM). The antibacterial activities increased proportional to the Micrococcin P1 concentrations (FIG. 7), having the most significant effects at 5 mg/L (i.e., 4.37 μM) concentration, which is the highest concentration tested in the experiment.

These results confirm that Micrococcin P1 is the antibacterial composition and Micrococcin P1 has to be present above a minimal concentration 0.625 mg/L (i.e., 546 nM) to provide the antibacterial activities against S. scabies on the LBA plate.

4.5.8. Example 8: Pot Experiment

A potato scab biocontrol experiment was conducted in pots using two potato cultivars, Yukon Gold and Kennebec. Seed potatoes were washed carefully and then surface sterilized in 20% commercial bleach solution for 5 minutes. The seed potatoes were then washed carefully with distilled water several times to remove the bleach solution. Two potato seed tubers (for each cultivar) were placed in 5 L plastic pots filled with AgroMix potting mixture (Teris, Laval, Quebec, Canada). Streptomyces scabies was inoculated by putting the inoculum on top of the potting mix at a final concentration $10^5$ CFU/$cm^3$.

For Bacillus subtilis and Bacillus pumilus application in the soil, a liquid culture was added to the potting mix as a drench to give a final concentration of $10^8$ CFU/$cm^3$. Bacillus subtilis and Bacillus pumilus cultures were grown in LB broth at 30° C., shaken at 150 rpm for 7 days. A control condition was also included (Streptomyces scabies only). There were 6 replications in each treatment. Plants were watered, every 2-3 days, and fertilized as needed. Potato tubers were harvested 11 weeks (Yukon Gold) and 12 weeks (Kennebec) after sowing. Tubers were washed and examined for scab lesions and given a severity rating using 0-5 scale. Where 0=no symptoms, 1=10%, 2=20%, 3=30%, 4=40%, 5=more than 50% of the surface area has scab lesions.

Figure 8:
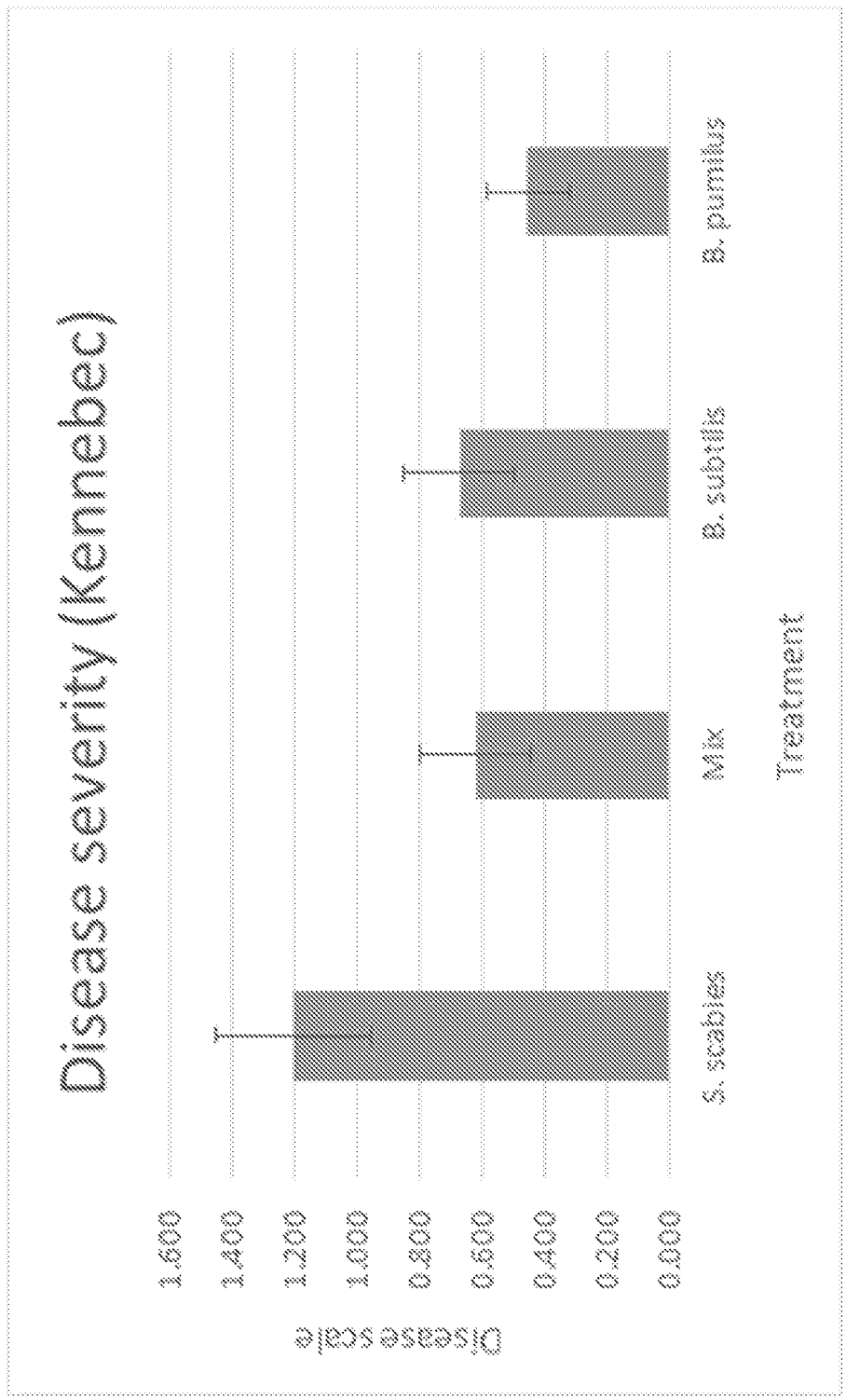
Figure 9:
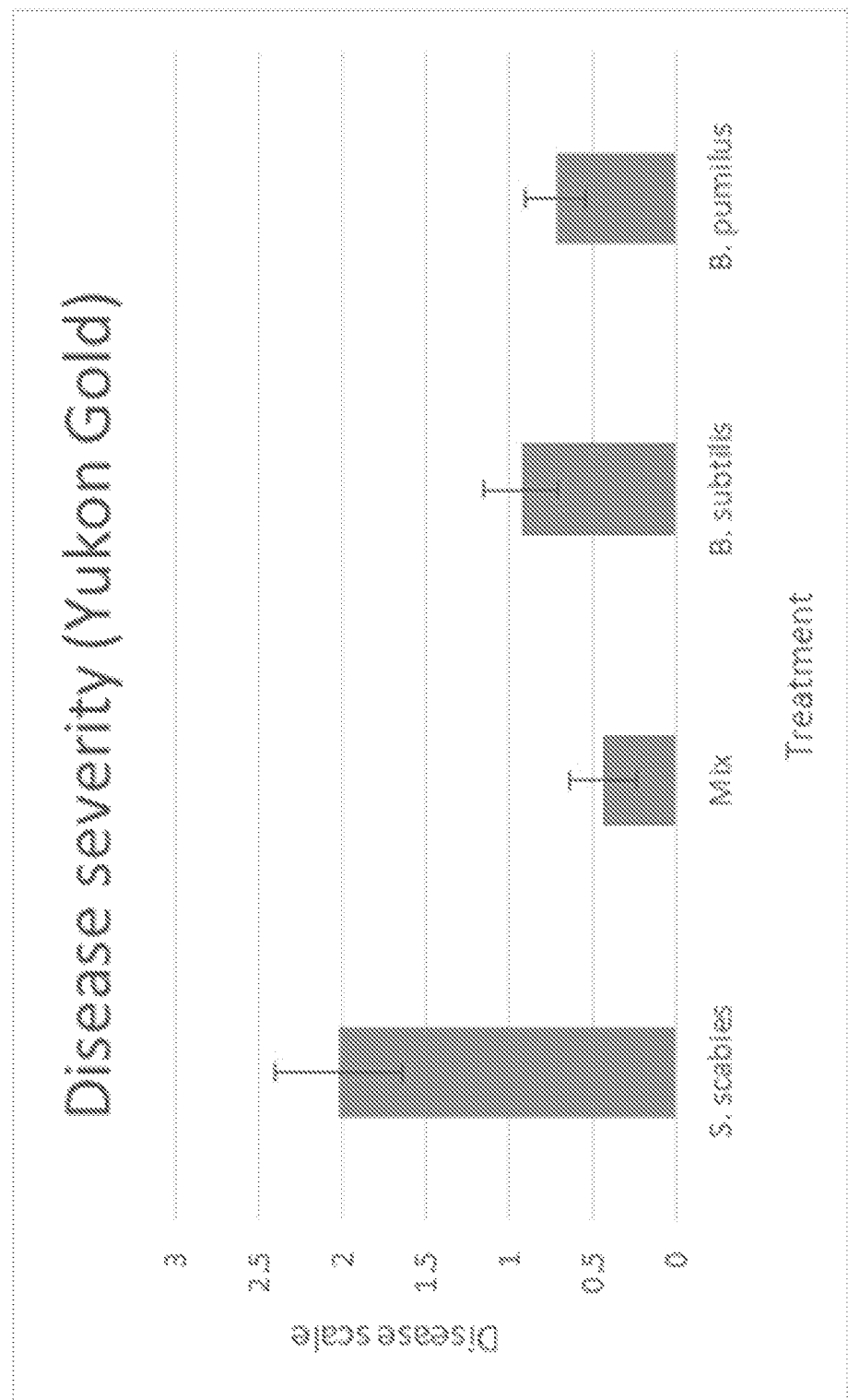

Severity ratings for potato tubers from the soil applied with Streptomyces scabies alone ("S. scabies"), Streptomyces scabies and a mix of Bacillus subtilis and Bacillus pumilus ("Mix"), Streptomyces scabies and Bacillus subtilis ("B. subtilis"), and Streptomyces scabies and B. pumilis ("B. pumilus") are provided in FIGS. 8 and 9. Specifically, FIG. 8 provides data from Kennebec potatoes, and FIG. 9 provides data from Yukon Gold potatoes. FIGS. 10A-9F further provides pictures of potatoes treated with Streptomyces scabies alone (FIG. 10A), Streptomyces scabies, Bacillus pumilus and Bacillus subtilis (FIG. 10B), Streptomyces scabies and Bacillus pumilus (FIG. 10C), or Streptomyces scabies and Bacillus subtilis (FIG. 10D). These results consistently demonstrate that Bacillus subtilis and Bacillus pumilus individually or in combination reduces the incidence of scab lesions on potato tubers when artificially inoculated with Streptomyces scabies. There was no effect on potato tuber yields.

4.5.9. Example 9: Field Experiment (Prince Edward Island, Canada)

Four experiments were conducted (at four different field sites) in Prince Edward Island (PEI) Canada on farmers' fields. Field sites with a history of scab disease were selected. Levelled uniform area was selected in each field and the experiment was performed as follows:

Treatments: There were four treatment groups in the experiment—control (water treated), BS (*Bacillus subtilis*), BP (*Bacillus pumilus*), BS+BP (*B. subtilis*+*Bacillus pumilus*), except Experiment 4 (data provided in FIGS. 14A and B) where the BS+BP treatment was omitted. Bacterial cultures were produced as described above in Example 8.

Experimental design: Latin square design with 4 replications. Each treatment condition was tested in a 20 ft long potato row.

Application: Already seeded potato hills were opened and the potato seeds were fully exposed. Treatments (liquid product diluted 10× in water and applied @ 1000 mL per treatment per replication) were applied in the furrows including the seeds, and the hills were closed. Cultivar Prospect was sown on three sites while cv. Shepody was sown on one site.

Potatoes were harvested at the end of the experiment (14 weeks) and data were collected on disease severity (<5%, 5-25%, >25% potato surface area affected)

Results are shown in FIGS. 11A-14B. Percentages of potato tubers having scab lesions on more than 25% of the potato surface area are provided in FIGS. 11A, 12A, 13A, and 14A. Percentages of potato tubers having scab lesions on less than 5% of the potato surface area are provided in FIGS. 11B, 12B, 13B and 14B. Our experimental results show that application of the bacteria alone or in a mixture reduced the incidence of potato scab lesions on potato tubers. The degree of this response varied specific to the site. The best response was obtained on site 2 (FIGS. 12A and B), while site 1 (FIGS. 11A and B) and 4 (FIGS. 14A and B) showed moderate reduction in scab disease incidence. Due to greater disease pressure on site 4, the response to product application was minimal. The total potato yield was not significantly different in various treatments.

4.5.10. Example 10: Field Experiment (Wisconsin and Maine, USA)

Potato biocontrol products containing *Bacillus subtilis* (*Bacillus subtilis*), *Bacillus pumilus* (*Bacillus pumilus*) or both were tested in Wisconsin and Maine in the US.

Trial Design—Wisconsin

Treatments: There were ten treatments in the experiment—control (water treated), and different amounts of BS (*Bacillus subtilis*), BP (*Bacillus pumilus*), or BS+BP (*B. subitlis*+*Bacillus pumilus*).

TABLE 5

| No. | *Bacillus subtilus* (Gallon/Acre) | *Bacillus pumilus* (Gallon/Acre) | Water (Gallon/Acre) |
|---|---|---|---|
| Wisconsin 1 (cont) | 0 | 0 | 5 |
| Wisconsin 2 | ½ | 0 | 4½ |
| Wisconsin 3 | 1 | 0 | 4 |
| Wisconsin 4 | 2 | 0 | 3 |
| Wisconsin 5 | 0 | ½ | 4½ |
| Wisconsin 6 | 0 | 1 | 4 |
| Wisconsin 7 | 0 | 2 | 3 |
| Wisconsin 8 | ¼ | ¼ | 4½ |
| Wisconsin 9 | ½ | ½ | 4 |
| Wisconsin 10 | 1 | 1 | 3 |

Experimental design: Completely randomized design with 6 replications. Each treatment condition was tested in four 40 feet long potato rows with 36 inches width.

Application: Already seeded potato hills were opened and the potato seeds were fully exposed. Treatments (liquid product diluted in water and applied 5 Gallon/Acre per treatment per replication) was applied in furrows including the seeds, and the hills were closed.

Trial Design—Maine

Treatments: There were four treatment groups in the experiment—control (water treated), BS (*Bacillus subtilis*), BP (*Bacillus pumilus*), or BS+BP (*B. subitlis*+*Bacillus pumilus*).

TABLE 6

| No. | *Bacillus subtilus* (Gallon/Acre) | *Bacillus pumilus* (Gallon/Acre) | Water (Gallon/Acre) |
|---|---|---|---|
| Maine 1 (cont) | 0 | 0 | 5 |
| Maine 2 | 0 | 1 | 4 |
| Maine 3 | 1 | 0 | 4 |
| Maine 4 | ½ | ½ | 4 |

Experimental design: Completely randomized design with 6 replications. Each treatment condition was applied to four 40 feet long potato rows with 36 inches width. Two middle rows were used for yield data.

Application: Already seeded potato hills were opened and the potato seeds were fully exposed. Treatments (liquid product diluted in water and applied 5 Gallon/Acre per treatment per replication) were applied in furrows including the seeds, and the hills were closed. Each condition was tested twice for two different potato varieties (Kennebec and Katahdin).

In the Wisconsin trial, potatoes treated with *Bacillus subtilis*, *Bacillus pumilus* or both were better than the control group in all three metrics: yield, cull rate, and scab severity rating as summarized below. Specifically, 54 out of 72 groups (75%) treated with *Bacillus subtilis*, *Bacillus pumilus* or both had better yields than control groups (TABLE 7 and FIG. 15A); 57 out of 72 groups (79%) treated with *Bacillus subtilis*, *Bacillus pumilus* or both had better yields than control groups (TABLE 8 and FIG. 15B); and 53 out of 72 groups (74%) treated with *Bacillus subtilis*, *Bacillus pumilus* or both had better yields than control groups (TABLE 9 and FIG. 15C).

TABLE 7

| | Antimicrobial composition | Yield (cwt) | | | | | | | |
|---|---|---|---|---|---|---|---|---|---|
| | | Red End. (1) | Red End. (2) | Superior (1) | Superior (2) | Oneida Gold (1) | Oneida Gold (2) | Dark Red Norland (1) | Dark Red Norland (2) |
| Wisconsin 1 | Control | 401.4 | 395.1 | 417.6 | 401.4 | 421.0 | 410.5 | 446.0 | 415.6 |
| Wisconsin 2 | *B. subtlius* (½ Gal/A) | 402.6 | 402.1 | 422.0 | 402.1 | 424.2 | 411.9 | 450.7 | 416.8 |
| Wisconsin 3 | *B. subtlius* (1 Gal/A) | 423.1 | 403.0 | 424.6 | 401.8 | 423.0 | 418.6 | 464.2 | 416.2 |
| Wisconsin 4 | *B. subtlius* (2 Gal/A) | 422.8 | 422.2 | 417.5 | 400.6 | 421.8 | 421.9 | 442.5 | 437.9 |
| Wisconsin 5 | *Bacillus pumilus* (½ Gal/A) | 404.5 | 394.0 | 422.3 | 405.0 | 416.8 | 409.7 | 462.5 | 405.3 |
| Wisconsin 6 | *Bacillus pumilus* (1 Gal/A) | 425.0 | 396.6 | 423.4 | 397.1 | 422.4 | 420.2 | 452.6 | 412.3 |
| Wisconsin 7 | *Bacillus pumilus* (2 Gal/A) | 426.9 | 415.2 | 423.8 | 403.4 | 417.5 | 412.3 | 460.5 | 421.6 |
| Wisconsin 8 | *B. subtlius* + *Bacillus pumilus* (½ Gal/A) | 419.1 | 405.5 | 419.1 | 400.7 | 419.5 | 416.8 | 459.1 | 413.5 |
| Wisconsin 9 | *B. subtlius* + *Bacillus pumilus* (1 Gal/A) | 418.4 | 403.1 | 410.1 | 396.5 | 420.1 | 419.5 | 454.9 | 414.3 |
| Wisconsin 10 | *B. subtlius* + *Bacillus pumilus* (2 Gal/A) | 414.3 | 417.9 | 423.1 | 395.2 | 424.8 | 418.4 | 456.6 | 423.5 |

TABLE 8

| | Antimicrobial composition | Cull Rate (%) | | | | | | | |
|---|---|---|---|---|---|---|---|---|---|
| | | Red End. (1) | Red End. (2) | Superior (1) | Superior (2) | Oneida Gold (1) | Oneida Gold (2) | Dark Red Norland (1) | Dark Red Norland (2) |
| Wisconsin 1 | Control | 10.7 | 13.8 | 2.9 | 5.6 | 11.3 | 4.7 | 23.2 | 8.7 |
| Wisconsin 2 | *B. subtlius* (½ Gal/A) | 7.6 | 9.9 | 3.8 | 2.5 | 8.1 | 13.3 | 6.4 | 9.4 |
| Wisconsin 3 | *B. subtlius* (1 Gal/A) | 4.0 | 8.9 | 1.7 | 4.5 | 6.6 | 9.4 | 10.7 | 7.4 |
| Wisconsin 4 | *B. subtlius* (2 Gal/A) | 4.8 | 10.8 | 3.0 | 3.6 | 4.4 | 6.6 | 9.4 | 6.1 |
| Wisconsin 5 | *Bacillus pumilus* (½ Gal/A) | 6.7 | 6.0 | 2.5 | 4.4 | 10.0 | 9.4 | 10.2 | 9.1 |
| Wisconsin 6 | *Bacillus pumilus* (1 Gal/A) | 6.1 | 5.3 | 2.3 | 3.7 | 7.5 | 7.4 | 11.9 | 3.1 |
| Wisconsin 7 | *Bacillus pumilus* (2 Gal/A) | 3.1 | 10.9 | 1.2 | 5.8 | 6.7 | 10.8 | 15.4 | 4.7 |
| Wisconsin 8 | *B. subtlius* + *Bacillus pumilus* (½ Gal/A) | 5.5 | 10.8 | 3.1 | 5.2 | 7.4 | 7.0 | 10.1 | 5.6 |
| Wisconsin 9 | *B. subtlius* + *Bacillus pumilus* (1 Gal/A) | 3.7 | 7.5 | 2.0 | 5.5 | 8.8 | 12.9 | 9.6 | 5.0 |
| Wisconsin 10 | *B. subtlius* + *Bacillus pumilus* (2 Gal/A) | 3.7 | 8.5 | 2.1 | 4.9 | 7.6 | 9.9 | 5.3 | 5.6 |

TABLE 9

| | Antimicrobial composition | Scab Severity (0-6) | | | | | | | |
|---|---|---|---|---|---|---|---|---|---|
| | | Red End. (1) | Red End. (2) | Superior (1) | Superior (2) | Oneida Gold (1) | Oneida Gold (2) | Dark Red Norland (1) | Dark Red Norland (2) |
| Wisconsin 1 | Control | 2.4 | 2.8 | 0.4 | 0.4 | 1.8 | 1.9 | 2.9 | 3.0 |
| Wisconsin 2 | *B. subtlius* (½ Gal/A) | 2.5 | 2.5 | 0.4 | 0.4 | 1.4 | 1.4 | 1.9 | 1.8 |
| Wisconsin 3 | *B. subtlius* (1 Gal/A) | 1.2 | 1.2 | 0.4 | 0.4 | 0.9 | 0.8 | 1.3 | 1.3 |
| Wisconsin 4 | *B. subtlius* (2 Gal/A) | 0.8 | 0.8 | 0.4 | 0.4 | 0.8 | 0.8 | 0.9 | 0.8 |
| Wisconsin 5 | *Bacillus pumilus* (½ Gal/A) | 1.2 | 1.3 | 0.4 | 4.0 | 0.8 | 0.8 | 1.2 | 1.3 |
| Wisconsin 6 | *Bacillus pumilus* (1 Gal/A) | 0.9 | 0.7 | 0.4 | 0.5 | 0.8 | 0.8 | 0.8 | 0.8 |
| Wisconsin 7 | *Bacillus pumilus* (2 Gal/A) | 0.9 | 0.8 | 0.4 | 0.5 | 0.8 | 0.9 | 0.8 | 0.8 |
| Wisconsin 8 | *B. subtlius* + *Bacillus pumilus* (½ Gal/A) | 0.8 | 0.8 | 0.4 | 0.4 | 0.5 | 0.4 | 0.8 | 0.8 |
| Wisconsin 9 | *B. subtlius* + *Bacillus pumilus* (1 Gal/A) | 0.4 | 0.9 | 0.5 | 0.4 | 0.4 | 0.4 | 0.5 | 0.4 |
| Wisconsin 10 | *B. subtlius* + *Bacillus pumilus* (2 Gal/A) | 0.4 | 0.4 | 0.4 | 0.4 | 0.4 | 0.4 | 0.5 | 0.4 |

In the Maine trial, potatoes treated with *Bacillus subtilis*, *Bacillus pumilus* or both were generally better than the control group in all three metrics: yield, cull rate, and scab severity rating (percentage surface area with scab lesions), except one instance of a lower yield than the control group and one instance of a lower percentage marketability than the control group (TABLE 10 and FIG. 16).

TABLE 10

| Cultivar | Antimicrobial composition | Yield (cwt/A) | Marketable Yield (cwt/A) | Marketable (%) |
|---|---|---|---|---|
| Katahdin | Maine 1 Control | 175.9 | 123.6 | 70% |
| | Maine 2 *Bacillus pumilus* (1 Gal/A) | 177.9 | 140.8 | 78% |
| | Maine 3 *Bacillus subtilus* (1 Gal/A) | 180.2 | 136.0 | 76% |
| | Maine 4 *Bacillus pumilus* + *Bacillus subtilus* (1 Gal/A) | 165.4 | 122.7 | 74% |
| Kennebec | Maine 1 Control | 149.2 | 90.0 | 59% |
| | Maine 2 *Bacillus pumilus* (1 Gal/A) | 146.4 | 100.7 | 69% |
| | Maine 3 *Bacillus subtilus* (1 Gal/A) | 181.0 | 108.0 | 57% |
| | Maine 4 *Bacillus pumilus* + *Bacillus subtilus* (1 Gal/A) | 202.5 | 125.1 | 64% |

With extremely high win rates in yield, marketable yield, cull rate, and scab severity rating, both *Bacillus pumilus* and *Bacillus subtilis* (and a combination of the two) provide effective treatments for potato scab. The average decrease in scab severity of 45.8% versus the control group is substantial.

4.5.11. Example 11: Field Experiment (Prince Edward Island and New Brunswick, Canada)

A total of 13 experiments were conducted in Canada (5 locations in New Brunswick and 8 locations in Prince Edward Island) on farmer's fields. Field sites with a history of potato scab disease were selected. Levelled uniform area was selected in each field and the experiments were performed as follows:

Treatments: There were four treatments in each experiment—control (water treated), BS (*Bacillus subtilis*), BP (*Bacillus pumilus*), Mix (*B. subtilis*+*Bacillus pumilus*).

Experimental design: Each experiment was laid out as Latin square design with 4 replications. Each treatment was a 20 feet long potato row.

Treatment application: Already seeded potato hills were opened and the potato seeds were fully exposed. Treatments (liquid product diluted 10× in water and applied @ 1000 mL per treatment per replication) were applied in open furrows including the potato seeds and the hills were closed immediately. A summary of the locations, sites and potato cultivars tested is presented in TABLE 11.

TABLE 11

| Location | Site # | Farm | Cultivar |
|---|---|---|---|
| New Brunswick | 1 | Andre Cote | Kennebec |
| New Brunswick | 2 | Eric Cote | Red Pontiac |
| New Brunswick | 3 | Brennan Farms | Kennebec |
| New Brunswick | 4 | Brennan Farms | Red Pontiac |
| New Brunswick | 5 | Robbie Green | Shepody |
| Prince Edward Island | 6 | Robbie Green | Russet Burbank |
| Prince Edward Island | 7 | Marven Stwart | Atlantic |
| Prince Edward Island | 8 | Docherty Farm | Red Lasota |
| Prince Edward Island | 9 | Townshend Bros | Sifra |
| Prince Edward Island | 10 | McAulay Farm | Prospect |
| Prince Edward Island | 11 | Harrington Farm | Shepody |
| Prince Edward Island | 12 | Harrington Farm | Goldrush |
| Prince Edward Island | 13 | Coffin Farm | Prospect |

Bacterial culture preparation: Bacterial culture (*Bacillus subtilis* and *Bacillus pumilus*) were grown separately in LB broth medium at 30° C., shaken at 150 rpm for 7 days. The cultures were mixed for treatments when necessary (1:1) and a cell supernatant composition of the microorganism mixture of IN-M1 added.

Application: a cell supernatant composition of the microorganism mixture of IN-M1 was added to the bacterial culture @ 10 oz/gallon.

Harvest: Potatoes were harvested at the end of the experiment (14-16 weeks) and data were collected on disease severity (<5%, 5-25%, >25% potato surface area affected).

*Bacillus pumilus* and *Bacillus subtilis* (and a combination of the two) provide effective treatments for potato scab, and the cell supernatant composition of the microorganism mixture of IN-M1 provides other benefits as described in in US Publication Nos. 20160100587 and 20160102251, and U.S. Pat. No. 9,175,258, which are incorporated by reference in their entireties herein.

5. INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

6. EQUIVALENTS

While various specific embodiments have been illustrated and described, the above specification is not restrictive. It will be appreciated that various changes can be made without departing from the spirit and scope of the invention(s). Many variations will become apparent to those skilled in the art upon review of this specification.

| SEQ ID NO | | Sequences |
|---|---|---|
| 1 | 16S rRNA ITI-1 | GAGCTTGCTCCCGGATGTTAGCGGCGGACGGGTGAGTAACACGTGGGT AACCTGCCTGTAAGACTGGGATAACTCCGGGAAACCGGAGCTAATACC GGATAGTTCCTTGAACCGCATGGTTCAAGGATGAAAGACGGTTTCGGCT GTCACTTACAGATGGACCCGCGGCGCATTAGCTAGTTGGTGAGGTAAC GGCTCACCAAGGCGACGATGCGTAGCCGACCTGAGAGGGTGATCGGCC ACACTGGGACTGAGACACGGCCCAGACTCCTACGGGAGGCAGCAGTAG GGAATCTTCCGCAATGGACGAAAGTCTGACGGAGCAACGCCGCGTGAG TGATGAAGGTTTTCGGATCGTAAAGCTCTGTTGTTAGGGAAGAACAAGT GCAAGAGTAACTGCTTGCACCTTGACGGTACCTAACCAGAAAGCCACG GCTAACTACGTGCCAGCAGCCGCGGTAATACGTAGGTGGCAAGCGTTG TCCGGAATTATTGGGCGTAAAGGGCTCGCAGGCGGTTTCTTAAGTCTGA TGTGAAAGCCCCCGGCTCAACCGGGGAGGGTCATTGGAAACTGGGAAA CTTGAGTGCAGAAGAGGAGAGTGGAATTCCACGTGTAGCGGTGAAATG CGTAGAGATGTGGAGGAACACCAGTGGCGAAGGCGACTCTCTGGTCTG TAACTGACGCTGAGGAGCGAAAGCGTGGGGAGCGAACAGGATTAGATA CCCTGGTAGTCCACGCCGTAAACGATGAGTGCTAAGTGTTAGGGGGTTT CCGCCCCTTAGTGCTGCAGCTAACGCATTAAGCACTCCGCCTGGGGAGT ACGGTCGCAAGACTGAAACTCAAAGGAATTGACGGGGGCCCGCACAAG CGGTGGAGCATGTGGTTTAATTCGAAGCAACGCGAAGAACCTTACCAG GTCTTGACATCCTCTGACAACCCTAGAGATAGGGCTTTCCCTTCGGGGA CAGAGTGACAGGTGGTGCATGGTTGTCGTCAGCTCGTGTCGTGAGATGT TGGGTTAAGTCCCGCAACGAGCGCAACCCTTGATCTTAGTTGCCAGCAT TCAGTTGGGCACTCTAAGGTGACTGCCGGTGACAAACCGGAGGAAGGT GGGGATGACGTCAAATCATCATGCCCCTTATGACCTGGGCTACACACGT GCTACAATGGACAGAACAAAGGGCTGCGAGACCGCAAGGTTTAGCCAA TCCCACAAATCTGTTCTCAGTTCGGATCGCAGTCTGCAACTCGACTGCG TGAAGCTGGAATCGCTAGTAATCGCGGATCAGCATGCCGCGGTGAATA CGTTCCCGGGCCTTGTACACACCGCCCGTCACACCACGAGAGTTTGCAA CACCCGAAGTCGGTGAGGTAACC |
| 2 | 16S rRNA ITT-2 | GCAGTCGAGCGGACAGATGGGAGCTTGCTCCCTGATGTTAGCGGCGGA CGGGTGAGTAACACGTGGGTAACCTGCCTGTAAGACTGGGATAACTCC GGGAAACCGGGGCTAATACCGGATGCTTGTTTGAACCGCATGGTTCAA ACATAAAAGGTGGCTTCGGCTACCACTTACAGATGGACCCGCGGCGCA TTANNTAGTTGGTGAGGTAACGGCTCACCAAGGCAACGATGCGTAGCC GACCTGAGAGGGTGATCGGCCACACTGGGACTGAGACACGGCCCAGAC TCCTACGGGAGGCAGCAGTAGGGAATCTTCCGCAATGGACGAAAGTCT GACGGAGCAACGCCGCGTGAGTGATGAAGGTTTTCGGATCGTAAAGCT CTGTTGTTAGGGAAGAACAAGTACCGTTCGAATAGGGCGGTACCTTGA CGGTACCTAACCAGAAAGCCACGGCTAACTACGTGCCAGCAGCCGCGG TAATACGTAGGTGGCAAGCGTTGTCCGGAATTATTGGGCGTAAAGGGC TCGCAGGCGGTTTCTTAAGTCTGATGTGAAAGCCCCCGGCTCAACCGGG GAGGGTCATTGGAAACTGGGGAACTTGAGTGCAGAAGAGGAGAGTGG AATTCCACGTGTAGCGGTGAAATGCGTAGAGATGTGGAGGAACACCAG TGGCGAAGGCGACTCTCTGGTCTGTAACTGACGCTGAGGAGCGAAAGC GTGGGGAGCGAACAGGATTAGATACCCTGGTAGTCCACGCCGTAAACG ATGAGTGCTAAGTGTTAGGGGGTTTCCGCCCCTTAGTGCTGCAGCTAAC GCATTAAGCACTCCGCCTGGGGAGTACGGTCGCAAGACTGAAACTCAA AGGAATTGACGGGGGCCCGCACAAGCGGTGGAGCATGTGGTTTAATTC GAAGCAACGCGAAGAACCTTACCAGGTCTTGACATCCTCTGACAATCCT AGAGATAGGACGTCCCCTTCGGGGGCAGAGTGACAGGTGGTGCATGGT TGTCGTCAGCTCGTGTCGTGAGATGTTGGGTTAAGTCCCGCAACGAGCG CAACCCTTGATCTTAGTTGCCAGCATTCAGTTGGGCACTCTAAGGTGAC TGCCGGTGACAAACCGGAGGAAGGTGGGGATGACGTCAAATCATCATG |

Sequences

| SEQ ID NO | | |
|---|---|---|
| | | CCCCTTATGACCTGGGCTACACACGTGCTACAATGGACAGAACAAAGG<br>GCAGCGAAACCGCGAGGTTAAGCCAATCCCACAAATCTGTTCTCAGTTC<br>GGATCGCAGTCTGCAACTCGACTGCGTGAAGCTGGAATCGCTAGTAATC<br>GCGGATCAGCATGCCGCGGTGAATACGTTCCCGGGCCTTGTACACACCG<br>CCCGTCACACCACGAGAGTTTGTAACACCCGAAGTCGGTGAGGTAACC |
| 3 | 16S rRNA ITT-3 | TAGTTGGTGAGGTAACGGCTCACCAAGGCAACGATGCGTAGCCGACCT<br>GAGAGGGTGATCGGCCACACTGGGACTGAGACACGGCCCAGACTCCTA<br>CGGGAGGCAGCAGTAGGGAATCTTCCGCAATGGACGAAAGTCTGACGG<br>AGCAACGCCGCGTGAGTGATGAAGGTTTTCGGATCGTAAAGCTCTGTTG<br>TTAGGGAAGAACAAGTACCGTTCGAATAGGGCGGTACCTTGACGGTAC<br>CTAACCAGAAAGCCACGGCTAACTACGTGCCAGCAGCCGCGGTAATAC<br>GTAGGTGGCAAGCGTTGTCCGGAATTATTGGGCGTAAAGGGCTCGCAG<br>GCGGTTTCTTAAGTCTGATGTGAAAGCCCCCGGCTCAACCGGGGAGGGT<br>CATTGGAAACTGGGGAACTTGAGTGCAGAAGAGGAGAGTGGAATTCCA<br>CGTGTAGCGGTGAAATGCGTAGAGATGTGGAGGAACACCAGTGGCGAA<br>GGCGACTCTCTGGTCTGTAACTGACGCTGAGGAGCGAAAGCGTGGGGA<br>GCGAACAGGATTAGATACCCTGGTAGTCCACGCCGTAAACGATGAGTG<br>CTAAGTGTTAGGGGGTTTCCGCCCCTTAGTGCTGCAGCTAACGCATTAA<br>GCACTCCGCCTGGGGAGTACGGTCGCAAGACTGAAACTCAAAGGAATT<br>GACGGGGGCCCGCACAAGCGGTGGAGCATGTGGTTTAATTCGAAGCAA<br>CGCGAAGAACCTTACCAGGTCTTGACATCCTCTGACAATCCTAGAGATA<br>GGACGTCCCCTTCGGGGCAGAGTGACAGGTGGTGCATGGTTGTCGTC<br>AGCTCGTGTCGTGAGATGTTGGGTTAAGTCCCGCAACGAGCGCAACCCT<br>TGATCTTAGTTGCCAGCATTCAGTTGGGCACTCTAAGGTGACTGCCGGT<br>GACAAACCGGAGGAAGGTGGGGATGACGTCAAATCATCATGCCCCTTA<br>TGACCTGGGCTACACACGTGCTACAATGGACAGAACAAAGGGCAGCGA<br>AACCGCGAGGTTAAGCCAATCCCACAAATCTGTTCTCAGTTCGGATCGC<br>AGTCTGCAACTCGACTGCGTGAAGCTGGAATCGCTAGTAATCGCGGATC<br>AGCATGCCGCGGTGAATACGTTCCCGGGCCTTGTACACACCGCCCGTCA<br>CACCACGAGAGTTTGTAACACCCGAAGTCGGTGAGGTAACC |
| 4 | Bacillus pumilus strain NES-CAP-1 (GenBank Accession No. MF079281.1) | GTGCGGGTGCTATAATGCAGTCGAGCGGACAGAAGGGAGCTTGCTCCC<br>GGATGTTAGCGGCGACGGGTGAGTAACACGTGGGTAACCTGCCTGTA<br>AGACTGGGATAACTCCGGGAAACCGGAGCTAATACCGGATAGTTCCTT<br>GAACCGCATGGTTCAAGGATGAAAGACGGTTTCGGCTGTCACTTACAG<br>ATGGACCCGCGGCGCATTAGCTAGTTGGTGAGGTAACGGCTCACCAAG<br>GCGACGATGCGTAGCCGACCTGAGAGGGTGATCGGCCACACTGGGACT<br>GAGACACGGCCCAGACTCCTACGGGAGGCAGCAGTAGGGAATCTTCCG<br>CAATGGACGAAAGTCTGACGGAGCAACGCCGCGTGAGTGATGAAGGTT<br>TTCGGATCGTAAAGCTCTGTTGTTAGGGAAGAACAAGTGCAAGAGTAA<br>CTGCTTGCACCCTTGACGGTACCTAACCAGAAAGCCACGGCTAACTACGT<br>GCCAGCAGCCGCGGTAATACGTAGGTGGCAAGCGTTGTCCGGAATTAT<br>TGGGCGTAAAGGGCTCGCAGGCGGTTTCTTAAGTCTGATGTGAAAGCCC<br>CCGGCTCAACCGGGGAGGGTCATTGGAAACTGGGAAACTTGAGTGCAG<br>AAGAGGAGAGTGGAATTCCACGTGTAGCGGTGAAATGCGTAGAGATGT<br>GGAGGAACACCAGTGGCGAAGGCGACTCTCTGGTCTGTAACTGACGCT<br>GAGGAGCGAAAGCGTGGGGAGCGAACAGGATTAGATACCCTGGTAGTC<br>CACGCCGTAAACGATGAGTGCTAAGTGTTAGGGGGTTTCCGCCCCTTAG<br>TGCTGCAGCTAACGCATTAAGCACTCCGCCTGGGGAGTACGGTCGCAA<br>GACTGAAACTCAAAGGAATTGACGGGGGCCCGCACAAGCGGTGGAGCA<br>TGTGGTTTAATTCGAAGCAACGCGAAGAACCTTACCAGGTCTTGACATC<br>CTCTGACAACCCTAGAGATAGGGCTTTCCCTTCGGGGACAGAGTGACA<br>GGTGGTGCATGGTTGTCGTCAGCTCGTGTCGTGAGATGTTGGGTTAAGT<br>CCCGCAACGAGCGCAACCCTTGATCTTAGTTGCCAGCATTCAGTTGGGC<br>ACTCTAAGGTGACTGCCGGTGACAAACCGGAGGAAGGTGGGGATGACG<br>TCAAATCATCATGCCCCTTATGACCTGGGCTACACACGTGCTACAATGG<br>ACAGAACAAAGGGCTGCGAGACCGCAAGGTTTAGCCAATCCCACAAAT<br>CTGTTCTCAGTTCGGATCGCAGTCTGCAACTCGACTGCGTGAAGCTGGA<br>ATCGCTAGTAATCGCGGATCAGCATGCCGCGGTGAATACGTTCCCGGGC<br>CTTGTACACACCGCCCGTCACACCACGAGAGTTTGCAACACCCGAAGTC<br>GGTGAGGTAACCTTTATGGAGCCAGCCGCCGAACGTTC |
| 5 | Bacillus subtilis strain BSFLG01 (GenBank Accession No. MF196314.1) | TGGCGGCGTGCTATAATGCAGTCGAGCGGACAGATGGGAGCTTGCTCC<br>CTGATGTTAGCGGCGGACGGGTGAGTAACACGTGGGTAACCTGCCTGT<br>AAGACTGGGATAACTCCGGGAAACCGGGGCTAATACCGGATGCTTGTT<br>TGAACCGCATGGTTCAAACATAAAAGGTGGCTTCGGCTACCACTTACAG<br>ATGGACCCGCGGCGCATTAGCTAGTTGGTGAGGTAACGGCTCACCAAG<br>GCAACGATGCGTAGCCGACCTGAGAGGGTGATCGGCCACACTGGGACT<br>GAGACACGGCCCAGACTCCTACGGGAGGCAGCAGTAGGGAATCTTCCG<br>CAATGGACGAAAGTCTGACGGAGCAACGCCGCGTGAGTGATGAAGGTT<br>TTCGGATCGTAAAGCTCTGTTGTTAGGGAAGAACAAGTACCGTTCGAAT<br>AGGGCGGTACCTTGACGGTACCTAACCAGAAAGCCACGGCTAACTACG<br>TGCCAGCAGCCGCGGTAATACGTAGGTGGCAAGCGTTGTCCGGAATTA |

| SEQ ID NO | | Sequences |
|---|---|---|
| | | TTGGGCGTAAAGGGCTCGCAGGCGGTTTCTTAAGTCTGATGTGAAAGCC CCCCGGCTCAACCGGGGAGGGTCATTGGAAACTGGGGAACTTGAGTGCA GAAGAGGAGAGTGGAATTCCACGTGTAGCGGTGAAATGCGTAGAGATG TGGAGGAACACCAGTGGCGAAGGCGACTCTCTGGTCTGTAACTGACGC TGAGGAGCGAAAGCGTGGGGAGCGAACAGGATTAGATACCCTGGTAGT CCACGCCGTAAACGATGAGTGCTAAGTGTTAGGGGGTTTCCGCCCCTTA GTGCTGCAGCTAACGCATTAAGCACTCCGCCTGGGGAGTACGGTCGCA AGACTGAAACTCAAAGGAATTGACGGGGGCCCGCACAAGCGGTGGAGC ATGTGGTTTAATTCGAAGCAACGCGAAGAACCTTACCAGGTCTTGACAT CCTCTGACAATCCTAGAGATAGGACGTCCCCTTCGGGGGCAGAGTGAC AGGTGGTGCATGGTTGTCGTCAGCTCGTGTCGTGAGATGTTGGGTTAAG TCCCGCAACGAGCGCAACCCTTGATCTTAGTTGCCAGCATTCAGTTGGG CACTCTAAGGTGACTGCCGGTGACAAACCGGAGGAAGGTGGGGATGAC GTCAAATCATCATGCCCCTTATGACCTGGGCTACACACGTGCTACAATG GACAGAACAAAGGGCAGCGAAACCGCGAGGTTAAGCCAATCCCACAA ATCTGTTCTCAGTTCGGATCGCAGTCTGCAACTCGACTGCGTGAAGCTG GAATCGCTAGTAATCGCGGATCAGCATGCCGCGGTGAATACGTTCCCG GGCCTTGTACACACCGCCCGTCACACCACGAGAGTTTGTAACACCCGAA GTCGGTGAGGTAACCTTTTAGGAGCCAGCCGCCGAAGGGACAGAGAG |
| 6 | *Bacillus subtilis* strain SSL2 (GenBank Accession No. MH192382.1) | CTGGCTCAGGACGAACGCTGGCGGCGTGCCTAATACATGCAAGTCGAG CGGACAGATGGGAGCTTGCTCCCTGATGTTAGCGGCGGACGGGTGAGT AACACGTGGGTAACCTGCCTGTAAGACTGGGATAACTCCGGGAAACCG GGGCTAATACCGGATGGTTGTTGAACCGCATGGTTCAAACATAAAAG GTGGCTTCGGCTACCACTTACAGATGGACCCGCGGCGCATTAGCTAGTT GGTGAGGTAACGGCTCACCAAGGCAACGATGCGTAGCCGACCTGAGAG GGTGATCGGCCACACTGGGACTGAGACACGGCCCAGACTCCTACGGGA GGCAGCAGTAGGGAATCTTCCGCAATGGACGAAAGTCTGACGGAGCAA CGCCGCGTGAGTGATGAAGGTTTTCGGATCGTAAAGCTCTGTTGTTAGG GAAGAACAAGTACCGTTCGAATAGGGCGGTACCTTGACGGTACCTAAC CAGAAAGCCACGGCTAACTACGTGCCAGCAGCCGCGGTAATACGTAGG TGGCAAGCGTTGTCCGGAATTATTGGGCGTAAAGGGCTCGCAGGCGGT TTCTTAAGTCTGATGTGAAAGCCCCCGGCTCAACCGGGGAGGGTCATTG GAAACTGGGGAACTTGAGTGCAGAAGAGGAGAGTGGAATTCCACGTGT AGCGGTGAAATGCGTAGAGATGTGGAGGAACACCAGTGGCGAAGGCG ACTCTCTGGTCTGTAACTGACGCTGAGGAGCGAAAGCGTGGGGAGCGA ACAGGATTAGATACCCTGGTAGTCCACGCCGTAAACGATGAGTGCTAA GTGTTAGGGGGTTTCCGCCCCTTAGTGCTGCAGCTAACGCATTAAGCAC TCCGCCTGGGGAGTACGGTCGCAAGACTGAAACTCAAAGGAATTGACG GGGGCCCGCACAAGCGGTGGAGCATGTGGTTTAATTCGAAGCAACGCG AAGAACCTTACCAGGTCTTGACATCCTCTGACAATCCTAGAGATAGGAC GTCCCCTTCGGGGGCAGAGTGACAGGTGGTGCATGGTTGTCGTCAGCTC GTGTCGTGAGATGTTGGGTTAAGTCCCGCAACGAGCGCAACCCTTGATC TTAGTTGCCAGCATTCAGTTGGGCACTCTAAGGTGACTGCCGGTGACAA ACCGGAGGAAGGTGGGGATGACGTCAAATCATCATGCCCCTTATGACC TGGGCTACACACGTGCTACAATGGACAGAACAAAGGGCAGCGAAACCG CGAGGTTAAGCCAATCCCACAAATCTGTTCTCAGTTCGGATCGCAGTCT GCAACTCGACTGCGTGAAGCTGGAATCGCTAGTAATCGCGGATCAGCA TGCCGCGGTGAATACGTTCCCGGGCCTTGTACACACCGCCCGTCACACC ACGAGAGTTTGTAACACCCGAAGTCGGTGAGGTAACCTTTTAGGAGCC AGCCGCCGAAGGTGGGACAGATGATTGGGGTGAAGTCGTAACAAGGTA GCCGTATCGGAAGGTGCGGTTGGAT |

What is claimed is:

1. A method of controlling, suppressing and/or preventing infection from *Streptomyces scabies* in potatoes, comprising the step of:
providing an antimicrobial composition comprising at least one of *Bacillus pumilus* strain, a culture medium inoculated with *Bacillus pumilus*, a purified extract of *Bacillus pumilus* or at least one metabolite of *Bacillus pumilus*, wherein said antimicrobial composition comprises Micrococcin P1; and
applying an effective amount of said antimicrobial composition to at least one of potatoes tubers, potatoes roots, potatoes stems, potatoes leaves, and potatoes propagules.

2. The method of claim 1, wherein the Micrococcin P1 is produced by the *Bacillus pumilus*.

3. The method of claim 1, wherein the composition further comprises a cell free supernatant of a microorganism mixture comprising *Lactobacillus paracasei*, *Lactobacillus helveticus*, *Lactobacillus plantarum*, *Lactobacillus rhamnosus*, *Lactococcus lactis*, *Bacillus amyloliquefaciens*, *Aspergillus oryzae*, *Saccharomyces cerevisiae*, *Candida utilis*, and *Rhodopseudomonas palustris*, or a mixture thereof.

4. The method of claim 1, wherein said method provides for bioprotection of potatoes against *Streptomyces scabies*, and wherein said bioprotection is determined by comparing damages of potatoes contacted or not with said antimicrobial composition.

5. The method of claim 1, wherein said method provides for at least one of: enhancing resistance against *Streptomyces scabies*, reduction damage caused by *Streptomyces scabies*, enhancing plant antimicrobial response against *Streptomyces scabies*, increasing plant antinematocidal activity, and reducing pathological symptoms or lesions resulting from actions of *Streptomyces scabies*, and increasing tuber yield.

6. The method of claim 1, wherein said *Bacillus pumilus* strain comprises a 16S rRNA having at least 95% identity with SEQ ID NO: 4.

7. The method of claim 1, wherein said antimicrobial composition further comprises at least one strain of *Bacillus subtilis*, a culture medium inoculated with *Bacillus subtilis*, a cell-free extract of *Bacillus subtilis* or at least one metabolite of *Bacillus subtilis*.

8. The method of claim 1, wherein said antimicrobial composition further comprises at least one of an herbicide, an insecticide, a fungicide and a nutrient.

9. The method of claim 1, wherein the purified extract of *Bacillus pumilus* comprises a cell-free supernatant of *Bacillus pumilus*.

10. A composition effective in bioprotection of potatoes from *Streptomyces scabies*, comprising:
an effective amount of Micrococcin P1; and
an agriculturally acceptable carrier,
wherein said composition is formulated for application to at least one of potatoes tubers, potatoes roots, potatoes stems, potatoes leaves and potatoes propagules; and
wherein said Micrococcin P1 is effective in controlling, suppressing and/or preventing infection from *Streptomyces scabies*.

11. The composition of claim 10, wherein the Micrococcin P1 is produced by *Bacillus pumilus*.

12. The composition of claim 10, further comprising *Bacillus subtilus*.

13. The composition of claim 10, further comprising a filtered fraction of a microbial culture comprising *Lactoba-* cillus paracasei, Lactobacillus helveticus, Lactobacillus plantarum, Lactobacillus rhamnosus, Lactococcus lactis, Bacillus amyololiquefaciens, Aspergillus oryzae, Saccharomyces cerevisiae, Candida utilis, and Rhodopseudomonas palustris, or a mixture thereof.

14. The composition of claim 10, wherein said Bacillus pumilus strain comprises a 16S rRNA having at least 95% identity with SEQ ID NO: 4.

15. The composition of claim 10, further comprising at least one strain of Bacillus subtilis, a culture medium inoculated with Bacillus subtilis, a cell-free extract of Bacillus subtilis or at least one metabolite of Bacillus subtilis.

16. A method of protecting potatoes from Streptomyces scabies, comprising the step of:
applying an effective amount of the composition of claim 10 to a soil where potato plants are growing,
wherein the effective amount is sufficient for bioprotection of the potatoes from Streptomyces scabies.

* * * * *